United States Patent
Wu et al.

(10) Patent No.: US 10,537,406 B2
(45) Date of Patent: *Jan. 21, 2020

(54) DENTAL APPLIANCE WITH REPOSITIONING JAW ELEMENTS

(71) Applicant: Align Technology, Inc., San Jose, CA (US)

(72) Inventors: Ken Wu, San Jose, CA (US); Eric E. Kuo, San Jose, CA (US); Mitra Derakhshan, Herndon, VA (US); Crystal Tjhia, Sunnyvale, CA (US); Eric Yau, Saratoga, CA (US); Allen R. Boronkay, San Jose, CA (US); Chunhua Li, Cupertino, CA (US); Gleb Krivovyaz, Moscow (RU)

(73) Assignee: Align Technology, Inc., San Jose, CA (US)

( * ) Notice: Subject to any disclaimer, the term of this patent is extended or adjusted under 35 U.S.C. 154(b) by 661 days.

This patent is subject to a terminal disclaimer.

(21) Appl. No.: 14/491,765

(22) Filed: Sep. 19, 2014

(65) Prior Publication Data
US 2015/0238280 A1    Aug. 27, 2015

Related U.S. Application Data
(63) Continuation-in-part of application No. 14/186,856, filed on Feb. 21, 2014.

(51) Int. Cl.
| | | |
|---|---|---|
| A61C 7/08 | (2006.01) | |
| A61C 7/00 | (2006.01) | |
| A61C 7/36 | (2006.01) | |

(52) U.S. Cl.
CPC .............. A61C 7/08 (2013.01); A61C 7/002 (2013.01); A61C 7/36 (2013.01)

(58) Field of Classification Search
CPC .. A61C 7/08; A61C 7/002; A61C 7/36; A61C 7/00
(Continued)

(56) References Cited

U.S. PATENT DOCUMENTS

| | | |
|---|---|---|
| 2,171,695 A | 9/1939 | Harper |
| 2,467,432 A | 4/1949 | Kesling |

(Continued)

FOREIGN PATENT DOCUMENTS

| | | |
|---|---|---|
| CN | 105997274 A | 10/2016 |
| DE | 10201205323 A1 | 9/2013 |

(Continued)

OTHER PUBLICATIONS

Co-pending U.S. Appl. No. 15/812,127, filed Nov. 14, 2017.
(Continued)

*Primary Examiner* — Matthew M Nelson
(74) *Attorney, Agent, or Firm* — Wilson Sonsini Goodrich & Rosati

(57) ABSTRACT

The present disclosure provides method, computing device readable medium, and devices for dental appliances with repositioning jaw elements. An example of a method can include identifying a misaligned jaw of a patient from a virtual image of the patient's jaw, providing a treatment plan for the patient including a virtual model of a dental appliance having a first shell and a second shell configured to reposition at least one tooth of the patient, and adjusting the position of the repositioning jaw elements on the first shell and the second shell to comply with a number of constraints. The virtual model of the dental appliance including repositioning jaw elements on the first shell and the second shell configured to move a position of the misaligned jaw of the patient.

29 Claims, 18 Drawing Sheets

(58) Field of Classification Search
USPC .................................. 433/6, 18–19, 24–25
See application file for complete search history.

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Edward |
| 3,496,936 A | 2/1970 | Kenneth |
| 3,600,808 A | 8/1971 | James |
| 3,660,900 A | 5/1972 | Lawrence |
| 3,683,502 A | 8/1972 | Melvin |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,478,580 A | 10/1984 | Barrut |
| 4,500,294 A | 2/1985 | Lewis |
| 4,509,918 A | 2/1985 | Clark |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,103,838 A | 4/1992 | Yousif |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,683,244 A * | 11/1997 | Truax .................. A61C 7/00 433/24 |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,794,627 A | 8/1998 | Frantz et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,200,133 B1 | 3/2001 | Kittelsen |
| 6,217,325 B1 | 4/2001 | Chishti et al. |
| 6,217,334 B1 | 4/2001 | Hultgren |
| 6,244,861 B1 | 6/2001 | Andreiko et al. |

(56) References Cited

U.S. PATENT DOCUMENTS

| | | | |
|---|---|---|---|
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,405,729 B1 | 6/2002 | Thornton | |
| 6,450,807 B1 | 9/2002 | Chishti et al. | |
| 6,482,298 B1 | 11/2002 | Bhatnagar | |
| 6,516,805 B1 | 2/2003 | Thornton | |
| 6,524,101 B1 | 2/2003 | Phan et al. | |
| 6,554,611 B2 | 4/2003 | Shishti et al. | |
| 6,572,372 B1 | 6/2003 | Phan et al. | |
| 6,604,527 B1* | 8/2003 | Palmisano | A61C 7/08 128/848 |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 6,749,414 B1 | 6/2004 | Hanson et al. | |
| 6,830,450 B2 | 12/2004 | Knopp et al. | |
| 7,226,287 B2 | 6/2007 | Abels et al. | |
| 7,293,987 B2 | 11/2007 | Abels et al. | |
| 7,357,637 B2 | 4/2008 | Leichtung et al. | |
| 7,637,262 B2 | 12/2009 | Bailey | |
| 7,892,474 B2 | 2/2011 | Shkolnik et al. | |
| 8,001,973 B2 | 8/2011 | Sotos et al. | |
| 8,025,063 B2 | 9/2011 | Sotos et al. | |
| 8,037,886 B2 | 10/2011 | Sotos et al. | |
| 8,215,312 B2 | 7/2012 | Garabadian et al. | |
| 8,297,286 B2 | 10/2012 | Smernoff | |
| 8,449,296 B2 | 5/2013 | Liechtung et al. | |
| 8,573,224 B2 | 11/2013 | Thornton | |
| 8,839,793 B2* | 9/2014 | Diaz | A61F 5/566 128/848 |
| 8,870,566 B2 | 10/2014 | Bergersen | |
| 9,545,331 B2 | 1/2017 | Ingemarsson-Matzen et al. | |
| 9,744,006 B2 | 8/2017 | Ross | |
| 9,844,424 B2 | 12/2017 | Wu et al. | |
| 1,029,989 A1 | 5/2019 | Tanugula et al. | |
| 2002/0006597 A1 | 1/2002 | Andreiko et al. | |
| 2003/0009252 A1 | 1/2003 | Pavlovskaia et al. | |
| 2003/0031976 A1* | 2/2003 | Clark | A61C 7/00 433/19 |
| 2003/0075186 A1* | 4/2003 | Florman | A61C 7/36 128/869 |
| 2003/0139834 A1 | 7/2003 | Nikolskiy et al. | |
| 2003/0207224 A1* | 11/2003 | Lotte | A61C 7/08 433/6 |
| 2003/0224311 A1 | 12/2003 | Cronauer | |
| 2003/0224313 A1 | 12/2003 | Bergersen | |
| 2004/0058295 A1 | 3/2004 | Bergersen | |
| 2004/0128010 A1 | 7/2004 | Pavlovskaia et al. | |
| 2004/0209218 A1 | 10/2004 | Chishti et al. | |
| 2005/0055118 A1 | 3/2005 | Nikolskiy et al. | |
| 2005/0136371 A1* | 6/2005 | Abolfathi | A61C 7/08 433/24 |
| 2005/0244781 A1 | 11/2005 | Abels et al. | |
| 2006/0008760 A1 | 1/2006 | Phan et al. | |
| 2006/0078840 A1 | 4/2006 | Robson | |
| 2006/0099546 A1 | 5/2006 | Bergersen | |
| 2008/0020337 A1 | 1/2008 | Phan et al. | |
| 2008/0057466 A1* | 3/2008 | Jordan | A61C 11/00 433/69 |
| 2008/0115791 A1 | 5/2008 | Heine | |
| 2009/0032030 A1 | 2/2009 | Callender et al. | |
| 2010/0138025 A1* | 6/2010 | Morton | A61C 7/00 700/104 |
| 2011/0005527 A1 | 1/2011 | McCance et al. | |
| 2011/0184762 A1* | 7/2011 | Chishti | A61C 7/00 705/3 |
| 2012/0295211 A1* | 11/2012 | Frantz | A61C 7/08 433/6 |
| 2013/0089828 A1* | 4/2013 | Borovinskih | A61C 7/08 433/6 |
| 2013/0122448 A1* | 5/2013 | Kitching | A61C 7/002 433/24 |
| 2013/0160776 A1* | 6/2013 | Petelle | A61C 7/36 128/848 |
| 2013/0204583 A1* | 8/2013 | Matov | A61C 7/002 703/1 |
| 2013/0297275 A1* | 11/2013 | Sanchez | A61C 7/002 703/11 |
| 2014/0061974 A1 | 3/2014 | Tyler et al. | |
| 2014/0142897 A1 | 5/2014 | Kuo | |
| 2014/0265034 A1 | 9/2014 | Dudley et al. | |
| 2014/0370465 A1* | 12/2014 | Lucas | A61C 7/36 433/214 |
| 2015/0097315 A1 | 4/2015 | Desimone et al. | |
| 2015/0097316 A1 | 4/2015 | Desimone et al. | |
| 2015/0102532 A1 | 4/2015 | Desimone et al. | |
| 2015/0238283 A1 | 8/2015 | Tanugula et al. | |
| 2015/0238284 A1 | 8/2015 | Wu et al. | |
| 2016/0106521 A1 | 4/2016 | Tanugula et al. | |
| 2016/0128803 A1 | 5/2016 | Webber et al. | |
| 2016/0361139 A1 | 12/2016 | Webber et al. | |
| 2017/0035533 A1 | 2/2017 | Ross | |
| 2018/0132975 A1 | 5/2018 | Wu et al. | |
| 2019/0125497 A1 | 5/2019 | Derakhshan et al. | |

FOREIGN PATENT DOCUMENTS

| | | |
|---|---|---|
| JP | 2011120928 A | 6/2011 |
| WO | 2001070126 | 9/2001 |
| WO | WO-02062252 A1 | 8/2002 |
| WO | 2012140021 | 10/2012 |
| WO | WO-2014060595 A1 | 4/2014 |

OTHER PUBLICATIONS

MicrO2.™ Sleep and Snore Devise, Easier for You and Youre Patients to Sleep Well, Microdental Dublin/CA Laboratory, 2 pp.

Resmed. Narvel CC—Gallery. Accessed from: http://www.resmed.com/int/products/narval_cc/image-gallery.html?nc=patients&sec=true on Sep. 19, 2014.

Sequim Smile The Family Denstry. Accessed from: http://www.sequimsmiles.com/snoring-sleep-apnea/ on Sep. 19, 2014.

The Moses. 3-Dimensional Oral Appliance. Accessed from: http://themoses.com/features/ on Sep. 19, 2014.

Respire Medical. Breathe Easy Again. The Respire Blue Series. Retrieved from: http://www.respiremedical.com/respire-blue-series.html on Sep. 19, 2014.

Somnomed. The leader in COAT. SomnoDent Product Information. Retrieved from:http://somnomed.com/dentists/somnodent-product-information/ on Sep. 19, 2014.

Zquiet Pro-Plus. For Patients. Retrieved from http://www.zquietproplus.com/patients.aspx on Sep. 19, 2014.

International Search Report and Written Opinion from related PCT Application No. PCT/IB2015/001655, dated Dec. 7, 2015, 14 pages.

"Anotherinvisalignblog. Invisalign Virtual Bite Ramps. Posted Jun. 17, 2012. 5 pages. Retrieved Aug. 14, 2013 from http://anotherinvisalignblog.wordpress.com/2012/06/17/invisalign-lingual-power-ridges-photos/.".

Bite Ramps. Align Orthodontics. Sep. 17, 2010. Retrieved on or before Sep. 19, 2014, from http://www.alignortho.com/Portals/0/pdf/BITE%20RAMPS.pdf.

Dr. Jonathan Nicozisis. Techniques for Deep Bite Correction with Invisalign. Clinical Tips & Techniques. Jun. 2012. http://www.princetonorthodontics.net/Portals/0/Nicozisis_DeepBiteCorrection_Invisalign_new0628.pdf.

Dr. William V. Gierie. Techniques for Deep Bite Correction with Invisalign Virtual Bite Ramps. Clinical Tips & Techniques. Jun. 2012.

"Leonardo Tavares Camardella, et al. Use of a Bite Ramp in Orthodontic Treatment. Apresentado no A.A.O.—Scientific Posters Exhibit N 41-7 de maio de 2006. http://www.cleber.com.br/leonardo/.".

(56) References Cited

OTHER PUBLICATIONS

International search report with written opinion dated Jan. 23, 2019 for PCT/US2018/058495.
"Mathematical Modeling Discussion of Optimal Design", vol. 25, No. 3, Journal of Jiangxi Vocational and Technical College of Electricity (2012) 4 pages.

* cited by examiner

320 ⤴

┌─────────────────────────────────────────────────────────────┐
│ MOVING AT LEAST ONE TOOTH WITH A DENTAL APPLIANCE HAVING A FIRST │
│ SHELL CONFIGURED TO RECEIVE A NUMBER OF TEETH OF A PATIENT'S ├─322
│ UPPER DENTITION, THE NUMBER OF TEETH COMPRISING THE AT LEAST │
│ ONE TOOTH │
└─────────────────────────────────────────────────────────────┘

┌─────────────────────────────────────────────────────────────┐
│ SEPARATING A PATIENT'S UPPER DENTITION FROM THE PATIENT'S LOWER ├─324
│ DENTITION UTILIZING THE DENTAL APPLIANCE │
└─────────────────────────────────────────────────────────────┘

┌─────────────────────────────────────────────────────────────┐
│ WHEREIN THE DENTAL APPLIANCE INTERFACES A FIRST │
│ SURFACE OF A FIRST REPOSITIONING JAW ELEMENT OF THE FIRST SHELL │
│ WITH A SECOND SURFACE OF A SECOND REPOSITIONING JAW ELEMENT OF │
│ A SECOND SHELL OF THE DENTAL APPLIANCE, THE SECOND SHELL │
│ CONFIGURED TO RECEIVE A NUMBER OF TEETH OF THE PATIENT'S LOWER ├─326
│ DENTITION, AND WHEREIN THE DENTAL APPLIANCE SEPARATES OCCLUSAL │
│ SURFACES OF THE NUMBER OF TEETH OF THE PATIENT'S UPPER │
│ DENTITION FROM OCCLUSAL SURFACES OF THE NUMBER OF TEETH OF │
│ THE PATIENT'S LOWER DENTITION AS THE PATIENT MOVES TO A │
│ FULLY ENGAGED SAGITTAL JAW POSITION │
└─────────────────────────────────────────────────────────────┘

Fig. 3

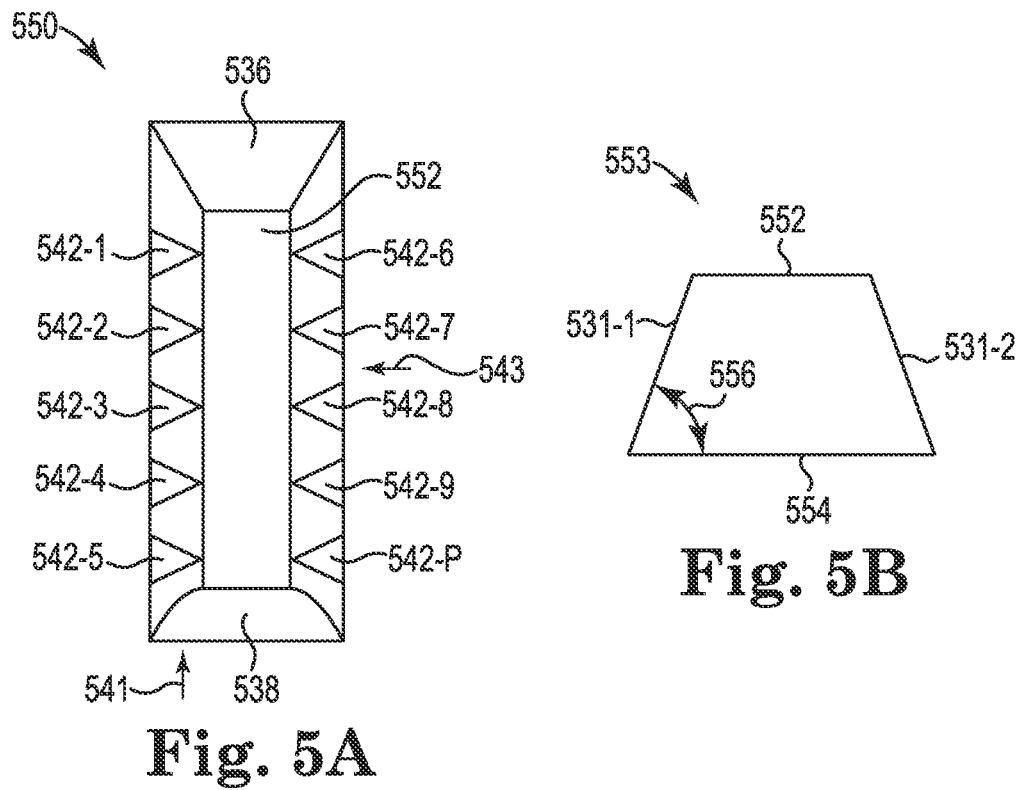
Fig. 5A
Fig. 5B
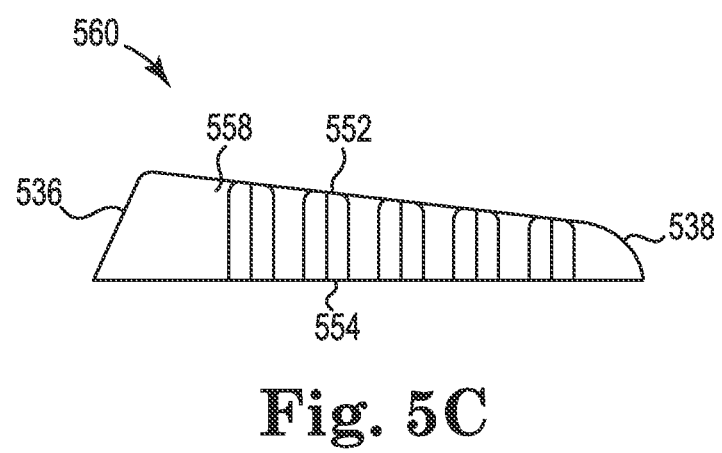
Fig. 5C

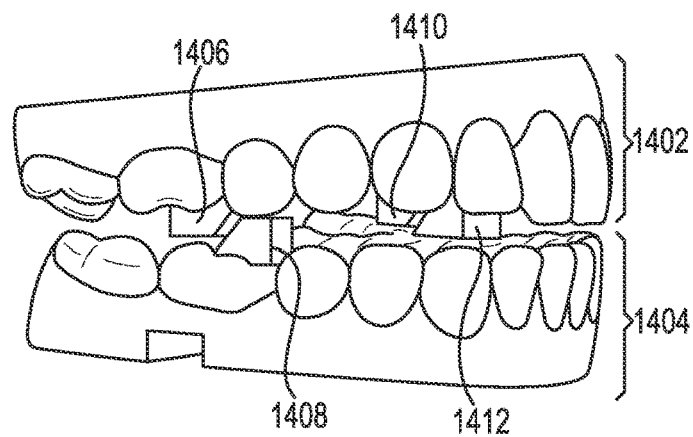
Fig. 14A
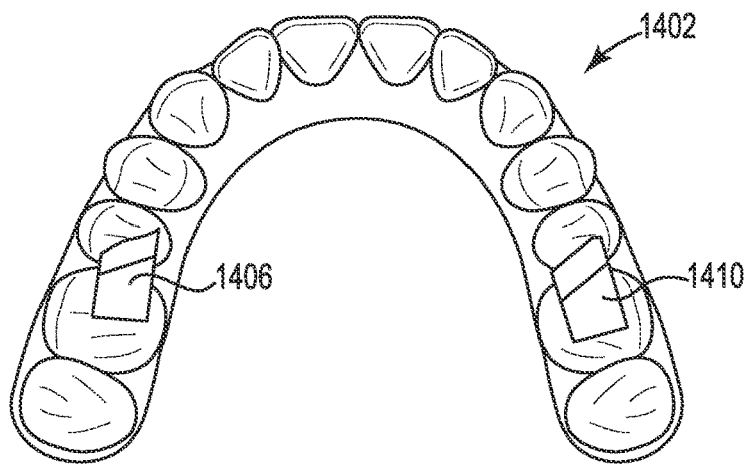
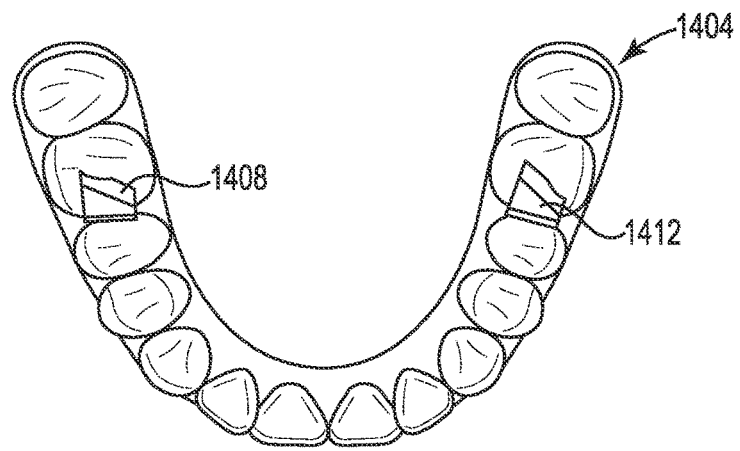
Fig. 14B

DENTAL APPLIANCE WITH REPOSITIONING JAW ELEMENTS

PRIORITY

The present application is a Continuation-in-Part of U.S. patent application Ser. No. 14/186,856, filed Feb. 21, 2014, now U.S. Pat. No. 9,844,424, issued Dec. 19, 2017, the entire contents of which are incorporated by reference.

BACKGROUND

The present disclosure is related generally to the field of dental treatment. More particularly, the present disclosure is related to methods, instructions on a computing device readable medium, and devices with repositioning jaw elements.

Dental treatments may involve, for instance, restorative and/or orthodontic procedures. Restorative procedures may be designed to implant a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a patient's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement (e.g., a corrected jaw position).

Such systems typically utilize materials that are light weight and/or transparent to provide as a set of appliances that can be used serially such that as the teeth move, a new appliance can be implemented to further move the teeth without having to take a new impression of the patient's teeth at every increment of tooth movement in order to make the successive appliance.

In various instances, teeth of a patient's upper jaw and teeth of the patient's lower jaw may contact in an incorrect or suboptimal manner (e.g., crowding, crossbite, deep bite). A proper fit of the occlusal surfaces of the teeth is necessary for proper biting and chewing, as well as desirable for aesthetic appearance. Otherwise, premature wear of the teeth, undesirable flexion of the teeth, and/or undesirable forces on dental restorations may be experienced by the patient. For instance, a proper fit can be a function of the relative positions of teeth and the mandible and maxilla, either of which may be retruded or protruded relative to the ideal position. The maxilla (e.g., the upper jaw) is a bone that is fixed to the skull. The mandible (e.g., lower jaw) is a bone that is attached to the skull by numerous muscles which guide its movement. The mandible articulates at its posterior upward extremities with the temporal bone to form the jaw joint. The jaw joint is a loosely connected joint that accommodates the variety of movements of the mandible relative to the maxilla during biting and chewing motions. The numerous muscles attaching the mandible to the skull control and power the complex movements involved in biting and chewing.

The position of the lower jaw is governed by at least two factors. The first factor is the best fit or seating of the condyles of the mandible within the joint housing of the temporal bone. The posterior superior most position of the condyle in the joint is usually an ideal position representing full seating. The second factor is the best fit of the teeth between the maxilla and the mandible. Ideally, the teeth fit together best in occlusion with the left and right jaw joint fully seated at the same time, but this is not a requirement. Sometimes, the teeth fit together best with the condyles slightly displaced from the joint. As a result, when the condyles are fully seated, the teeth may not be in their best fitting position. This condition is known as a shift between the centric relationship (condyles fully seated) and the centric occlusion (teeth best fitting).

Because the condylar relationship affords some flexibility in the positioning of the jaw, the lower jaw can be intentionally repositioned in accordance with the best fit of the teeth, for instance, by using an orthodontic appliance. The orthodontic appliance used may or may not be displeasing, both physically and aesthetically, to a patient undergoing treatment which intentionally repositions the lower jaw.

BRIEF DESCRIPTION OF THE DRAWINGS

FIG. 3 illustrates an example of a method for separating an upper dentition from a lower dentition according to a number of embodiments of the present disclosure.

FIGS. 5A-5C illustrate examples of repositioning jaw elements according to a number of embodiments of the present disclosure.

FIGS. 14A-14B illustrate examples of repositioning jaw elements for adjusting a midline of a patient according to a number of embodiments of the present disclosure.

DETAILED DESCRIPTION

Figure 1A:
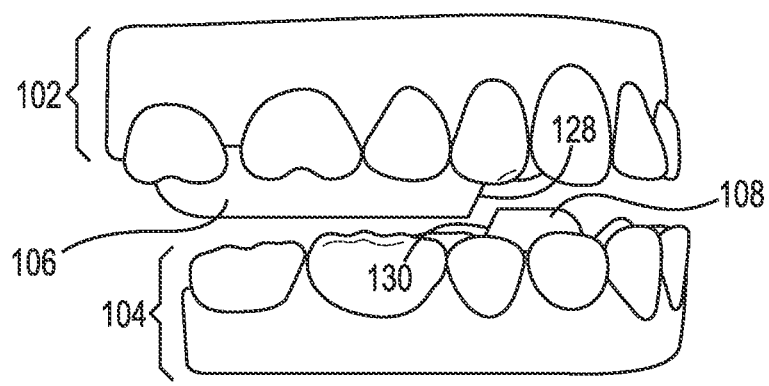
FIG. 1A illustrates a side view of an upper jaw with a first repositioning jaw element and a lower jaw with a repositioning jaw element according to a number of embodiments of the present disclosure.

As discussed above, the present disclosure provides methods, instructions on computing device readable medium, and devices for repositioning jaw elements. Generally, the repositioning occurs during an orthodontic treatment which is a process of moving and reorienting teeth for functional and/or aesthetic purposes, although repositioning may be made for other purposes.

Simultaneous contacting of the upper and lower teeth on the right and left sides, and in the anterior and posterior occlusal areas with maximum interdigitation is desired for proper positioning of the lower jaw to the upper jaw in the mouth of a patient. An unbalanced occlusion, such as a malocclusion, is disruptive to the proper biting and chewing functions because excessive forces may be placed in a particular area that can lead to premature wear and/or restoration failure, or because undesirable forces such as flexion may lead to stresses which cause abfraction lesions and/or crowding/spacing of the teeth. The position of a patient's jaw can be changed, for instance, using an orthodontic appliance (e.g., a dental appliance).

Current approaches for jaw repositioning, such as those performed prior to fixed orthodontic treatment (i.e., "braces") include having a treatment professional place an orthodontic appliance which may include block elements, wires, tensioning springs, horizontal stops, etc., which is firmly fixed to the teeth and which applies repositioning forces to move the jaw of the patient, thereby causing the relative positioning of the patient's upper and lower jaws to adjust. Some believe that this repositioning stimulates jaw growth in patients with growth potential remaining, while others believe that the muscles can re-learn a new position so long as the teeth are made to fit together well in the new jaw position. In some instances, prior approaches include a removable appliance with block elements.

Current appliances for jaw repositioning are not designed to reposition the teeth during the process of jaw repositioning. After adjustment of the position of the patient's jaw, further orthodontic treatment is performed to move and re-orientate the teeth of the patient for improved dental interdigitation, if necessary. Many of the current jaw repositioning devices can be displeasing to patients, both physically and aesthetically, because the patient does not have the option to remove the appliance even for a short period of time. Such appliances (e.g., Herbst appliance) are typically cemented into place on the patient's teeth. Depending on whether the jaw change is due to growth or muscular repositioning, realigning the teeth of a patient after repositioning the jaw can result in reversion of the position of the jaw if the teeth are not positioned and/or repositioned in a manner that best supports the new jaw position. This would occur, for example, if the teeth fit better in a jaw position different from the one which is accomplished through the jaw repositioning phase of the treatment. In this situation, the jaw would revert toward its original position or whatever position is most comfortable for the patient when biting since the jaw repositioning appliance has been removed. Therefore, the desire is to reposition the jaw to an optimal relation while at the same time arrange the teeth such that they fit together the best both in arch coordination between the upper and lower arches and in interdigitation between the arches. The interdigitation makes the patient more likely to keep the lower jaw in the new position since the teeth fit together the best in the interdigitated position.

Repositioning a jaw (e.g., separation of occlusal surfaces and/or moving forward or backward the position of a lower jaw) according to embodiments of the present disclosure can include utilizing a set of one or more appliances, such as positioners, retainers, and/or other removable appliances (e.g., clear shells and/or aligners) having a shell to be worn over the teeth of a patient and having a first repositioning jaw element thereon that is positioned to interface, interact, and/or engage a second repositioning jaw element on an appliance on an opposing jaw for separating occlusal surfaces of the patient's upper dentition and lower dentition and/or to reposition the patient's jaw. The repositioning jaw elements can place a force on the lower jaw of the patient to sagittally move the lower jaw. Sagittal movement of a jaw, as used herein, can include revising a position of a lower jaw relative to the upper jaw (e.g., in a forward or backward direction). For instance, the position of the patient's lower jaw can shift sagittally to stimulate jaw growth in patients with growth potential remaining and/or to allow muscles to re-learn a new position.

In various embodiments, the movement can be controlled to reposition the patient's jaw in an anterior-posterior plane with respect to the jaws of the patient. For example, the first repositioning jaw element and the second repositioning jaw element can be positioned to interface as the patient moves to a fully engaged sagittal jaw position of the patient's upper dentition and the patient's lower dentition and wherein this movement is designed to reposition the patient's jaw in an anterior-posterior plane with respect to the jaws of the patient.

For example, one or more embodiments can include providing a virtual model of a dental appliance having a shell configured to reposition a number of teeth of a patient. The virtual model of the dental appliance can, for instance, be created from a virtual model of the jaw of the patient and/or from a physical mold of the jaw of the patient. A virtual repositioning jaw element can, for example, be positioned on the shell of the virtual model of the dental appliance parallel to a bite plane of the patient and/or can extend from a surface of the shell of the virtual model of the dental appliance. The positioning of the virtual repositioning jaw element and/or the design of the virtual repositioning jaw element can be based on and/or included in a treatment plan. For instance, the treatment plan can include a desired, ideal, and/or final jaw position. The virtual model of the dental appliance with the revised position of the repositioning jaw element can be used to create a physical dental appliance, for instance, as discussed further herein.

A dental appliance, in accordance with some embodiments of the present disclosure, can include a first shell having a number of tooth apertures configured to receive and reposition a number of teeth of a patient's upper dentition and a second shell having a number of tooth apertures configured to receive and reposition a number of teeth of the patient's lower dentition. Each shell (e.g., the first shell and second shell) can have a repositioning jaw element extending from a surface of the shells. The repositioning jaw elements can be positioned in each respective shell to interact and/or interface at surfaces in the presence of a fully engaged sagittal jaw position of the patient's upper jaw and the patient's lower jaw in order to reposition the patient's jaw and/or separate occlusal surfaces of the patient's teeth for treatment purposes. A fully engaged sagittal jaw position, as used herein, can include a relationship of the mandible and the maxilla when the upper and lower jaw are closed as far as the dental appliance with the repositioning jaw elements will allow (e.g., a partial occlusal jaw position).

For example, the separation of occlusal surfaces of the patient's teeth can be used to treat sagittal malocclusions (including crossbites), deep bites, open bites, and/or other malocclusions, in various embodiments. The repositioning jaw elements can be positioned such that the repositioning jaw elements avoid interference with the shells of the dental appliance that are used to align the teeth. For instance, the separation of occlusal surfaces can include the occlusal surfaces of at least some of the teeth within and/or a portion of occlusal surfaces of the shells interacting with one or more surfaces of the repositioning jaw elements of a shell on an opposing jaw. In this manner, a dental appliance in accordance with embodiments of the present disclosure can be used to concurrently treat sagittal malocclusions, including crossbite and/or deep bite, while simultaneously repositioning a number of teeth of the patient. Further, in some embodiments, all of this tooth and jaw movement can be planned via computing device executable instructions and therefore, excessive or redundant movements between the two typically separate processes can be avoided. Additionally, a virtual model can be created and tested so that the patient does not have to be subjected to trial and error to achieve proper jaw and teeth positioning. The ability to visualize the repositioned jaws and establish the alignment in the repositioned configuration is advantageous because the best alignment of the teeth when the jaw is repositioned can be precisely established and can be different from the alignment when the jaws are not repositioned into an improved or optimal position.

In some embodiments, a plurality of appliances can be worn by a patient successively to achieve gradual simultaneous and/or sequential repositioning of the patient's jaw and/or gradual tooth movement. For instance, each of a plurality of dental appliance can reposition the patient's jaw in incremental distances. In such embodiments, the positions of the repositioning jaw elements can be adjusted to allow the treatment professional to fine tune the movement of the jaw symmetrically or asymmetrically and/or to move the teeth incrementally which may be less painful than with fixed appliances which may impart more sudden force in the initial period of the process than later in the process, among other benefits.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, the designator "N" and "P", particularly with respect to reference numerals in the drawings, indicates that a number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1, and a similar element may be referenced as 206 in FIG. 2. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

FIG. 1A illustrates a side view of an upper jaw 102 with a first repositioning jaw element 106 and a lower jaw 104 with a second repositioning jaw element 108 according to a number of embodiments of the present disclosure. The upper jaw 102, the first repositioning jaw element 106, the lower jaw 104, and the second repositioning jaw element 108 illustrated in FIG. 1A include virtual images of jaws and repositioning jaw elements, respectively (e.g., virtual jaws and/or virtual repositioning jaw elements), as discussed further herein. The upper jaw 102 can include a maxilla, its related soft and hard tissues, and can include a number of teeth of a patient's upper dentition. The lower jaw 104 can include a mandible, its related soft and hard tissues, and can include a number of teeth of the patient's lower dentition.

In some instances, the patient may exhibit abnormal occlusion or malocclusion. For instance, this may include a jaw (or both) that is protrusive, retrusive, or laterally displaced. As an example, positioning of the number of teeth of the patient's upper dentition and the number of teeth of the patient's lower dentition can be such that the best fit of the upper dentition with the lower dentition results in a misalignment of the lower jaw 104 relative to the upper jaw 102 either in positional relations or at the level of the jaw joint which connects the lower jaw 104 to the upper jaw 102. The lower jaw 104 can be in a retruded position, for instance, resulting in a distance (e.g., space) between the front teeth of the upper dentition and the front teeth of the lower dentition (e.g., an increased overjet). Correction of the malocclusion can be beneficial to the patient in terms of improved chewing ability, reduced premature wear of the teeth, and/or improved facial aesthetics.

In some embodiments, the upper jaw 102 and lower jaw 104 illustrated in FIG. 1A can include a virtual model of the patient's upper jaw and lower jaw. A virtual model of one or more dental appliances (e.g., an appliance for the upper dentition and an appliance for the lower dentition which may also be connected together) each having a shell configured to reposition a number of teeth of the patient can be provided. The virtual model of the dental appliance can include a virtual model of a dental appliance configured to reposition the number of teeth of the patient.

Repositioning jaw elements can be positioned on occlusal, buccal, and/or lingual surfaces of a dental appliance to be placed over the patient's teeth. A repositioning jaw element, as used herein, can include a portion of material (e.g., a geometric shaped element, such as a block shape) extending from a surface of the shell of the appliance, as discussed further herein. For instance, a virtual repositioning jaw element can be positioned on the shell of the virtual model of the dental appliance parallel to an occlusal plane of the patient. An occlusal plane, as used herein, can include a surface from the incisal edges of the incisors and the tips of the occluding surfaces of the posterior teeth that is a mean of the curvature of the surface.

In some embodiments, the position of the virtual repositioning jaw element can be revised to align with a midline (e.g., middle) of at least one tooth of the number of teeth wherein the virtual repositioning jaw element extends from a surface of the shell of the virtual model of the dental appliance. However, embodiments in accordance with the present disclosure are not so limited and the virtual repositioning jaw elements may not be aligned with a midline of the at least one tooth in various embodiments. The virtual model of the dental appliance, including the virtual repositioning jaw element, can be used to determine a treatment plan for the patient and/or to form a physical dental appliance and/or physical repositioning jaw element (e.g., as discussed further herein).

The physical repositioning jaw element can be formed of a variety of material types. In some embodiments, the physical repositioning jaw element can be formed of the same material as the shell of the dental appliance (e.g., a polymeric material). For instance, the physical repositioning jaw element can be formed integrally with the shell and/or formed of a same material as the shell.

The repositioning jaw elements can also be positioned in different places, in some embodiments. For example, the first repositioning jaw element 106 and the second repositioning jaw element 108 can be positioned near occlusal surfaces of the teeth of the patient to advance the placement of the lower jaw 104 in a forward direction (e.g., in an anterior direction and/or toward a patient's lips) or in a backward direction (e.g., in an posterior direction and/or towards the back of the patient's head). For instance, occlusal surfaces of teeth of the upper jaw 102 and lower jaw 104 can be separated using the first repositioning jaw element 106 and the second repositioning jaw element 108 to move (e.g., to move sagittally) the lower jaw 104 of the patient from an articulation path during opening (e.g., the path that the jaw currently follows when opening) to a desired range of jaw opening extending from an advanced or forward position of occlusion, as described further herein. As an example, the first repositioning jaw element 106 can include a first surface 128 and the second repositioning jaw element 108 can include a second surface 130 to interface, interact, and/or otherwise engage with the first surface 128 of the first repositioning jaw element 106, as discussed further herein. By moving the lower jaw 104, muscles associated with movement of the lower jaw 104 can be retrained to a new position (generally in a forward and/or downward direction, or in a backward direction) or the lower jaw may be permitted to grow more fully if the patient has not fully developed skeletally.

Figure 1B:
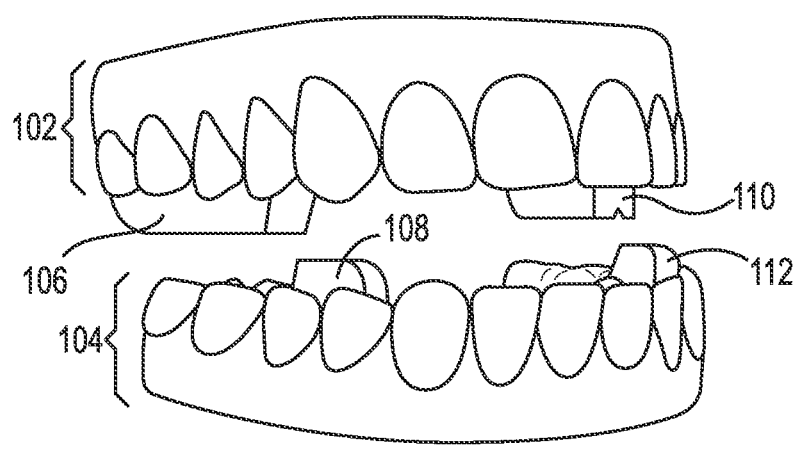
FIG. 1B illustrates a front view of an upper jaw with a first repositioning jaw element and a third repositioning jaw element and a lower jaw with a second repositioning jaw element and a fourth repositioning jaw element according to a number of embodiments of the present disclosure.

FIG. 1B illustrates a front view of an upper jaw 102 with a first repositioning jaw element 106 and a third repositioning jaw element 110 and a lower jaw 104 with a second repositioning jaw element 108 and a fourth repositioning jaw element 112 according to a number of embodiments of the present disclosure. A front view, as used herein, can include an anterior view and/or a more anterior view of the jaws as compared to a side view. The upper jaw 102, the first repositioning jaw element 106, the third repositioning jaw element 110, the lower jaw 104, the second repositioning jaw element 108, and the fourth repositioning jaw element 112 illustrated in FIG. 1B can include virtual images of jaws and repositioning jaw elements, respectively (e.g., virtual jaws and/or virtual repositioning jaw elements), as discussed further herein. As illustrated by FIG. 1B, two repositioning jaw elements (e.g., the first repositioning jaw element 106 and the third repositioning jaw element 110) can be positioned near (e.g., adjacent to) occlusal surfaces of the upper jaw 102 and two repositioning jaw elements (e.g., the second repositioning jaw element 108 and the fourth repositioning jaw element 112) can be positioned near occlusal surfaces of the lower jaw 104.

The first repositioning jaw element 106 can be positioned near the occlusal surfaces of the posterior teeth (in the embodiment illustrated by FIG. 1B, the molars and/or bicuspids) of the upper jaw 102 and the second repositioning element 108 can be positioned near the occlusal surfaces of the posterior teeth (in the embodiment illustrated by FIG. 1B, the bicuspids) of the lower jaw 104. The first repositioning jaw element 106 and second repositioning jaw element 108 can be located near a first posterior side of the patient's dentition.

The first repositioning jaw element 106 and the second repositioning jaw element 108 can include surfaces that can interface, interact, and/or engage with a surface of a repositioning jaw element on a shell of an opposing jaw. For instance, a first surface of the first repositioning jaw element 106 can interface, interact, and/or engage with a second surface of the second repositioning jaw element 108. A surface, as used herein, can include a side and/or end surface of a repositioning jaw element. In some embodiments, the first surface can include a slanted surface on a mesial-facing surface of the first repositioning jaw element 106 and/or the second surface can include a slanted surface on a distal-facing surface of the second repositioning jaw element 108, for instance. For example, a mesial-facing surface can include a surface of a repositioning jaw element that is in a direction toward the anterior midline of the teeth. A distal-facing surface can include a surface of a repositioning jaw element that is in a direction toward the last tooth in each quadrant of a dental arch. However, embodiments in accordance with the present disclosure are not so limited. A mesial-facing surface, in some embodiments, can be facing toward the facial plane (e.g., normal to the facial plane), whereas a distal-facing surface can be facing away from the facial plane (e.g., normal to the facial plane but in the opposite direction). The surfaces of the repositioning jaw elements, in accordance with embodiments of the present disclosure, can be oriented in a variety of directions.

The third repositioning jaw element 110 can be positioned near the occlusal surfaces of the posterior teeth (in embodiment illustrated by FIG. 1B, molars and/or bicuspids) of the upper jaw 102 and the fourth repositioning jaw element 112 can be positioned near the occlusal surfaces of the posterior teeth (in the embodiment illustrated by FIG. 1B, bicuspids) of the lower jaw 104. The third repositioning jaw element 110 and the fourth repositioning jaw element 112 can be located near a second posterior side of the patient's dentition. The third repositioning jaw element 110 and the fourth repositioning jaw element 112 can include surfaces that can interface, interact, and/or engage with a surface of a repositioning jaw element on an opposite jaw. For instance, a third surface of the third repositioning jaw element 110 can interface, interact, and/or engage with a fourth surface of the fourth repositioning jaw element 112. The third surface can include a slanted surface on a mesial-facing surface of the third repositioning jaw element 110 and the fourth surface can include a slanted surface on a distal-facing surface of the fourth repositioning jaw element 112, for instance.

However, embodiments in accordance with the present disclosure are not so limited. For instance, the surfaces of the repositioning jaw elements 106, 108, 110, 112 can be oriented in a variety of directions. For instance, the first surface of the first repositioning jaw element 106 and the third surface of the third repositioning jaw element 110 can include distal-facing slanted surfaces and/or the second surface of the second repositioning jaw element 108 and the fourth surface of the fourth repositioning jaw element 112 can include mesial-facing slanted surfaces, among other orientations.

The surfaces (e.g., that interact and/or interface) of the repositioning jaw elements 106, 108, 110, 112 can be angled, in various embodiments, to guide the lower jaw 104 into position and gain desired lateral or prevent unwanted lateral movement. The surfaces can be angled in buccal-lingual and/or mesial-distal direction, for example. The angle of interacting and/or interfacing surfaces (e.g., two surfaces that are designed to interface, interact, and/or engage with each other either actively or passively) can have the same degree and/or slant or a different degree and/or slant (e.g., as illustrated by the embodiment of FIGS. 14A-14B).

For example, the first surface of the first repositioning jaw element 106 and the second surface of the second repositioning jaw element 108 can interface at a first slant. The slant can include, for instance, a degree of angle of the repositioning jaw elements. The third surface of the third repositioning jaw element 110 and the fourth surface of the fourth repositioning jaw element 112 can interface at a second slant.

The first slant and the second slant, in accordance with a number of embodiments, can include opposing angles. The opposing angles of slants on opposing posterior sides of the patient's dentition can facilitate desired lateral movement or limit and/or prevent unwanted lateral movement. In some embodiments, the sum of the opposing angles can include 180 degrees. As an example, if the first slant is 70 degrees then the second slant can include 110 degrees.

In accordance with some embodiments, the repositioning jaw elements 106, 108, 110, 112 extending from surfaces of a shell can be used to generate distalizing force on at least some of the teeth that are located within the shell. For example, when the repositioning jaw elements 106, 108, 110, 112 interface, the distalizing forces can be isolated to posterior teeth of the upper jaw. The distalizing forces can, in some embodiments, cause tooth movement of the upper jaw posterior teeth in a distal direction. As such, the repositioning jaw elements 106, 108, 110, 112 in various embodiments can be a substitute for Class II elastics.

Figure 8A:
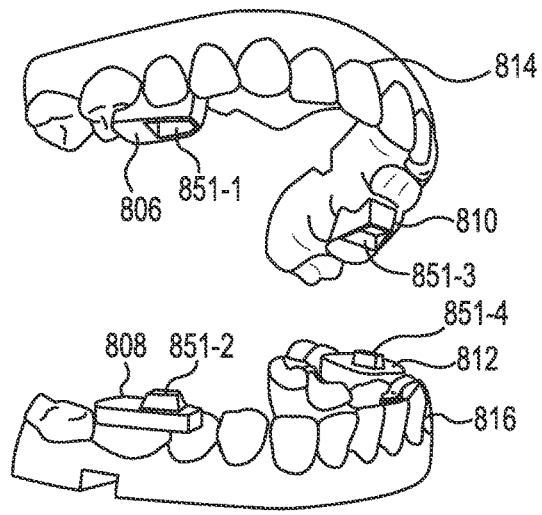
FIGS. 8A-8D illustrate examples of repositioning jaw elements according to a number of embodiments of the present disclosure.

In some embodiments, the repositioning jaw elements 106, 108, 110, 112 can include geometric features to engage with a repositioning jaw element on an opposing jaw. Geometric features, as used herein, can include a variety of protruding geometric shapes (e.g., cylinder, rectangular, etc.) and/or receding geometric shapes (e.g., negative space that matches the protruding geometric shape on a repositioning jaw element on an opposing jaw, as illustrated in the embodiment of FIG. 8A). For example, a geometric feature on the first surface of the first repositioning jaw element 106 can include a convex cylindrical shaped feature and a geometric feature on the second surface of the second repositioning jaw element 108 can include a concave cylindrical shaped feature shaped to mate with the geometric feature on the first surface of the first repositioning jaw element 106.

In some embodiments, the geometric features of a first repositioning jaw element and/or a second repositioning jaw element can include a protrusion and a socket. A socket, in various embodiments, can include a convex geometric shape that is shaped to mate with a geometric shape on an opposing jaw (e.g., as discussed further herein). For example, a first repositioning jaw element can include a protrusion extending from the first repositioning jaw element in a direction toward occlusal surfaces of the opposing jaw. The second repositioning jaw element can include a socket within the second repositioning jaw element. The protrusion of the first repositioning jaw element can fit into the socket of the second repositioning jaw element to assist in guiding the lower jaw into a forward position or a backward position.

Alternatively, the protrusion and/or socket can be located within and/or extend from a surface of the shell. In some instances, one or more sockets can be located within and/or extend from a surface of the first shell located behind anterior teeth of the upper jaw. In such an embodiment, the lower incisor teeth can fit into the one or more sockets to guide the lower jaw into a forward position or backward position.

Although the present embodiments discuss guiding a jaw into a forward position or backward position, embodiments in accordance with the present disclosure are not so limited. For example, embodiments in accordance with the present disclosure can include guiding a jaw in a variety of directions, such as a mesial-distal direction, as discussed further herein with regards to the embodiment illustrated in FIGS. 14A-14B.

Figure 1C:
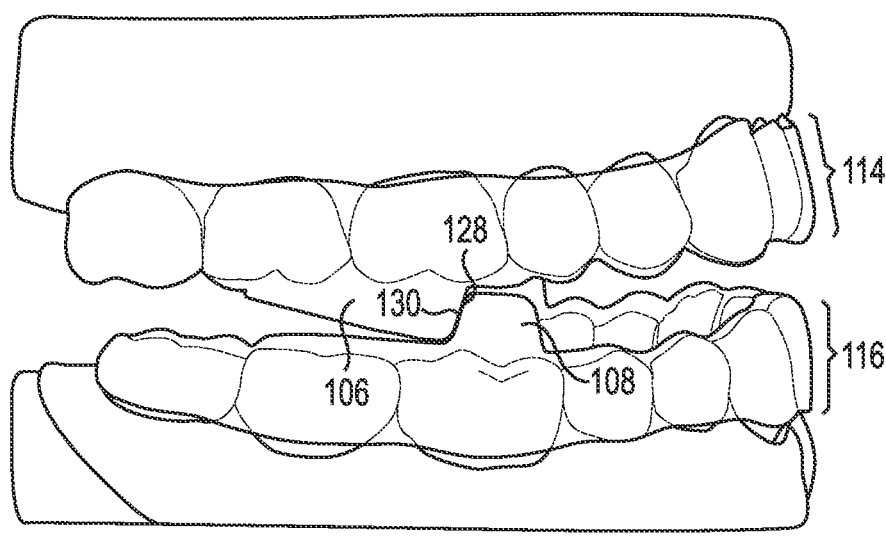
FIG. 1C illustrates a side view of a first shell with a first repositioning jaw element and a second shell with a second repositioning jaw element according to a number of embodiments of the present disclosure.

FIG. 1C illustrates a side view of a first shell 114 with a first repositioning jaw element 106 and a second shell 116 with a second repositioning jaw element 108 according to a number of embodiments of the present disclosure. The side view can, for instance, include a profile view of the first shell 114 and the second shell 116. The first shell 114 and the second shell 116, in some embodiments, can include a removable dental appliance.

Appliances can include any positioners, retainers, and/or other removable dental appliances for finishing, inducing (e.g., causing small movements in teeth), or maintaining teeth position in connection with a dental treatment. These appliances may be utilized by the treatment professional in completing a treatment plan. For example, a treatment plan can include the use of a set of dental appliances, created according to models described herein.

An appliance can, for example, be fabricated from a polymeric shell, and/or formed from other material, having a number of cavities shaped (e.g. tooth apertures) to receive and apply force to reposition one or more teeth from one geometric tooth arrangement to one or more successive tooth arrangements. There may be several appliances that may be needed to move the teeth from the beginning of a dental treatment plan to the end of the plan. The shell may be designed to fit over a number of, or in many instances all, teeth present in the upper and/or lower jaw. For example, a shell can have a cavity that includes a number of tooth apertures for placement of teeth therein. Each tooth aperture can include an interior surface (e.g., directly adjacent to the surfaces of the teeth placed therein) and an exterior surface. The interior surface is configured to receive and reposition a number of teeth of the patient, for example.

The first shell 114 can include a number of tooth apertures configured to receive and reposition a number of teeth of a patient's upper dentition. As illustrated by FIG. 1C, a first repositioning jaw element 106 can extend from a surface of the first shell 114. The first repositioning jaw element 106 can extend from an occlusal surface of the first shell 114. An occlusal surface of a shell, as used herein, can include an exterior surface of the shell adjacent to and/or extending toward the occlusal surfaces of the teeth on an opposing jaw of the patient.

The second shell 116 can include a number of tooth apertures configured to receive and reposition a number of teeth of the patient's lower dentition. A second repositioning jaw element 108 can extend from a surface of the second shell 116. For instance, the second repositioning jaw element 108 can extend from an occlusal surface of the second shell 116.

As illustrated by FIG. 1C, a shell with a repositioning jaw element, such as the first shell 114 with the first repositioning jaw element 106 and the second shell 116 with the second repositioning jaw element 108, include continuous dental appliances that contain geometries (e.g., the repositioning jaw elements) that act as repositioning jaw elements. That is, the repositioning jaw elements 106, 108 are geometries of the shells 114, 116, and not separate elements attached thereto.

The first repositioning jaw element 106 can include a first surface 128 and the second repositioning jaw element 108 can include a second surface 130 to interface with the first surface 128 of the first repositioning jaw element 106. For example, as illustrated by the embodiment of FIG. 1C, the first repositioning jaw element 106 and the second repositioning jaw element 108 can be positioned to interface, interact, and/or otherwise engage in the presence of a fully engaged sagittal jaw position of the patient's upper dentition (e.g., the upper jaw 102 illustrated in FIGS. 1A-1B) and the patient's lower dentition (e.g., the lower jaw 104 illustrated in FIGS. 1A-1B) in a manner to reposition the patient's lower jaw. The reposition of the patient's lower jaw can, for instance, include moving (e.g., moving sagittally) a lower jaw of the patient from an existing articulation reflex path of opening to a desired more extended range of jaw opening whereby the lower jaw is moved forward or backward into a new sagittal jaw position.

Alternatively and/or in addition, the repositioning of the patient's jaw can include a separation of occlusal surfaces of the number of teeth of the patient's upper dentition from occlusal surfaces of the number of teeth of the patient's lower dentition as the patient moves to a fully engaged sagittal jaw position. For instance, separating occlusal surfaces can include separating occlusal surfaces to a threshold distance to prevent an occlusal surface of the first shell 114 from contacting or engaging an occlusal surface of the second shell 116. The threshold distance can include a particular value. For example, the threshold distance can include one millimeter or less, among other values. As discussed above, the separation of occlusal surfaces can include the occlusal surfaces of at least some of the teeth within a shell and/or at least some of an occlusal surface of the shell contacting or engaging with one or more surfaces of the repositioning jaw element of a shell on an opposing jaw.

As illustrated by FIG. 1C, the first repositioning jaw element 106 can include a slanted top surface. For example, a slanted top surface can include a slant in height from the first surface 128 to the back surface of the first repositioning jaw element 106 (e.g., back surface 538 as illustrated by FIG. 5C).

Further, the first surface 128 of the first repositioning jaw element 106 and the second surface 130 of the second repositioning jaw element 108 can include a slant, as further described herein. For example, as illustrated by FIG. 1C and further illustrated by FIG. 4A, the first surface 128 can be a slanted mesial-facing surface of the first repositioning jaw element 106 and the second surface 130 can be a slanted distal-facing surface of the second repositioning jaw element 108. The surfaces 128, 130 can interface at the slant (e.g., the angled surfaces), for instance.

The combination of the slanted top surface of the first repositioning jaw element 106, the slant of the first surface 128, and/or the second surface 130 can, for instance, allow for error in predicting the corrected jaw position of the patient when designing the first shell 114 and the second shell 116. For example, the first shell 114 and the second shell 116 can be designed for a predicted corrected jaw position that is different from an actual corrected jaw position of the patient (e.g., the predicted corrected jaw position may be inaccurate as compared to the actual corrected jaw position of the patient).

A corrected jaw position can, for example, be a relation of the upper jaw and the lower jaw that is a corrected (e.g., changed) as compared to a current jaw position of the patient. For example, a corrected jaw position can include an optimal relation of the upper jaw and the lower jaw (e.g., an ideal jaw position), a more optimal relation of the upper and lower jaw than the current jaw position, and/or an overcorrected position (e.g., lower jaw can protrude forward more than an optimal relation/an advanced jaw position). For example, in some embodiments, the corrected jaw position can be an incremental movement toward the optimal relation of the upper jaw and the lower jaw.

The first shell 114 and second shell 116 may be designed for an inaccurate predicted corrected jaw position. However, due to the slanted top surface of the first repositioning jaw element 106 and the slant of the first and second surfaces 128, 130, the first and second repositioning jaw elements 106, 108 can have an ideal fit when worn by the patient.

An ideal fit, as used herein, is a fit of the repositioning jaw elements when the patient's jaw is closed. For example, an ideal fit can be a position and fit of the repositioning jaw elements that can reposition the patient's jaw toward a corrected jaw position. A corrected jaw position can be predicted using patient data. However, the predicted corrected jaw position may not always be accurate due to limited patient data available.

In a number of embodiments, the patient data can include articulation information. For example, articulation information of a patient can be input using a scanned bite registration with the patient biting into a soft wax in an advanced position and matching the scan to fit the scanned bite registration. An advanced position, as used here, can include a forward position of the lower jaw relative to the upper jaw. Alternatively, an articulator and a facebow transfer can be used to create articulated models and the articulated position can be input to a computing device. That is, a scan of the actual bite or of a mounted articulation of the bite can be input and used to design (e.g., position) the repositioning jaw elements.

The ideal fit of the repositioning jaw elements can take into account potential errors in predicting the corrected jaw position and/or variations in jaw relation of the patient due to movement of the jaw from a fully closed position. For example, a patient's jaw may not always be positioned in a fully closed position. Design of the repositioning jaw elements, in accordance with the present disclosure, can allow for a corrected jaw position to be incorrectly predicted and/or for the relation of the patient's jaw to move and still separate the jaw an intended height and/or toward an intended position.

That is, the repositioning jaw elements 106, 108 can separate the jaws an intended height and/or move the jaw toward an intended position even with an inaccurate predicted corrected jaw position. A dental appliance without the slanted top surface and/or slant of the first and second surfaces that is designed for an inaccurate predicted corrected jaw position can separate the jaws a greater (or lesser) height than the intended height and/or move the jaw past (or less than) the intended position.

In some embodiments, the separation of occlusal surfaces can be used for treatment of sagittal malocclusion, including excess overjets and anterior crossbite, the correction of transverse malocclusions including lateral crossbites, and/or vertical problems such as deep bite. Malocclusions can be treated using the repositioning jaw elements 106, 108 (in addition to a third repositioning jaw element 110 and fourth repositioning jaw element 112 on the opposing posterior side of the jaw, in some embodiments, as illustrated by the embodiment of FIG. 1B) to reposition the jaw of the patient. In some situations, such as anterior crossbite and deep bite can be treated using the repositioning jaw elements 106, 108 to allow for individual movement of teeth while the jaws are repositioned into a new relative relationship.

Patients with crossbites and/or deep bites can have anterior incisors in the upper jaw and/or the lower jaw that are difficult to move into the desired location because teeth in the opposing jaw are a physical obstruction and therefore can prevent the desired movement from taking place, in some instances. The repositioning jaw elements 106, 108 can provide separation of the upper jaw from the lower jaw (e.g., disclusion) by separating an occlusal surface of the first shell 114 from an occlusal surface of the second shell 116. In various instances, the repositioning jaw elements 106, 108 used for the treatment of crossbites and deep bites can be the same buccal-lingual length and can extend from an occlusal, lingual, and/or buccal surface of the first shell 114 and the second shell 116.

The repositioning jaw element 106, 108 can be positioned near posterior teeth, for instance, to allow for an anterior portion of the bite of the patient to open enough (e.g., disengage the occlusal interferences that may normally take place) to allow for easier treatment of the crossbite and/or deep bite. For instance, the separation of occlusal surfaces can be caused by preventing the cusp of the molars from sliding back into the fossae on the opposing molars. In such situations, the upper jaw and the lower jaw are held apart and avoid interfering with the prescribed treatment, for example.

In accordance with a number of embodiments of the present disclosure, an opening of 5-6 millimeter (mm) at the first premolar region can be desirable for treatment of deep bite, open bite, and/or other malocclusions. For example, an aim of repositioning jaw elements to treat a patient with Class II, Division I deep bite can be to cause a 2 mm inter-incisal clearance (e.g., space between the incisal teeth of the upper jaw and incisal teeth of the lower jaw) resulting in a 5-6 mm opening at the first premolar region (e.g., teeth). By contrast, an aim of repositioning jaw elements to treat a patient with Class II, Division II deep bite can be to cause 0 mm of inter-incisal clearance (e.g., portions of the dental appliance with incisal teeth therein contact) resulting in a 5-6 mm opening at the first premolar region. Further, an aim of repositioning jaw elements to treat a patient with Class II, open bite can be to increase the inter-incisal clearance, as compared to repositioning jaw elements for Class II, Division 1 deep bite, resulting in a 5-6 mm opening at the premolar region. For example, in a 2 mm anterior open bite patient, a 4 mm inter-incisal clearance can be optimal. In various embodiments, the repositioning jaw element 106, 108 can inherently cause disclusion of posterior teeth of the patient.

The repositioning jaw elements 106, 108 interfacing, interacting, and/or engaging can be used to reposition a patient's lower jaw (e.g., lower jaw 112 illustrated in the embodiment of FIG. 1A-1B) by placing a force on the patient's jaw. The force can include a force on the jaws of patient for sagittal correction. The force can, for instance, sagittally move the patient's lower jaw (e.g., in an anterior or posterior direction) to reposition the patient's jaw.

Figure 12A:
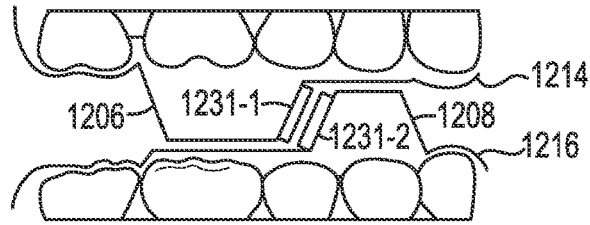
FIGS. 12A-12B illustrate examples of devices according to a number of embodiments of the present disclosure.
Figure 12B:
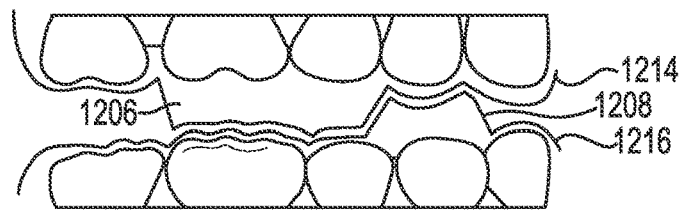

In some embodiments, repositioning jaw elements, such as the first repositioning jaw element 106 and second repositioning jaw element 108, can include occlusal surfaces of the repositioning jaw elements that substantially follow the contours of the occlusal surfaces of teeth on an opposing jaw of the patient (e.g., as illustrated in the embodiment of FIG. 12B). For instance, the occlusal surface (e.g., the top surface) of the first repositioning jaw element 106 can substantially follow the contours of the occlusal surfaces of the posterior teeth of the lower jaw (e.g., the occlusal surfaces of the posterior teeth of the lower jaw that the first repositioning jaw element 106 may contact). The occlusal surface of the second repositioning jaw element 108 can substantially follow the contours of the occlusal surfaces of the posterior teeth of the upper jaw (e.g., the occlusal surfaces of posterior teeth of the upper jaw that the second repositioning jaw element 108 may contact). Shaping the occlusal surfaces of repositioning jaw elements based on the patient's dentition may, for instance, avoid interference between cusps of teeth that may otherwise hit interferences in an opposing jaw which could increase the likelihood of unwanted tooth and/or jaw movements.

Figure 10A:
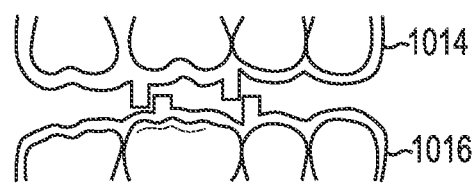
FIGS. 10A-10C illustrate examples of occlusal features of devices for repositioning jaws according to a number of embodiments of the present disclosure.
Figure 10B:
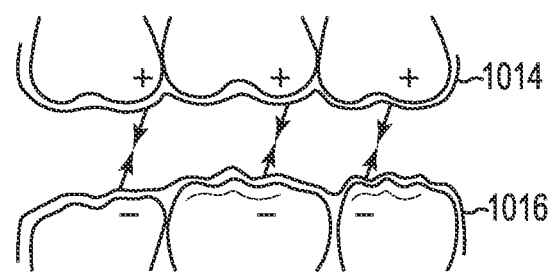
Figure 10C:
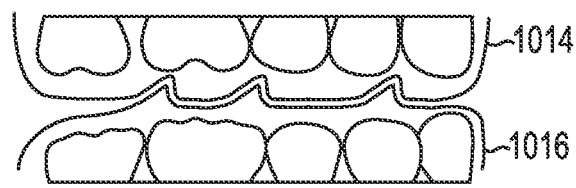

Alternatively and/or in addition, in some embodiments, occlusal surfaces of the repositioning jaw elements and/or other occlusal surfaces of the removable dental appliance can have a geometry that differs from the contours of the occlusal surfaces of teeth that are of an opposing jaw of the patient (e.g., as illustrated in the embodiment of FIG. 10C). For instance, the geometry can include a pattern to match a new jaw position (e.g., forward or backward lower jaw position) of the patient (e.g., as discussed further herein).

In accordance with some embodiments of the present disclosure, a removable dental appliance can include the first shell 114 and second shell 116. The removable dental appliance can be configured to reposition a number of teeth of the patient's upper dentition and a number of teeth of the patient's lower dentition concurrently with repositioning of the patient's jaw. The simultaneous treatment of misalignment of a patient's jaw (e.g., Class II correction) in conjunction with teeth alignment issues (e.g., rotation, tipping, etc.) can shorten treatments times compared to sequential treatment protocols that first treat the misalignment of a patient's jaw before treating the misalignment of the patient's teeth. To help accomplish this objective, the repositioning jaw elements 106, 108, in accordance with a number of embodiments, avoid and/or do not interfere with the engagement of the shell with the teeth contained therein.

The simultaneous treatment of misalignment of a patient's jaw concurrently with teeth misalignment can assist in the treatment of repositioning the patient's jaw. If untreated, teeth misalignment may encourage occlusion in the original jaw position instead of the desired jaw position (e.g., the intended or final jaw position), since the optimal interdigitation between the arches coincides with the original jaw position. Realignment of the teeth so that the teeth fit together best in the desired jaw position can reinforce the desired jaw position when the appliances are removed. Repositioning of the patient's jaw can include retraining the muscles associated with the movement of the lower jaw. Due to the misalignment of a patient's teeth, a lower jaw of the patient can be incorrectly positioned in a retruded position because the teeth position with the best fit may force the jaw into a more retruded position than physiologically comfortable. A treatment whereby the teeth fit better in an anteriorly positioned mandible can relieve the joint compression that may take place when the mandible is retruded. The jaw muscles of the patient can be retrained to hold the lower jaw in a more forward (and more comfortable) position.

In contrast, the removable dental appliance embodiments discussed herein can comprise a first shell 114, a second shell 116, a first repositioning jaw element 106 extending from a surface of the first shell 114, and a second repositioning jaw element 108 extending from a surface of the second shell 116 and can concurrently treat misalignment of the patient's jaw and misalignment of the patient's teeth. Concurrent treatment can avoid and/or prevent reversion and/or retraining of the muscles in an incorrect position, among other benefits. Further, removable dental appliance embodiments, in accordance with the present disclosure, can result in fewer braces and/or elastics as compared to prior solutions. In growing patients, the concurrent treatment may also encourage growth of the jaw(s) in a more favorable direction.

Although the present embodiment of FIGS. 1A-1C illustrates repositioning jaw elements extending from an occlusal surface of a shell and/or near an occlusal surface of one or more teeth of a patient, embodiments are not so limited. The repositioning jaw elements, in some embodiments, can extend from a buccal surface, a lingual surface, an occlusal surface, and/or a combination thereof.

In some embodiments, the repositioning jaw elements (e.g., first repositioning jaw element 106 and second repositioning jaw element 108 illustrated in FIG. 1C) can be hollow and/or can be filed with a material, such as a tooth colored material, a clear material, an acrylic, and/or a composite, among other materials, including materials that are printed via a three-dimensional (3D) printer and/or a through a stereolithography process. The extra material can, for instance, provide additional compressive strength as compared to a hollow repositioning jaw element.

In some embodiments, the hollow space within the repositioning jaw element can be used as a reservoir for the disbursement of medications or other items within the patient's mouth. For example, breath freshening agents, medications to aid in moving of teeth and/or improvement of the condition of the teeth and/or gums of the patient may be provided therein and dispensed through holes and/or passages formed in the interior and/or exterior sides of the repositioning jaw element.

A hollow repositioning jaw element can increase the flexibility of the shell to which the repositioning jaw element is attached. The increased flexibility introduced can lower the functionality and/or the retention of the dental appliance in a vertical or horizontal direction. For example, as a patient moves to a fully engaged sagittal jaw position and the repositioning jaw elements interface, the force placed on the shell can result in a gingival line of the shell flaring (e.g., moving away) from the gum line of the patient. In a number of embodiments, a number of design features and/or elements can be used to reduce and/or eliminate the increase in flexibility, such as grooves and curved repositioning jaw elements (e.g., as discussed further herein in regards to the embodiment of FIG. 4, among other locations).

In some embodiments, the repositioning jaw elements can be shaped to minimize and/or prevent degrading the retention and/or functionality of the shell of the dental appliance. For example, the buccal-lingual width of a repositioning jaw element can be different on an occlusal surface of the repositioning jaw element (e.g., top surface) than on a buccal-lingual width of a surface of the repositioning jaw element adjacent to the shell (e.g., bottom surface). For instance, the buccal-lingual width of a repositioning jaw element can be wider on an occlusal surface of the repositioning jaw element than on a buccal-lingual width of a surface of the repositioning jaw element adjacent to the shell. Such a shape can be similar to the construction of an I-beam, as illustrated in the embodiment of FIG. 12D, with the wider buccal-lingual occlusal surface interfacing with an occlusal surface of a repositioning jaw element positioned on an opposing jaw.

In accordance with some embodiments of the present disclosure, the repositioning jaw elements can be positioned on the removable dental appliance near unerupted and/or removed $2^{nd}$ and/or $3^{rd}$ molar teeth. Repositioning jaw elements positioned on the removable dental appliance near the unerupted and/or removed $2^{nd}$ and/or $3^{rd}$ molar teeth can, for instance, provide increased area for tooth movements. Alternatively and/or in addition, a spring feature can be positioned on the removable dental appliance near unerupted and/or removed $2^{nd}$ and/or $3^{rd}$ molar teeth. For example, a spring feature can be positioned on a first removable dental appliance and a tab feature can be positioned on a second removable dental appliance to interface with the spring feature. The spring feature can guide the lower jaw of the patient to a position (e.g., a forward or backward position), for example (e.g., as illustrated in the embodiment of FIG. 9B).

Figure 11A:
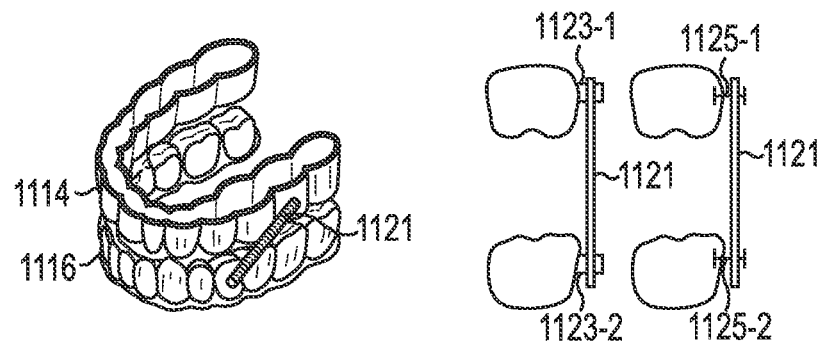
FIGS. 11A-11B illustrate examples of devices for repositioning jaws according to a number of embodiments of the present disclosure.
Figure 11B:
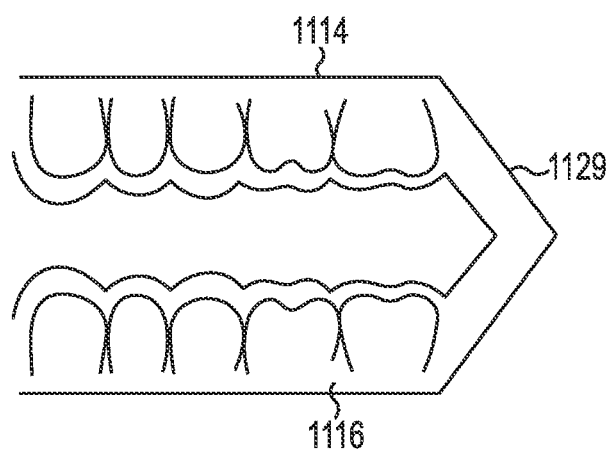

In a number of examples, a variety of features can be used in addition to and/or in place of repositioning jaw elements to guide the lower jaw to a position (e.g., a forward or backward position). Example features can include connecting the first shell and the second shell using material at posterior sides of the shells, a rigid structure, and/or ridges, among other features (e.g., as illustrated in the embodiments of FIGS. 11A and 11B, as discussed further herein).

Figure 2A:
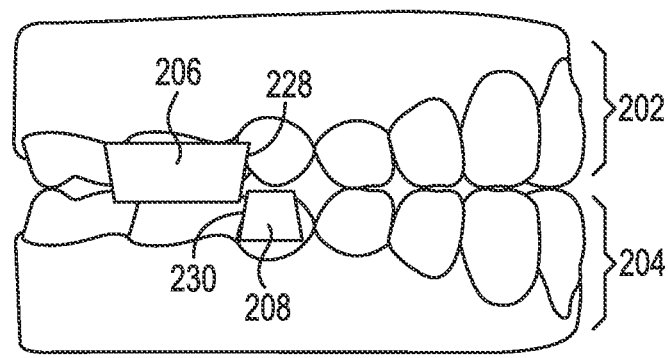
FIG. 2A illustrates a side view of an upper jaw with a first repositioning jaw element and a lower jaw with a second repositioning jaw element according to a number of embodiments of the present disclosure.

FIG. 2A illustrates a side view of an upper jaw 202 with a first repositioning jaw element 206 and a lower jaw 204 with a second repositioning jaw element 208 according to a number of embodiments of the present disclosure. The upper jaw 202, the first repositioning jaw element 206, the lower jaw 204, and the second repositioning jaw element 208 illustrated in FIG. 2A can include virtual images of jaws and repositioning jaw elements, respectively (e.g., virtual jaws and/or virtual repositioning jaw elements), as discussed further herein. As illustrated in the embodiment of FIG. 2A, the first repositioning jaw element 206 can be positioned near a buccal surface of the posterior teeth (e.g., molars and bicuspids) of the upper jaw 202 of the patient to move the position (e.g., to move sagittally) of the lower jaw 204 in a forward direction or backward direction.

Although not illustrated in FIG. 2A, the first repositioning jaw element 206 can extend from a buccal surface of a first shell of a dental appliance. A buccal surface of a shell, as used herein, can include an exterior surface of a shell near the buccal surface of the teeth therein. Further, in various embodiments, the first repositioning jaw element 206 can be positioned near a lingual surface of the first shell. A lingual surface of a shell can include an exterior surface of the shell near the lingual surface of the teeth therein.

The second repositioning jaw element 208 can be positioned near a buccal surface of the posterior teeth (e.g., bicuspids) of the lower jaw 204 of the patient to move the position of the lower jaw 204 in a forward direction or backward direction. Although not illustrated in FIG. 2A, the second repositioning jaw element 208 can extend from a buccal surface of a second shell of a dental appliance.

The first repositioning jaw element 206 and the second repositioning jaw element 208 can interface. For instance, a first surface 228 of the first repositioning jaw element 206 can interface with a second surface 230 of the second repositioning jaw element 208. The first repositioning jaw element 206 and the second repositioning jaw element 208 can be positioned to interface in a presence of a temporary bite (e.g., a fully engaged sagittal jaw position of the patient's upper dentition and the patient's lower dentition) in a manner to reposition the patient's jaw. A fully engaged sagittal jaw position, as previously discussed, can include a relationship of the mandible and the maxilla when the upper and lower jaw are closed as far as the dental appliance with the repositioning jaw elements will allow (e.g., a partial occlusal jaw position).

For example, the first surface 228 of the first repositioning jaw element 206 interfacing with the second surface 230 of the second repositioning jaw element 208 can place a force on the patient's jaw to reposition the patient's jaw. The force can, for instance, sagittally move the patient's lower jaw 204.

In various embodiments, at least one of the repositioning jaw elements 206, 208 can extend past an occlusal plane of the upper jaw 202 and/or lower jaw 204 of the patient. For example, the first repositioning jaw element 206 can extend past the occlusal plane of the upper jaw 202 to interface with the second repositioning jaw element 208. The second repositioning jaw element 208 may not extend past the occlusal plane of the lower jaw 204, for instance. Alternatively, the second repositioning jaw element 208 can extend past the occlusal plane of the lower jaw 204 to interface with the first repositioning jaw element 206 and the first repositioning jaw element 206 may not extend past the occlusal plane of the upper jaw 202. Further, in some embodiments, both the first repositioning jaw element 206 and the second repositioning jaw element 208 can extend past the occlusal plane of the upper jaw 202 and the lower jaw 204, respectively, to interface with one another.

Figure 2B:
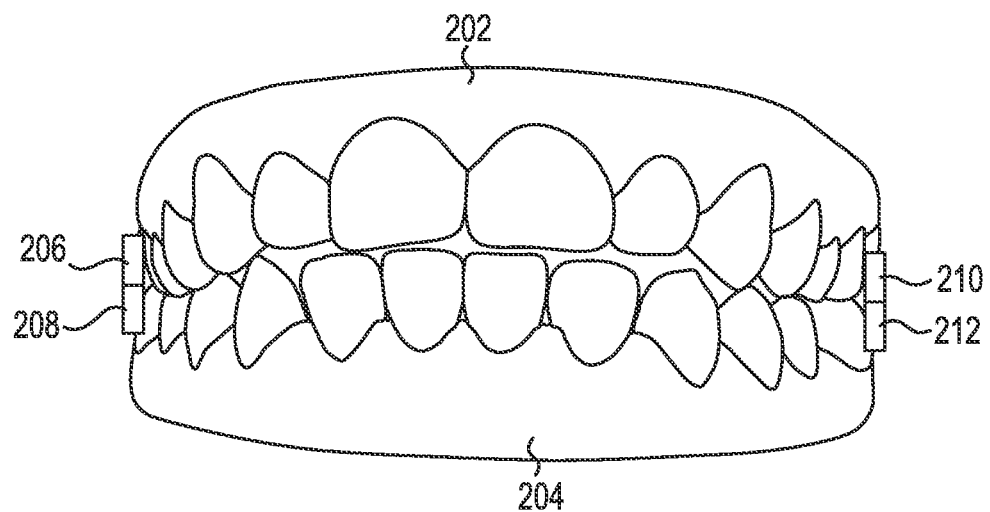
FIG. 2B illustrates a front view of an upper jaw with a first repositioning jaw element and a third repositioning jaw element and a lower jaw with a second repositioning jaw element and a fourth repositioning jaw element according to a number of embodiments of the present disclosure.

FIG. 2B illustrates a front view of an upper jaw 202 with a first repositioning jaw element 206 and a third repositioning jaw element 210 and a lower jaw 204 with a second repositioning jaw element 208 and a fourth repositioning jaw element 212 according to a number of embodiments of the present disclosure. The upper jaw 202, the first repositioning jaw element 206, the third repositioning jaw element 210, the lower jaw 204, the second repositioning jaw element 208, and the fourth repositioning jaw element 212 illustrated in FIG. 2B can include virtual images of jaws and repositioning jaw elements, respectively (e.g., virtual jaws and/or virtual repositioning jaw elements), as discussed further herein. As illustrated by FIG. 2B, two repositioning jaw elements (e.g., the first repositioning jaw element 206 and the third repositioning jaw element 210) can be positioned near buccal surfaces of the upper jaw 202 and two repositioning jaw elements (e.g., the second repositioning jaw element 208 and the fourth repositioning jaw element 212) can be positioned near buccal surfaces of the lower jaw 204.

For example, the first repositioning jaw element 206 can be positioned near the buccal surfaces of posterior teeth (e.g., molars and/or bicuspids) of the upper jaw 202 and the second repositioning jaw element 208 can be positioned near the buccal surfaces of posterior teeth (e.g., bicuspids) of the lower jaw 204. The first repositioning jaw element 206 and the second repositioning jaw element 208 can be located near a first posterior side of the patient's dentition (e.g., positioned on a first posterior side of a first shell and a second shell).

The first repositioning jaw element 206 and the second repositioning jaw element 208 can include surfaces designed to interact, interface, and/or otherwise engage with one another. For instance, a first surface of the first repositioning jaw element 206 can interface with a second surface of a second repositioning jaw element 208. The first surface can include a slanted surface on a mesial-facing surface of the first repositioning jaw element 206 and the second surface can include a slanted surface on a distal-facing surface of the first repositioning jaw element 208, for example.

The third repositioning jaw element 210 can be positioned near the buccal surfaces of posterior teeth (e.g., molars and/or bicuspids) of the upper jaw 202 and the fourth repositioning jaw element 212 can be positioned near the buccal surfaces of posterior teeth (e.g., bicuspids) of the lower jaw 204. The third repositioning jaw element 210 and the fourth repositioning jaw element 212 can be located near a second posterior side of the patient's dentition (e.g., positioned on a second posterior side of a shell of a first shell and a second shell).

The third repositioning jaw element 210 and the fourth repositioning jaw element 212 can include surfaces designed to interact, interface, and/or otherwise engage with one another. For instance, a third surface of the third repositioning jaw element 210 can interface with a fourth surface of the fourth repositioning jaw element 212. The third surface can include a slanted surface on a mesial-facing surface of the third repositioning jaw element 210 and the fourth surface can include a slanted surface on a distal-facing surface of the fourth repositioning jaw element 212, for example.

The surfaces of the repositioning jaw elements 206, 208, 210, 212 can be angled, in various embodiments, to guide the lower jaw 204 into the intended and/or final jaw position and/or prevent unwanted lateral movement. The surfaces can be angled in buccal-lingual and/or mesial-distal direction. The angle of the surfaces (e.g., two surfaces that are designed to interface) can be comprised of supplemental angles (e.g., have the same slants at the interface).

For example, the first surface of the first repositioning jaw element 206 and the second surface of the second repositioning jaw element 208 can interface at a first slant. The third surface of the third repositioning jaw element 210 and the fourth surface of the fourth repositioning jaw element 212 can interface at a second slant.

Although not illustrated by the embodiments of FIG. 2B, the first repositioning jaw element 206 can extend from a buccal surface of a first shell of a dental appliance and/or the second repositioning jaw element 208 can extend from a buccal surface of a second shell of the dental appliance. The first repositioning jaw element 206 and the second repositioning jaw element 208 can be located near a first side of the patient's dentition (e.g., the right side of the patient's dentition). The third repositioning jaw element 210 can extend from a buccal surface of the first shell of the dental appliance and the fourth repositioning jaw element 212 can extend from a buccal surface of the second shell of the dental appliance. The third repositioning jaw element 210 and the fourth repositioning jaw element 212 can be located near a second side of the patient's dentition (e.g., a left side of the patient's dentition).

In some embodiments, repositioning jaw elements can extend from a lingual surface of the shells. A lingual surface of a shell can include an exterior surface of the shell near the lingual surface of the teeth therein. For example, in some embodiments, the first repositioning jaw element 206 and third repositioning jaw element 210 can each extend from a lingual surface of the first shell and the second repositioning jaw element 208 and fourth repositioning jaw element 212 can each extend from a lingual surface of the second shell. Positioning the repositioning jaw elements on the lingual surface of the shell can, for instance, result in a dental appliance that is more aesthetically pleasing to the patient because the repositioning jaw elements are less visible to others (e.g., decreasing the prominence of the repositioning jaw elements).

Figure 13A:
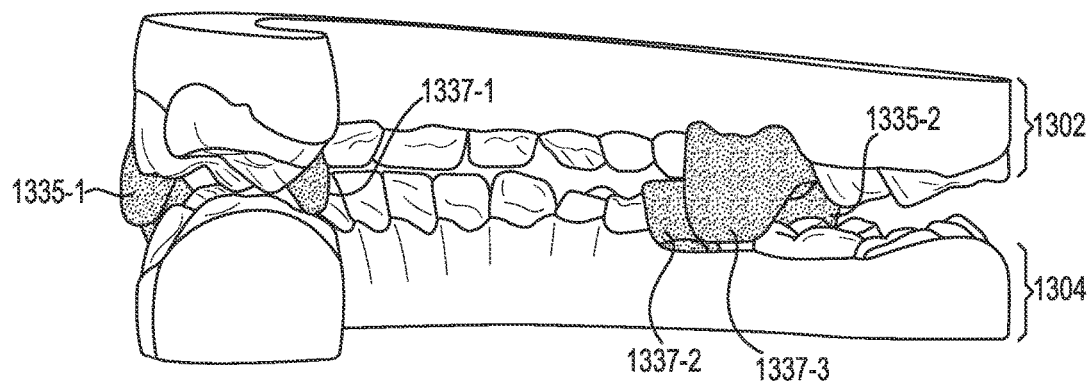
FIGS. 13A-13B illustrate examples of side surface features according to a number of embodiments of the present disclosure.
Figure 13B:
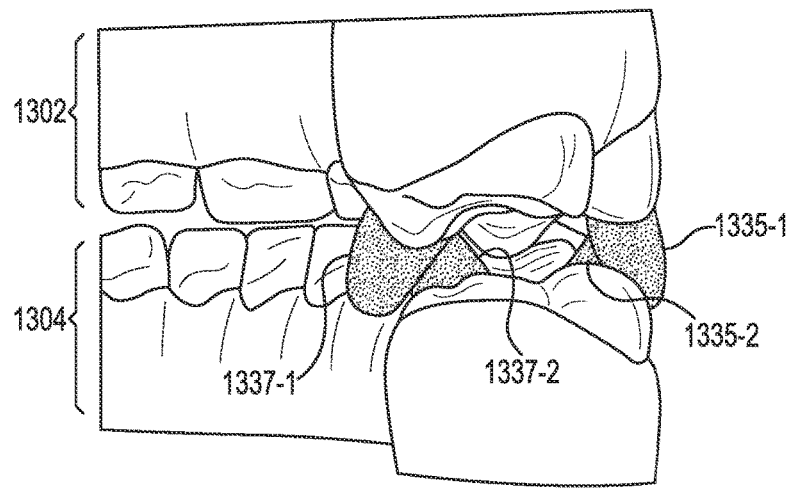

Alternatively and/or in addition, a number of repositioning jaw elements can extend from a lingual surface of the shells and a number of repositioning jaw elements can extend from a buccal surface of the shell (e.g., as illustrated by FIGS. 13A-13B). In such embodiments, the first repositioning jaw element 206, the second repositioning jaw element 208, the third repositioning jaw element 210, and the fourth repositioning jaw element 212 can each extend from a buccal surface of the first shell and the second shell. In addition, a fifth repositioning jaw element can extend from a lingual surface of the first shell and a sixth repositioning jaw element can extend from a lingual surface of the second shell; a seventh repositioning jaw element can extend from a lingual surface of the first shell and a eighth repositioning jaw element can extend from a lingual surface of the second shell. The fifth repositioning jaw element and sixth repositioning jaw element can be located near the first side of the patient's dentition and the seventh repositioning jaw element and eight repositioning jaw element can be located near the second side of the patient's dentition. Positioning repositioning jaw elements on the lingual surface of the shells in addition to the buccal surface of the shells can, for instance, provide additional stability, decrease the aesthetic prominence of the repositioning jaw elements, and/or limit lateral movement, among other benefits.

In some embodiments, a plurality of repositioning jaw elements can extend from the buccal surface of the first shell and a plurality of repositioning jaw elements can extend from the buccal surface of the second shell. The plurality of repositioning jaw elements extending from buccal surfaces can, for instance, decrease the prominence of the repositioning jaw elements as compared to a single repositioning jaw element extending from each buccal surface.

In accordance with a number of embodiments, a repositioning jaw element extending from a buccal surface can be used to treat crossbite in a patient. For instance, a repositioning jaw element extending from a buccal surface of a first shell and a repositioning jaw element extending from a buccal surface of a second sell can interface to tip a molar tooth in a buccal direction to treat crossbite in a patient.

FIG. 3 illustrates an example of a method 320 for separating an upper dentition from a lower dentition according to a number of embodiments of the present disclosure. Separating the upper dentition from the lower dentition according to the method 320 can allow for treatment of malocclusions such as excessive or inadequate overjet, excessive or inadequate overbite, and/or crossbite, for instance.

At block 322, the method 320 includes moving at least one tooth with a dental appliance having a first shell configured to receive a number of teeth of a patient's upper dentition, the number of teeth comprising the at least one tooth. That is, the first shell can include a shell configured to receive a number of teeth of the patient's upper dentition and reposition at least one tooth of the number of teeth of the patient's upper dentition.

At block 324, the method 320 includes separating a patient's upper dentition from the patient's lower dentition utilizing the dental appliance. For instance, the separation can include separating the occlusal surfaces to a threshold distance to prevent an occlusal surface of the first shell from contacting an occlusal surface of a second shell. The second shell can include a shell configured to receive a number of teeth of the patient's lower dentition and reposition at least one tooth of the number of teeth of the patient's lower dentition.

The dental appliance, at block 326, can interface a first surface of a first repositioning jaw element of the first shell with a second surface of a second repositioning jaw element of a second shell of the dental appliance. The second shell can, for instance, be configured to receive a number of teeth of the patient's lower dentition. The dental appliance can separate occlusal surfaces of the number of teeth of the patient's upper dentition from the occlusal surfaces of the number of teeth of the patient's lower dentition as the patient moves to a fully engaged sagittal jaw position, for example. The surface area of the repositioning jaw elements that engage the upper jaw/shell to the lower jaw/shell while the disengaged areas are separated may be built so that the engagement is a better fit than the existing occlusion (e.g., greater points or surfaces in contact) so that the preferred position of the patient is the engaged surface area instead of the current occlusion.

A sagittal jaw position can include a relationship of the mandible and the maxilla when the upper jaw and the lower jaw are closed and the teeth are in contact. A fully engaged sagittal jaw position, as used herein, can include a relationship of the mandible and the maxilla when the upper and lower jaw are closed as far as the dental appliance with the repositioning jaw elements will allow (e.g., as the first surface of a first repositioning jaw element interfaces, interacts, and/or engages the second surface of the second repositioning jaw element). That is, in a fully engaged sagittal jaw position, at least some of the teeth of the upper jaw and at least some of the teeth of the lower jaw are not in contact. Further, in some embodiments, at least some of the occlusal surface of the first shell and the occlusal surface of the second shell are not in contact in a fully engaged sagittal jaw position.

As previously discussed, the fully engaged sagittal jaw position may be needed in the treatment of malocclusion such as excess or insufficient overjet, excess or insufficient overbite, and/or crossbite. For instance, separating the occlusal surfaces can allow for moving a lower jaw of the patient or opening up the bite to a desired range of jaw opening extending from the current position of occlusion. It can also allow for decompression of a lower jaw forward from an undesirable backwards position into a more comfortable (and esthetically pleasing) anteriorly displaced position. The advancement can be unilateral or bilateral.

In a number of embodiments in accordance with the present disclosure, the occlusal surfaces can be separated to a threshold distance to prevent an occlusal surface of the first shell from contacting an occlusal surface of the second shell. An example threshold distance can be one millimeter, however, a treatment professional may determine another suitable distance and such distances are within the scope of the embodiments of the present disclosure.

In various embodiments, the method 320 can include separating the occlusal surfaces of the number of teeth the patient's upper dentition from the occlusal surfaces of the number of teeth of the patient's lower dentition as the patient moves to the fully engaged sagittal jaw position in a plurality of incremental distances utilizing a plurality of dental appliances. For example, the repositioning jaw elements can be designed to incrementally treat a malocclusion, such as excessive or inadequate overjet, excessive or inadequate overbite, and/or crossbite by using repositioning jaw elements provided on a plurality of dental appliances. In some embodiments, the increment can include a gradual movement (e.g., sagittal movement) of the lower jaw by shifting the position of the repositioning jaw elements and/or shifting the length of one or more repositioning jaw elements on each of a series of the plurality of dental appliances (e.g., as discussed further herein with regard to FIG. 7).

Figure 4A:
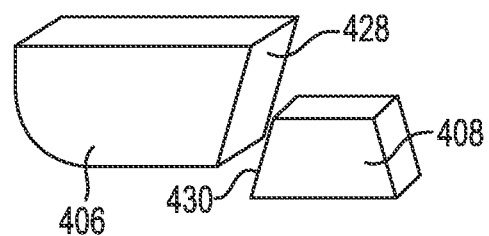
FIGS. 4A-4C illustrate examples of repositioning jaw elements according to a number of embodiments of the present disclosure.
Figure 4B:
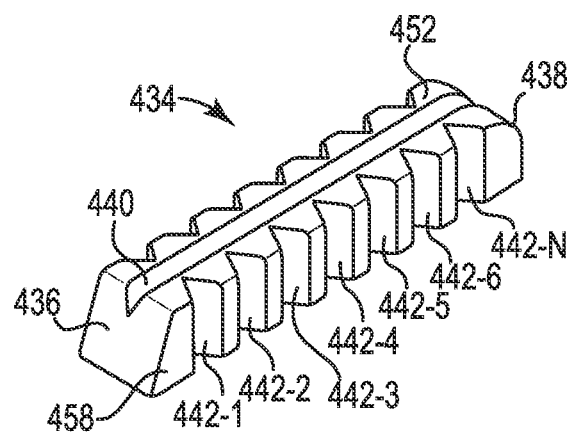
Figure 4C:
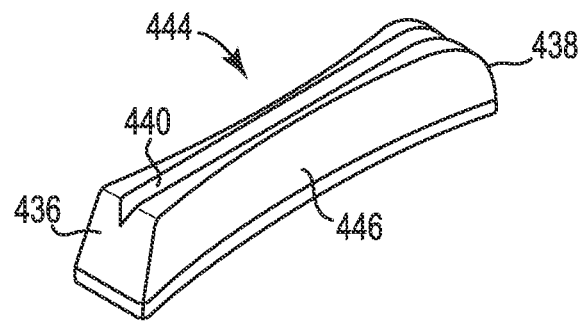

FIGS. 4A-4C illustrate examples of repositioning jaw elements according to a number of embodiments of the present disclosure. FIG. 4A illustrates an example of two repositioning jaw elements 406, 408. The two repositioning jaw elements 406, 408 can be virtual repositioning jaw elements and/or physical repositioning jaw elements. The first repositioning jaw element 406 can include a first repositioning jaw element positioned on a first shell of the dental appliance. The second repositioning jaw element 408 can include a second repositioning jaw element positioned on a second shell of the dental appliance.

As illustrated by FIG. 4A, the first repositioning jaw element 408 can include a first surface 428 and the second repositioning jaw element 408 can include a second surface 430. The first surface 428 can be a slanted surface on a mesial-facing surface of the first repositioning jaw element 406 and the second surface 430 can be a slanted surface on a distal-facing surface of the second repositioning jaw element 408. The surfaces 428, 430 can interface at the slant (e.g., the angled surfaces), for instance.

In a number of embodiments, a repositioning jaw element can include a curved back surface. For instance, a back surface (a surface on the opposite side relative to the surface that is designed to interface, interact, and/or engage a repositioning jaw element on an opposing jaw) of a repositioning jaw element can be curved in a distal direction. As illustrated by FIG. 4A, the back surface of the first repositioning jaw element 406 is curved in a distal direction. The curving can, for instance, improve comfort for a patient due to the reduction in sharp surfaces exposed to the tongue and/or other soft tissues of the mouth.

FIG. 4B illustrates an example of a repositioning jaw element 434 according to a number of embodiments of the present disclosure. The repositioning jaw element 434 can include a virtual repositioning jaw element and/or a physical repositioning jaw element, for instance. The repositioning jaw element 434 can include four side surfaces 436, 438, 458 (e.g., the remaining side surface is facing away from the view). The first side surface 436 can include a surface that can interface, interact, and/or engage with another surface of a repositioning jaw element on a shell of an opposing jaw. As illustrated, the first side surface 436 can be slanted. The second side surface 438 can include a back surface that is curved. For instance, the second side surface 438 can be curved in a distal direction to improve comfort for the patient.

As illustrated by FIG. 4B, in various embodiments, a repositioning jaw element 434 can include a groove 440 on a top surface 452 of the repositioning jaw element 434. For instance, a reinforcement groove and/or guide groove can be placed on a top surface 452 of a virtual and/or physical repositioning jaw element. The top surface 452 of a repositioning jaw element, as used herein, can include a surface of the repositioning jaw element extending toward an occlusal and/or coronal surface of teeth on an opposing side of the patient's jaw. A groove, as used herein, can include a hollow channel within a repositioning jaw element. The groove 440 on the top surface 452 of the repositioning jaw element 434 can extend in a horizontal direction (e.g., a mesial-distal direction), for instance.

Alternatively and/or in addition, in a variety of embodiments, a repositioning jaw element 434 can include a side groove on a buccal side surface and/or a lingual side surface (e.g., side surface 458) of a repositioning jaw element 434. A buccal side surface of a repositioning jaw element, as used herein, can include a side of the repositioning jaw element extending toward and/or adjacent to the cheek of the patient. A lingual side surface of the repositioning jaw element, as used herein, can include a side of the repositioning jaw element extending toward and/or adjacent to the tongue of the user. Grooves (e.g., a top groove and/or number of side grooves) can, for example, increase a rigidity of the repositioning jaw element 434 as compared to a repositioning jaw element without grooves and/or can minimize and/or prevent degrading the retention and/or functionality of the shell of the dental appliance. A groove can also function on the shell of each jaw during treatment.

In various instances, a plurality of side grooves 442-1, 442-2, 442-3, 442-4, 442-5, 442-6 . . . 442-N) can be placed on the buccal side surface and/or the lingual side surface (e.g., side surface 458) of the repositioning jaw element 434. For example, the side grooves 442-1 . . . 442-N can be placed on each of the buccal side surface and lingual side surface (e.g., side surface 458) of a virtual repositioning jaw element and/or a physical repositioning jaw element. The side grooves 442-1 . . . 442-N can each include a hollow channel within the side surface of the repositioning jaw element 434. The side grooves 442-1 . . . 442-N can extend in vertical direction (e.g., an inferior-superior direction.) As illustrated by FIG. 4B, in some embodiments, a repositioning jaw element 434 can include a top groove 440 on a top surface 452 and side grooves 442-1 . . . 442-N on side surfaces (e.g., side surface 458).

In some embodiments, the side grooves 442-1 . . . 442-N can include coronal-apical grooves positioned at interproximal regions of at least one of the number of teeth that the repositioning jaw element 434 extends from. That is, each side groove can be placed at an interproximal region of two teeth.

Although the present embodiment of FIG. 4B illustrates a top groove 440 and a plurality of side grooves 442-1 . . . 442-N in a V-shape, embodiments in accordance with the present disclosure are not so limited. The grooves can include a variety of geometric shapes and sizes. For instance, the grooves can include portions of circles, hexagons, rectangles, and/or octagons, among other shapes and/or sizes. Geometric patterns may be used in lieu of grooves, so long as the pattern provides adequate structural rigidity that a groove or series of grooves may provide.

FIG. 4C illustrates an example of a repositioning jaw element 444 according to a number of embodiments of the present disclosure. The repositioning jaw element 444 can be a virtual repositioning jaw element and/or a physical repositioning jaw element, for instance. The repositioning jaw element 444 can include four side surfaces 436, 438, 446 (the remaining side surface is facing away from the view). The first side surface 436 can include a surface that can interface, interact, and/or engage with another surface. As illustrated, the first side surface 436 can be slanted. The second side surface 438 can include a back surface that is curved. For instance, the second side surface 436 can be curved in a distal direction to improve comfort for the patient. Further, as illustrated by the repositioning jaw element 444 of FIG. 4C, the repositioning jaw element 444 can include a top groove 440 in the top surface of the repositioning jaw element 444.

In accordance with some embodiments, a repositioning jaw element 444 can include curved side surfaces. For instance, a buccal side surface and/or a lingual side surface (e.g., side surface 446) can be curved in at least one of a buccal and/or lingual direction. As illustrated by FIG. 4C, the curved side surface 446 can include a bowed curve. For instance, the curved side surface 446 can result in the top surface of the repositioning jaw element 444 being shaped in a bone shape. A curved side surface 446 can increase a rigidity of the repositioning jaw element 444 as compared to a non-curved side surface and/or can minimize and/or prevent degrading the retention and/or functionality of the shell of the dental appliance, for example, by allowing greater surface area of the shell to engage the teeth than if the side surfaces were not curved.

FIGS. 5A-5C illustrate examples of repositioning jaw elements according to a number of embodiments of the present disclosure. FIGS. 5A-5C illustrate an example of a repositioning jaw element. The repositioning jaw element can be a virtual repositioning jaw element and/or a physical repositioning jaw element, in various embodiments. For instance, FIG. 5A illustrates a top-down view 550 of the repositioning jaw element. The top-down view 550 of the repositioning jaw element can include a view of two side surfaces with side grooves 542-1, 542-2, 542-3, 542-4, 542-5, 542-6, 542-7, 542-8, 542-9 . . . 542-P, a surface that can interface, interact, and/or engage with another surface 536, a back surface 538, and a top surface 552.

In accordance with some embodiments, side surfaces can be beveled. For instance, the buccal side surface and lingual side surface with side grooves 542-1 . . . 542-P can be beveled to include a different buccal-lingual width on a bottom than a top of the side surfaces of the repositioning jaw element. For example, the buccal-lingual width on the bottom can be wider than the buccal-lingual width on the top of the side surfaces of the repositioning jaw element. In such embodiments, the occlusal surface of the repositioning jaw element can have a narrower buccal-lingual width than a surface of the repositioning jaw element adjacent to and/or near the shell of the dental appliance (e.g., bottom surface of the repositioning jaw element). Beveling of the side surfaces can, for instance, include beveling the surface 536 and/or the back surface 538 to have a wider buccal-lingual width on the top than the bottom of the side surfaces (e.g., as discussed further with regard to FIG. 5B). Beveling the side surfaces 536, 538 and side grooves 542-1 . . . 542-P can, for example, assist in manufacturing the dental appliance where the appliance is built from a positive reference model (e.g., such as a 3D printed model or stereolithography (SLA) model).

The repositioning jaw element illustrated in FIG. 5A can include a plurality of side grooves 542-1 . . . 542-P on a buccal side surface and/or a mesial side surface. Beveling the buccal side surface and/or lingual side surface can, for instance, include beveling the side grooves 542-1 . . . 542-P. For instance, the buccal-lingual width of the bottom of the side grooves 542-1 . . . 542-P (the surface adjacent to and/or near the shell) can be wider than the buccal-lingual width of the top of the side grooves 542-1 . . . 542-P (the surface of the side grooves adjacent to and/or near the top surface 552 of the repositioning jaw element).

FIG. 5B illustrates a view 553 of the repositioning jaw element. The repositioning jaw element of FIGS. 5A and 5B can include the same and/or different repositioning jaw elements, in various instances. For example, FIG. 5B can include a view of repositioning jaw element illustrated in the embodiment of FIG. 5A from the point of view of arrow 541.

The view 553 of the repositioning jaw element can include a view of the surface that can interface, interact, and/or engage with another surface (e.g., the surface 536 of FIG. 5A). For instance, the surface can include a top adjacent to a top surface 552 of the repositioning jaw element, a bottom adjacent to a bottom surface 554 of the repositioning jaw element, and two sides adjacent to the buccal and/or lingual side surfaces 531-1, 531-2 of the repositioning jaw element.

As illustrated by FIG. 5B, the buccal-lingual width of the surface can be beveled. For instance, the buccal-lingual width of the bottom of the surface (e.g., adjacent to the bottom surface 554 of the repositioning jaw element) can be wider than the buccal-lingual width of the top of the surface (e.g., adjacent to the top surface 552 of the repositioning jaw element).

Further, as illustrated by the arrow 556, the surface that can interface, interact, and/or engage with another surface can be slanted. For instance, the surface can be slanted at an angle in a mesial-distal direction.

FIG. 5C illustrates an example side view 560 of a repositioning jaw element. The repositioning jaw element can be a virtual repositioning jaw element and/or a physical repositioning jaw element, in some embodiments. The repositioning jaw element of FIGS. 5A, 5B, and 5C can include the same and/or different repositioning jaw elements, in various instances. For example, FIG. 5C can include a view of repositioning jaw element illustrated in the embodiment of FIG. 5A from the point of view of arrow 543. The side view 560 can include a view of a buccal and/or lingual side surface 558. The buccal and/or lingual side surface 558 can include a top adjacent to a top surface 552 of the repositioning jaw element, a bottom adjacent to a bottom surface 554 of the repositioning jaw element, a first side adjacent to the surface that can interface, interact, and/or engage with another surface 536 of the repositioning jaw element, and a second side adjacent to a back surface 538 of the repositioning jaw element. The buccal and/or lingual side surface 558, as illustrated by FIG. 5C, can include a plurality of side grooves.

As illustrated by FIG. 5C, repositioning jaw elements in accordance with the present disclosure can include a slanted top surface. A slanted top surface can include a slant in height from the surface 536 to the back surface 538. For instance, the slant in height can include a higher coronal-apical height of a repositioning jaw element in a mesial direction than a coronal-apical height of the repositioning jaw element in a distal direction. Such a slant can, for instance, create a more comfortable experience for the patient as the jaw of the patient may not close in a flat direction (e.g., not parallel to a horizontal plane). In other words, the vertical distance between the upper jaw and the lower jaw may be greater in the anterior region than in the posterior region for some patients or greater in the posterior region than in the anterior region for others, depending on the original positioned and the desired position (e.g., the intended and/or final position) of the jaw. By accommodating these variances, the patient may occlude in more points (and the temporary bite will be more stable) than if an even flat plane was designed into the temporary bite.

Figure 6:
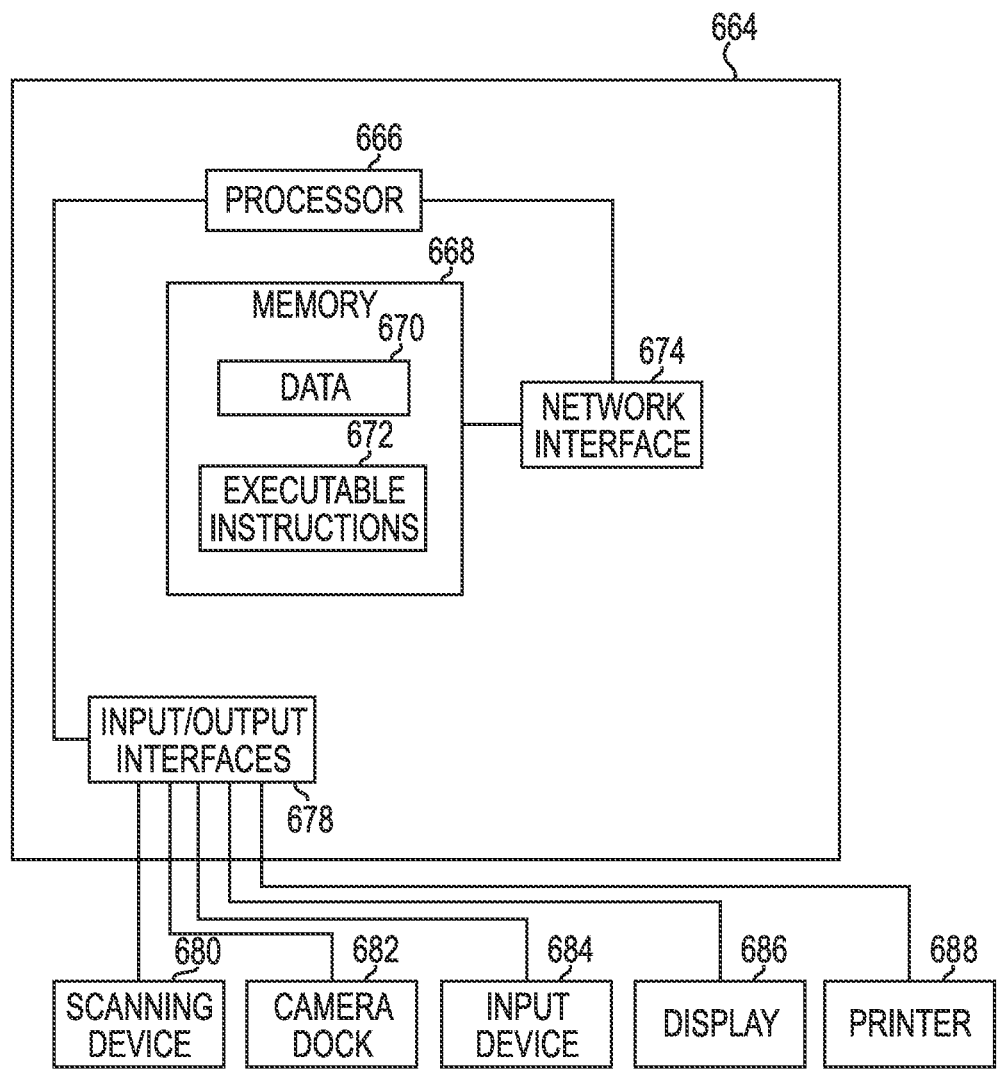
FIG. 6 illustrates an example computing device readable medium having executable instructions that can be executed by a processor to perform a method according to one or more embodiments of the present disclosure.

FIG. 6 illustrates an example computing device readable medium having executable instructions that can be executed by a processor to perform a method according to one or more embodiments of the present disclosure. For instance, a computing device 664 can have a number of components coupled thereto. The computing device 664 can include a processor 666 and a memory 668. The memory 668 can have various types of information including data 670 and executable instructions 672, as discussed herein.

The processor 666 can execute instructions 672 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 668 and/or the processor 666 may be located on the computing device 664 or off the computing device 664, in some embodiments. As such, as illustrated in the embodiment of FIG. 6, the computing device 664 can include a network interface 674. Such an interface 674 can allow for processing on another networked computing device, can be used to obtain information about the patient, and/or can be used to obtain data and/or executable instructions for use with various embodiments provided herein.

As illustrated in the embodiment of FIG. 6, the computing device 664 can include one or more input and/or output interfaces 678. Such interfaces 678 can be used to connect the computing device 664 with one or more input and/or output devices 680, 682, 684, 686, 688.

For example, in the embodiment illustrated in FIG. 6, the input and/or output devices can include a scanning device 680, a camera dock 682, an input device 684 (e.g., a mouse, a keyboard, etc.), a display device 686 (e.g., a monitor), a printer 688, and/or one or more other input devices. The input/output interfaces 678 can receive executable instructions and/or data, storable in the data storage device (e.g., memory), representing a virtual dental model of a patient's dentition.

In some embodiments, the scanning device 680 can be configured to scan one or more physical dental molds of a patient's dentition. In one or more embodiments, the scanning device 680 can be configured to scan the patient's dentition and/or dental appliance directly. The scanning device 680 can be configured to input data into the computing device 664.

In some embodiments, the camera dock 682 can receive an input from an imaging device (e.g., a 2D or 3D imaging device) such as a digital camera, a printed photograph scanner, and/or other suitable imaging device. The input from the imaging device can, for example, be stored in memory 668.

The processor 666 can execute instructions to provide a visual indication of a treatment plan, a dental appliance, and/or a repositioning jaw element on the display 686. The computing device 664 can be configured to allow a treatment professional or other user to input treatment goals. Input received can be sent to the processor 666 as data 670 and/or can be stored in memory 668.

Such connectivity can allow for the input and/or output of data and/or instructions among other types of information. Some embodiments may be distributed among various computing devices within one or more networks, and such systems as illustrated in FIG. 6 can be beneficial in allowing for the capture, calculation, and/or analysis of information discussed herein.

The processor 666, in association with the data storage device (e.g., memory 668), can be associated with the data 670. The processor 666, in association with the memory 668, can store and/or utilize data 670 and/or execute instructions 672 for placing virtual repositioning jaw elements on a shell of a virtual model of a dental appliance. Such data can include the virtual dental model. The virtual model of the dental appliance with the repositioning jaw element can be used to create a physical dental appliance, for instance, as discussed further herein.

The processor 666 coupled to the memory 668 can cause the computing device 664 to perform a method including, for example, providing a virtual model of a dental appliance having a shell configured to reposition a number of teeth of a patient. In various embodiments of the present disclosure, the processor 666 coupled to the memory 668 can cause the computing device 664 to perform the method including positioning a virtual repositioning jaw element on the shell of the virtual model of the dental appliance parallel to a bite plane of the patient, wherein the repositioning jaw element extends from a surface of the shell of the virtual model of the dental appliance.

For instance, to position the virtual repositioning jaw element parallel to a bite plane can include, in some embodiments, removing a virtual image of the number teeth of the patient. With the teeth removed, a virtual representation of the bite plane of the patient can remain and the virtual repositioning jaw element can be positioned parallel to the bite plane.

Further, in some embodiments, the processor 666 coupled to the memory 668 can cause the computing device 664 to perform the method including revising the position of the virtual repositioning jaw element to align with a midline of at least one tooth of the number of teeth. For instance, in some embodiments, the virtual image of the number of teeth can be displayed (e.g., such as, after being removed) and the position of the virtual repositioning jaw element can be automatically revised to align with the midline of the at least one tooth that the virtual repositioning jaw element extends from.

In some embodiments, the processor 666 coupled to the memory 668 can cause the computing device 664 to perform the method including determining a degree of the patient's jaw alignment utilizing a virtual image of the jaw of the patient. The virtual image of the jaw of patient can include a virtual image of the mandible, its related soft and hard tissue, a number of teeth the patient's lower dentition, the maxilla, its related soft and hard tissues, and/or a number of teeth of the patient's lower dentition. The degree of the patient's jaw alignment can include, for instance, a path of articulation or jaw opening and closing. It may also include a repositioned location such as a protruded position, or a combination of semi-articulation and protrusion, for example.

A dental appliance can be made, for example, by thermal-forming a sheet of plastic over a physical dental mold. The physical dental mold, for instance, can represent an incremental position to which a patient's teeth are to be moved. The physical dental mold can be manufactured by downloading a computer-aided Design (CAD) virtual dental model to a rapid prototyping process, such as, for example, a computer-aided manufacturing (CAM) milling, stereolithography, and/or photolithography. The virtual dental mold can be hollowed out or "shelled" before sent for manufacturing to save on material cost, for example.

The dental mold (e.g., set of molded teeth) can be created from a virtual model of a number of teeth of a patient. A virtual model, for example, can include an initial virtual dental model and/or intermediate virtual dental model. A dental mold can be formed in accordance with a unique treatment file that identifies a patient, a stage of a treatment plan, the virtual model of the number of teeth, and/or whether the dental mold is of the upper and/or lower dental arch.

In some embodiments, a treatment file can be accessed by a rapid prototyping apparatus machine, such as a SLA or 3D printing, to form and/or create the dental mold. The result of the dental mold can include a set of molded teeth. The set of molded teeth can include at least a replica of the number of teeth of the patient. The dental mold can be used to make a dental appliance, for example, by creating a negative impression of the dental mold using polymeric sheets of material and vacuum forming the sheets over the dental mold, as discussed above.

For instance, a dental appliance can be formed by layering a thermoformable sheet of material and/or multiple sheets of one or more materials over the dental mold. The materials can include a polymeric material, for instance. Generally, the dental appliance is produced and/or formed by heating the polymeric thermoformable sheet and vacuum or pressure forming the sheet over the dental mold (e.g., a number of molded teeth). The shape of the sheet of material can change thickness on some portions of the sheet as it conforms to the mold shape. A dental appliance can, for example, include a negative impression of the dental mold. The appliance and/or parts thereof may be transparent, semi-transparent, or opaque in such a way as to emulate a nature tooth shade.

However, embodiments in accordance with present disclosure are not so limited. For example, embodiments in accordance with the present disclosure can include forming a dental appliance utilizing a variety of techniques, such as SLA or 3D printing, among other techniques.

In a number of embodiments, the processor 666 coupled to the memory 668 can cause the computing device 664 to perform the method of providing a treatment plan. One or more appliances, including positioners, retainers, removable dental appliances, and/or other appliances for finishing and maintaining teeth positioning, can be utilized by a treatment professional in performing a treatment plan. The treatment plan can include the use of one or more dental appliances, as described herein.

For example, the processor 666 coupled to the memory 668 can cause the computing device 664 to perform the method comprising identifying a misaligned jaw of a patient from a virtual image of the patient's jaw. The identification can include, for instance, determining a degree of the patient's jaw alignment utilizing the virtual image of the patient's jaw.

For example, identifying a misaligned jaw of the patient can include identifying a plurality of jaw placements of the virtual model of the jaw between stages of the treatment plan. Each of the plurality of jaw placements can be identified in a range of stages (e.g., can be associated with). A stage can include, for example, a predetermined period of time of the treatment plan (e.g., 2 weeks). A range of stages may be helpful (e.g., required) to reposition the jaws according to a treatment time used (e.g., needed) to re-posture the mandible.

For instance, a first jaw placement can be associated with a first range of stages (e.g., a first stage to a third stage) of the treatment plan and a second jaw placement can be associated with a second range of stages (e.g., a fourth stage to a fifth stage). A jaw placement, as used herein, can include a relation of the upper jaw and the lower jaw.

The first jaw placement, in some embodiments, can include a misaligned jaw of the patient and the second jaw placement can include a corrected and/or ideal jaw position for the patient (as discussed further herein). In other embodiments, the first jaw placement and the second jaw placement can each include a misaligned jaw of the patient. As previously discussed, the misaligned jaw can include a function of the relative positions of teeth and the mandible and maxilla, either of which may be retruded or protruded relative to the corrected and/or ideal jaw position. The jaw placement can be different for each range of stages but consistent within a range of stages.

A misaligned jaw can be repositioned in the range of stages in a single jaw movement or multiple jaw movements to reposition the jaw. For example, a misaligned jaw can be repositioned to a corrected jaw position. The corrected jaw position can be accomplished in one or more jaw movements in the range of stages.

As an example, a 4 mm jaw reposition can be accomplished in a single jaw movement across twelve stages of a treatment plan (e.g., six months). Dental appliances associated with the twelve stages can include the same repositioning jaw elements designed to move the jaw toward the 4 mm corrected jaw position. However, as further discussed herein, the position and/or orientation of the repositioning jaw elements between stages can be adjusted based on differences in tooth positions and/or jaw relation of the patient.

By contrast, a 6 mm jaw reposition can be accomplished in two 3 mm jaw movements across sixteen stages of a treatment plan (e.g., eight months). Dental appliances associated with the first through eight stages of the sixteen stages can include a first set of repositioning jaw elements designed to move the jaw toward a 3 mm corrected jaw position. Dental appliances associated with the ninth through sixteenth stage of the sixteen stages can include a second set of repositioning jaw elements designed to move the jaw from the 3 mm corrected jaw position toward the 6 mm corrected jaw position (e.g., 3 mm additional jaw movement).

As further discussed herein, the first set of repositioning jaw elements can include the same repositioning jaw elements with adjustments to the position and/or orientation of the repositioning jaw elements between stages based on differences in tooth positions and/or jaw relation of the patient. Similarly, the second set of repositioning jaw elements can include the same repositioning jaw elements with adjustments to the position and/or orientation of the repositioning jaw elements between stages based on differences in tooth positions and/or jaw relation of the patient.

In accordance with a number of embodiments of the present disclosure, a first jaw movement for a patient can be greater than a threshold jaw movement. A first jaw movement, as used herein, can include a first jaw movement of a plurality of jaw movements or the only jaw movement of a treatment plan for a patient. For example, a threshold jaw movement can include a 2 mm and/or a 3 mm jaw movement.

A threshold jaw movement may be used to stimulate correction of the jaw position of the patient. If the first jaw movement is less than the threshold jaw movement, the movement of the jaw of the patient may not stimulate correction of the jaw position.

A jaw movement after the first jaw movement, in some embodiments, can be less than the threshold jaw movement. For example, a jaw movement that is less than the threshold jaw movement can be more comfortable for the patient.

Alternatively, the jaw position of the patient can be moved using a plurality of incremental jaw movements (e.g., small increments) across the range of stages. The incremental jaw movements can, for instance, be across the range of stages to move the jaw of the patient toward the corrected jaw position. Each incremental jaw movement can be a movement that is less than the threshold jaw movement. For example, each jaw movement can include a 0.5 mm jaw movement per stage (or a number of stages) of the range of stages.

Embodiments in accordance with the present disclosure are not limited to the number of jaw placements, the number of stages in a range and/or the number of stages of a treatment plan illustrated by the present example. For instance, embodiments can include more or fewer jaw placements, stages in a range, or stages than discussed. Further, more than one of the identified jaw placements can include a misaligned jaw.

In some embodiments, the processor 666 coupled to the memory 668 can cause the computing device 664 to perform the method comprising providing a treatment plan for the patient. The treatment plan can include a virtual model of a dental appliance having a first shell and a second shell configured to reposition at least one tooth of the patient. The at least one tooth can, for instance, include a tooth on a lower jaw and/or a tooth on an upper jaw of the patient. Further, the virtual model of the dental appliance can include repositioning jaw elements on the first shell and the second shell configured to move a position of the misaligned jaw of the patient (e.g., to move sagittally a position of the misaligned jaw of the patient).

The repositioning jaw elements on the first shell and the second shell can be designed based on an aim of repositioning the misaligned jaw of the patient. A particular repositioning jaw element can have a shape and angle specific to a treatment plan based on at least one of a final and/or intended jaw position, an intended use (e.g., Class I correction, Class II correction, and/or Class III correction), and/or an orientation of a tooth over which the repositioning jaw element is positioned.

According to a number of embodiments of the present disclosure, providing a treatment plan for the patient can include identifying a final jaw position of the patient. The final jaw position of the patient can include, for instance, an improved and/or optimized jaw position. For instance, the final jaw position may include simultaneous contacting of the upper and lower teeth on the right and left sides, and in the anterior and posterior occlusal areas with maximum interdigitation, a best fit or seating of the condyles of the mandible within the joint housing of the temporal bone, and/or correction of malocclusions.

The identified final jaw position can be used to design the virtual repositioning jaw elements. For instance, the virtual repositioning jaw elements can be designed to move the position of the misaligned jaw of the patient toward and/or to the final jaw position (e.g., to move sagittally).

Alternatively and/or in addition, a plurality of dental appliances (e.g., a series of dental appliances) can be used to move the position of the misaligned jaw of the patient toward and/or to the final jaw position. For example, in some embodiments, providing the treatment plan can include providing a virtual model of a plurality of dental appliances. The plurality of dental appliances can be configured to reposition the misaligned jaw in incremental distances according to a number of stages of a treatment plan (e.g., as discussed further with regard to the embodiments illustrated in FIGS. 7A-7D).

The shape and angle of each of the repositioning jaw elements can be specific to a stage of a treatment plan for which the appliance was designed (e.g., successive appliances created according to a treatment plan may have differently positioned, angled, and/or shaped repositioning jaw elements). Repositioning jaw elements that have shapes and angles specific to particular stages of treatment can be advantageous over using generic and/or uniform repositioning jaw element that are not specific to treatment stages and therefore may not accurately provide the desired correction for the treatment stage during which they are used. Such inaccurate treatment can lead to lengthening treatment plans, a need for a revised treatment plan, and/or unnecessary user discomfort, among other drawbacks. In contrast, a number of embodiments of the present disclosure allow for more timely, accurate, and/or comfortable execution of treatment plans.

In various embodiments, the processor 666 coupled to the memory 668 can cause the computing device 664 to perform the method comprising virtually testing the jaw movement to occur by the patient wearing the dental appliance. The virtual testing can include testing jaw movement, in addition to movement of teeth, in a number of embodiments. The virtual repositioning jaw elements can be adjusted based on the virtual testing of the jaw movement. For instance, the virtual repositioning jaw elements can be adjusted to reach an intended jaw position and/or a final jaw position in a treatment plan. The virtual testing and/or adjustment, in some embodiments, can be across a number of stages of a treatment plan.

For example, for each stage of a treatment plan, the instructions can be executed to model forces applied to a virtual model of the jaw by an appliance corresponding to that stage (to simulate actual forces to be applied to a user's physical jaw by a physical appliance). Those forces can include forces applied to the virtual model of the jaw by the virtual repositioning jaw elements, by virtue of the appliance being slightly out of alignment with a current configuration of the virtual model of the teeth and/or include forces applied to the aligner by the user (e.g., when the user wears the physical dental appliance).

The instructions can be executed to position the virtual repositioning jaw elements on the digital teeth of the virtual model of the jaw at a particular stage of treatment and/or adjust a position of the virtual repositioning jaw elements for subsequent stages of treatment. The virtual model of the jaw can be different at each stage of treatment according to the treatment plan (e.g., positioning of the virtual teeth and/or jaw can change). The instructions can be executed to adjust the position of the virtual repositioning jaw elements according to changes to the virtual model of the jaw between treatment stages and/or according to anticipated changes in subsequent stages of treatment (e.g., to help effectuate a desired change to the virtual model of the jaw).

Positioning and/or adjustment of positioning of virtual repositioning jaw elements on a virtual model of a jaw can be automatic (e.g., by operation of software based on force modeling for a particular stage of treatment), manual (e.g., by operation of an operator interacting with the virtual model via an interface with a computing device), or a combination thereof. Likewise, the shape, size, orientation (e.g., various angles with respect to references), and/or attachment location (on the virtual teeth) of the virtual repositioning jaw elements can be automatically set by the software, by manual operation (e.g., an operator can specify the necessary criteria of the virtual repositioning jaw elements and/or modify default criteria provided by the software), or a combination thereof.

An automatic positioning of virtual repositioning jaw elements on the virtual model of the jaw can, for example, occur in response to identifying the plurality of jaw placements of the virtual model of the jaw between stages of the treatment plan, as previously discussed. The position may be guided in part based on a posturing of the patient's jaw in a simulated advanced position, whereby the postured position is captured and/or an input by means of a bite registration that can be physical (e.g., wax or silicon bite) or digital (e.g., intraoral bite scan). Further, in some embodiments, the simulated advanced position may be based on photographs of the patient when the patient's jaw is in the advanced position. At least one of the plurality of jaw placements can be identified as a misaligned jaw, wherein the jaw placement is associated with a range of stages of the treatment plan.

A virtual model of a dental appliance having a first shell and a second shell can be provided for at least one stage of the range of stages with the identified misaligned jaw. Although embodiments are not so limited and embodiments in accordance with the present disclosure can include providing a treatment plan that includes virtual models of dental appliances (e.g., shells) for each stage of the treatment plan.

Virtual repositioning jaw elements can be positioned on the virtual teeth and/or virtual shells at the stage. For example, virtual repositioning jaw elements can be positioned on shells of a first and a last stage of the range of stages with an identified misaligned jaw. The position at the first and the last stage of the range of stages can include an estimated initial repositioning jaw element position and orientation.

The positioned repositioning jaw elements can be refined at intermediate stages of the range of stages (e.g., between the first and the last stage of the range of stages). For example, the position at the first and the last stage of the range of stages can be interpolated with a refined position and orientation at the intermediate stages. The positions at the first stage, last stage, and/or intermediate stages can be adjusted (to a refined position and orientation) to comply with a number of constraints, as discussed below. The refined position and orientation can include an optimized placement of the virtual repositioning jaw elements.

That is, repositioning jaw elements for a first jaw placement that is associated with a number of stages can be the same repositioning jaw elements for each stage in the range of stages and/or can include incremental adjustments between stages. For example, the incremental adjustments can be based on differences in tooth positions and/or jaw position between stages.

Each repositioning jaw element within the range of stages can have a similar gross movement (e.g., move toward a corrected jaw position) with refined position and/or oriented (e.g., refined alignment with arch curve, refined angle of interface, etc.) based on the tooth placement and/or jaw position in the stage. The interpolation between stages can smooth the transition of the repositioning jaw elements between stages within the same range of stages.

As previously discussed, the dental appliances, in some embodiments, can reposition the teeth of the patient in parallel with jaw repositioning. In such embodiments, the stages of the treatment plan can be associated with tooth movement. For instance, movement of teeth of the patient across the stages of the treatment plan can be designed prior to, consecutively with, and/or subsequently to the jaw repositioning planning.

For example, movement of teeth of the patient toward a target position can be planned across a plurality of stages of the treatment plan. Prior to, consecutively with, and/or subsequently to planning the movement of teeth, the jaw repositioning can be planned. As previously discussed, a misaligned jaw of a patient associated with a range of stages of the treatment plan can be identified.

In some embodiments, during designing of the repositioning jaw elements, the movement of teeth can be revised based on and/or to allow for movement of the jaw. For example, the position of the patient's teeth can be revised to support the corrected jaw position and/or to allow for movement to the corrected jaw position. Thereby, the repositioning of the teeth can be planned in parallel with jaw repositioning planning.

As an example, the range of stages may be helpful because certain interferences between the upper jaw and the lower jaw may first be eliminated (e.g., such as movement of one or more teeth) before a more anterior position of the jaw of the patient is attained without significantly opening the bite.

The virtual dental appliance (e.g., virtual shells with the virtual repositioning jaw elements) can be designed using a number of constraints. A constraint, as used herein, can include a physical limit or restriction of the physical dental appliance to satisfy.

For example, the number of constraints can include physical limitations or restrictions of a placement and/or an orientation of the repositioning jaw elements in relation to a current tooth arrangement (e.g., surfaces of particular teeth, position of particular teeth, and/or the arch curve), a current jaw position, and/or a predicted corrected jaw position of the patient. A current tooth arrangement and/or current jaw position, as used herein, can include a tooth arrangement and/or jaw position of the patient at a particular stage of the treatment plan that the repositioning jaw elements are designed for.

The tooth arrangement and/or jaw position of the patient can, for example, change from one stage to another. Repositioning jaw elements can be positioned and/or oriented for a particular stage of a treatment plan based on the tooth arrangement and/or jaw position of the patient at the particular stage. The repositioning jaw elements can be the same for a range of stages of the treatment plan to accomplish a particular jaw movement. However, the position and/or orientation of the repositioning jaw elements can be adjusted (e.g., are different) between the stages of the range.

The constraints can be used to optimize placement of the virtual repositioning jaw elements. For instance, the constraints can each be satisfied, and/or satisfied to the greatest extent possible, to satisfy the greatest subset of the constraints.

For example, the virtual dental appliance can be designed by inputting a corrected jaw position of the patient and outputting repositioning jaw elements that can result in and/or move the jaw toward the corrected jaw position. A corrected jaw position can include a corrected relation of the upper jaw and the lower jaw as compared to the current jaw position of the patient, as previously discussed. In some embodiments, the corrected jaw position can include an ideal jaw position. An ideal jaw position can include an optimal relation of the upper lower and lower jaw. The corrected jaw position can, for instance, be predicted (e.g., calculated) using patient data. For instance, the patient data can include articulation information and/or tooth data of the patient.

The position of the repositioning jaw elements can be adjusted to an ideal fit of the repositioning jaw elements based on the number of constraints. An ideal fit of the repositioning jaw elements can be a position and fit of the repositioning jaw elements that can reposition the patient's jaw toward the corrected jaw position and/or minimize discomfort for a patient, among other benefits.

In some embodiments, the number of constraints for repositioning jaw elements that extend from an occlusal surface of the shells (e.g., herein generally referred to as "occlusal repositioning jaw elements") can include: 1.) a distance between an occlusal repositioning jaw element and a coronal surface of a tooth on the opposing jaw is greater than a threshold distance, 2.) a tooth surface of a tooth beneath an occlusal repositioning jaw element does not extend through a surface of the occlusal repositioning jaw element, 3.) an occlusal repositioning jaw element does not violate buccal-lingual borders of occlusal surfaces of the teeth beneath, 4.) an occlusal repositioning jaw element is aligned with an arch curve direction, 5.) a slant of interface of the occlusal repositioning jaw element is aligned with the occlusal plane normal, 6.) angulation of an occlusal repositioning jaw element in a buccal-lingual direction is limited, 7.) an occlusal repositioning jaw element is positioned from the $1^{st}$ molar to the $1^{st}$ bicuspid, 8.) at least one molar (e.g., $2^{nd}$ or $1^{st}$ molar) on the lower jaw is uncovered by an occlusal repositioning jaw element, among other possible constraints that may be utilized, and 9). a specific bite registration configuration.

For example, the distance between an occlusal repositioning jaw element and a coronal surface of a tooth on the opposing jaw being greater than a threshold distance can account for the thickness of the shells. The thickness of the shells can contribute to the separation difference between jaws. As an example, the threshold distance can include at least two times the thickness of the shell.

A tooth surface of a tooth beneath an occlusal repositioning jaw element not extending through a surface of the occlusal repositioning jaw element can prevent and/or minimize unwanted forces applied to a coronal surface of teeth beneath the repositioning jaw elements. For instance, the teeth beneath the occlusal repositioning jaw elements and/or teeth beneath surfaces of the occlusal repositioning jaw elements (e.g., surfaces that may be able to contact a surface of the shell on the opposing jaw, such as a plane of material discussed further in connection with FIG. 15) may not extend through the occlusal repositioning jaw element and/or surface. To prevent a tooth from extending through a surface of the occlusal repositioning jaw element, a surface of the occlusal repositioning jaw element (such as, the plane of material) can extend across the coronal surface of the tooth beneath the surface of occlusal repositioning jaw element.

Not violating a buccal-lingual border of teeth beneath an occlusal repositioning jaw element can distribute jaw closing forces across the shell of the dental appliance. A buccal-lingual border of teeth beneath can include a buccal or lingual edge of the coronal surface of a tooth.

For instance, to not violate a buccal-lingual border, an occlusal repositioning jaw element can be centered across the buccal-lingual width of the occlusal surface of the shell. Alternatively and/or in addition, a buccal-lingual width of the repositioning jaw element can be revised to center the repositioning jaw element across the buccal-lingual width of the occlusal surface of the shell. This can allow for the occlusal repositioning jaw element to be supported by the occlusal surfaces of the teeth beneath the occlusal repositioning jaw element and assist with preventing jaw closing forces from causing dental appliance dislodgement or gingiva impingement.

An occlusal repositioning jaw element can be aligned with an arch curve direction of a patient by aligning the distal-mesial length of the occlusal repositioning jaw element along the curve of the arch of the patient. Aligning with the arch curve direction, in accordance with embodiments of the present disclosure, can include aligning the distal-mesial length of the occlusal jaw element with the curve of the arch of the patient to a threshold degree (e.g., plus or minus a threshold degree.

Further, a slant of interface of the occlusal repositioning jaw element can be aligned with an occlusal plane normal by the slant of interface of the first surface and/or the second surface being within a threshold degree of parallel (e.g., two degrees) to the occlusal plane normal of the patient. For example, the slant of interface of an occlusal repositioning jaw element aligning with the occlusal plane normal can include the first surface and the second surface interfacing within a threshold degree (e.g., above or below a few degrees) of parallel to the occlusal plane normal.

An occlusal plane, as used herein, can include a direction that is determined based on the bite surface of a patient. As previously discussed, an occlusal plane is parallel to the bite surface of the teeth. An occlusal plane normal is perpendicular to the occlusal plane (e.g., bite surface) of the teeth of the patient, for example.

Aligning with the occlusal plane normal can prevent the angle of interface between a first surface of a first occlusal repositioning jaw element and a second surface of a second occlusal repositioning jaw element from being too shallow to move and/or keep the jaw in a position and too steep to be comfortable for the patient. For instance, a range of angles of the interface of the first surface and the second surface designed to interface, interact, and/or otherwise engage relative to the occlusal plane normal can be used.

The angulation of an occlusal repositioning jaw element in a buccal-lingual direction can include a buccal or lingual angle of the position of the occlusal repositioning jaw element when viewed posteriorly. Ideally, if the occlusal repositioning jaw element is viewed posteriorly, the occlusal repositioning jaw element is parallel to occlusal plane normal (e.g., the occlusal repositioning jaw element is not and/or is minimally positioned/tilted in a buccal or lingual direction). A range of buccal-lingual angulation can be used, for example. Limiting the angle can distribute jaw closing forces evenly among the teeth beneath the occlusal repositioning jaw element and/or surfaces of the occlusal repositioning jaw element.

The range of the positioning of the occlusal repositioning jaw elements can be from the $1^{st}$ molar to the $1^{st}$ bicuspids. The $2^{nd}$ molar and canines can be uncovered by the occlusal repositioning jaw elements. For example, the $2^{nd}$ molars may not be accurately captured by an impression or scan such that it may be beneficial to not position a repositioning jaw element on the $2^{nd}$ molars.

Further, canines may be uncovered by the occlusal repositioning jaw elements as canines are often moved in treatment planning. Not covering the canines with occlusal repositioning jaw elements can allow the canines to be simultaneously moved with the jaw repositioning treatment to decrease treatment time. And, in some cases, at least one molar can be uncovered by the occlusal repositioning jaw elements for labeling purposes for manufacturing (e.g., to mark with identification information).

A specific bite configuration, as used herein, can include one or more specific contacts between opposing teeth that are identified (e.g. a specific desired cusp-tip to fossa relationship or incisal edge to opposing fossae contact area). For instance, with a specific bite configuration the jaws are separated a specified amount in order to integrate the desired dental appliance features.

In a number of embodiments, the number of constraints for repositioning jaw elements that extend from an buccal or lingual surface of the shells (herein generally referred to as "buccal or lingual repositioning jaw elements") can include, for example: 1.) a distance between a buccal or lingual repositioning jaw element and a coronal surface of a tooth on the opposing jaw is greater than a threshold distance, 2.) coronal surface of a tooth supports a buccal or lingual repositioning jaw element, 3.) avoid undercut, 4.) minimize angulation in buccal or lingual direction, 5.) a buccal or lingual repositioning jaw element is aligned with an arch curve direction, 6.) a slant of interface of a buccal or lingual repositioning jaw element is aligned with occlusal plane normal 7.) a buccal or lingual repositioning jaw element is positioned from the $1^{st}$ molar to the $1^{st}$ bicuspid, 8.) symmetry of buccal or lingual repositioning jaw elements on the left side and right side of the jaw, and 9.) buccal or lingual repositioning jaw elements crisscross when viewed posteriorly or anteriorly.

Similarly to occlusal repositioning jaw elements, the distance between a buccal or lingual repositioning jaw element and a coronal surface of a tooth on the opposing jaw being greater than a threshold distance can account for the thickness of the shells. The thickness of the shells can contribute to the separation difference between jaws in an anterior-posterior direction. As an example, the threshold distance can include at least two times the thickness of the shell.

The coronal surface of a tooth beneath a buccal or lingual repositioning jaw element can provide support for the buccal or lingual repositioning jaw element. The support by the tooth beneath can prevent and/or minimize flaring of the buccal or lingual repositioning jaw element in a buccal or lingual direction, respectively, that may occur with biting on the dental appliance.

The undercut of the tooth beneath the buccal or lingual repositioning jaw element can be avoided to prevent and/or minimize hygienic issues for a patient and/or manufacturability of the dental appliance, among other benefits. For instance, a buccal or lingual repositioning jaw element positioned in and/or near an undercut of a tooth can result in a receptacle for food or other debris to collect and can cause difficulty for manufacturing.

The angle of a buccal or lingual repositioning jaw element in buccal or lingual direction, respectively, can be minimized (while being enough to comply with constraint 9) to increase patient comfort. For instance, an increase in the angle of the repositioning jaw element in a buccal direction that extends from a buccal surface of a shell can increase contact with a cheek and/or other tissue of the patient.

Similarly, a buccal or lingual repositioning jaw element can be aligned with an arch curve direction of the patient to prevent and/or minimize the buccal or lingual repositioning jaw element from protruding into tissue of the patient (e.g., cheeks or tongue tissue). Aligning with the arch curve direction can include positioning the buccal or lingual repositioning jaw element as close as possible to the arch curve direction of the patient.

The slant of interface of a buccal or lingual repositioning jaw element, similarly to an occlusal repositioning jaw element, can be aligned with an occlusal plane normal of the patient. A slant of interface of a buccal or lingual repositioning jaw element can be aligned with an occlusal plane normal of a patient by an angle of an interface of a first surface of a first buccal or lingual repositioning jaw element and/or a second surface of a second buccal or lingual repositioning jaw element being within a threshold degree of parallel to the occlusal plane normal of the patient (e.g., perpendicular to the occlusal plane of the patient). For example, the slant of interface of an buccal or lingual repositioning jaw element aligning with the occlusal plane normal can include the first surface and the second surface interfacing within a threshold degree (e.g., above or below a few degrees) of parallel to the occlusal plane normal of the patient.

Aligning with occlusal plane normal can allow for the angle of interface of the first surface of the first buccal or lingual repositioning jaw element and the second surface of the second buccal or lingual repositioning jaw element to be steep enough to move the position of the patient's jaw but not too steep to be uncomfortable for the patient.

The range of the positioning a buccal or lingual repositioning jaw element can be from the $1^{st}$ molar to the $1^{st}$ bicuspids. As previously stated, the $2^{nd}$ molar and canines can be uncovered by the buccal or lingual repositioning jaw elements.

The positioning of buccal or lingual repositioning jaw elements on the left side of the jaw with buccal or lingual repositioning jaw elements on the right side of the jaw can be symmetric to prevent and/or minimize interfacing buccal or lingual repositioning jaw elements on one side of the jaw but not the other (e.g., on the left side but not the right side or the right side but not the left side). If the buccal or lingual repositioning jaw elements are interfacing on one side and not the other, uneven loading of the temporomandibular jaw joint can occur, which can cause a temporomandibular joint disorder (TMJ).

Further, the buccal or lingual repositioning jaw elements crisscrossing when viewed from the posterior or the anterior can assist in positioning and/or holding the lower jaw in an ideal position (e.g., a corrected jaw position and/or a position toward a corrected jaw position). For a first buccal or lingual repositioning jaw element and a second buccal or lingual repositioning jaw element to crisscross, a sufficient angle (in a buccal or lingual direction) and coronal-apical height of the buccal or lingual repositioning jaw elements is present to move the position of the jaw.

FIGS. 7A-7D illustrate examples of a plurality of devices for repositioning jaws according to a number of embodiments of the present disclosure. In some embodiments of the present disclosure, a plurality of dental appliances can be used for treating misalignment of teeth of a patient and/or misalignment of the patient's jaw. For example, a treatment plan can be divided into multiple parts (also called stages) wherein dental appliances (in this case, an appliance having an upper shell and lower shell) are used in succession to move one or more of the patient's teeth and/or jaw from an initial position to a target position. And, wherein specialized dental appliances can be designed for each stage of treatment having cavities with particular dimensions and orientations in which teeth are placed to move one or more of the teeth to a particular position during the particular stage of treatment and/or to move the jaw to a new position when the jaw is closed (e.g., to aid the jaw in following a different path from an open to a closed position to change the path from an initial path to a target path wherein the different path results in a new position of the jaw when it is fully closed). Such a change in jaw path can be accomplished with one device or incrementally with several devices wherein the repositioning jaw elements are in different positions and/or orientations with respect to each other and/or the shell on which they are connected. Accordingly, as discussed above, each of the plurality of dental device appliances can include a treatment stage in an incremental treatment plan.

For example, the plurality of devices can include a series of dental appliances designed to incrementally implement a treatment plan. For instance, the series of dental appliances can incrementally move a position of the patient's jaw (when the jaw is viewed in its fully closed orientation) from stage to stage. The movement of the position of the jaw can include a revised position of the lower jaw of the patient relative to the upper jaw of the patient. Each stage of the treatment plan can move the position of the patient's jaw an incremental distance (e.g., 0.1 mm) from the previous position of the patient's jaw, as discussed further herein. From one stage to the next stage, the position of the patient's jaw can progress toward a final or target jaw position.

The incremental movement of the patient's jaw can occur based on the use of repositioning jaw elements that have slightly different positions or orientations on the shells from stage to stage. For example, the positioning of repositioning jaw elements extending from a first shell and/or second shell of a dental appliance can be revised from a first stage to a second stage. The revised positioning can include changing a mesial-distal length and/or a mesial-distal placement of a repositioning jaw element from one stage (e.g., a first dental appliance) to a next stage (e.g., a second dental appliance), as discussed further herein.

As used herein, a "first stage" does not necessarily mean the original stage of a treatment plan, but is a relative term with respect to other stages. For example, the "first stage" may be a second stage of a 50 stage treatment plan, while the "second stage" may be a tenth stage of the 50 stage treatment plan, while the "third stage" may be a 30th stage of the 50 stage treatment plan, and the "fourth stage" may be a 40th stage of the 50 stage treatment plan.

The treatment plan may just treat the position of the jaw or, in some embodiments, the treatment of the position of the jaws can be combined with the movement of one or more teeth on one or both jaws. For instance, the series of dental appliances can be used to incrementally (e.g., in increments of 0.1 mm) move a position of a misaligned jaw of a patient. This can be beneficial as typical current jaw alignment techniques move a jaw in large increments, such as 0.5 mm or greater, which may cause discomfort to the patient, among other issues.

As discussed above, one or more of the series of dental appliances can also be configured to reposition a number of teeth of the patient's dentition. In some embodiments, one or more of the series of dental appliances can be configured to reposition a number of teeth of the patient's dentition simultaneously with moving a position of a jaw of the patient. An example series of dental appliances can include a first dental appliance comprising a first shell having a first repositioning jaw element extending therefrom and a second shell having a second repositioning jaw element extending therefrom. The first dental appliance can be associated with and/or a part of an initial stage of a treatment plan (e.g., a first stage). The first dental appliance can be configured to move a misaligned jaw of the patient to a first incremental jaw position. Jaw positions can be compared when the jaw is positioned in a similar open-closed position along its path. For example, a comparison can be made when the jaw is in a fully engaged sagittal jaw position. Alternatively, a comparison could be made at other positions of the repositioning jaw elements, for example, when the repositioning jaw elements first contact each other.

The series of dental appliances can include a second dental appliance comprising a first shell having a first repositioning jaw element extending therefrom and a second shell having a second repositioning jaw element extending therefrom. The second dental appliance can be associated with and/or a part of a second stage of the treatment plan (e.g., a subsequent stage to the initial stage). The second dental appliance can be configured to move the misaligned jaw of the patient to a second incremental position.

For example, the second dental appliance can move the misaligned jaw based on the first repositioning jaw element and the second repositioning jaw element having a second position specific to a second stage of the treatment plan. In this manner, the movement induced by use of the repositioning jaw elements can be divided into increments which may allow the movement to be more precise, may allow for more complex movements, and may allow for less discomfort to the patient.

A non-engaged sagittal jaw position, as used herein, can include a position of the patient's upper jaw and lower jaw when the repositioning jaw elements of the first shell and the repositioning jaw elements of the second shell are not interfacing, interacting, and/or engaging (e.g., not touching). For instance, a non-engaged sagittal jaw position may include a position of the first shell and the second shell such that the repositioning jaw elements are not providing a force to move (e.g., sagittally) the patient's jaw.

An engaged sagittal jaw position, as used herein, can include a position of the patient's upper jaw and lower jaw when the repositioning jaw elements of the first shell and the repositioning jaw elements of the second shell are interfacing, interacting, and/or engaging. For example, an engaged sagittal jaw position may include a position of the first shell and the second shell such that the repositioning jaw elements are providing a force to move (e.g., sagittally) the patient's jaw. As discussed herein, in various embodiments, the dental appliance may move a jaw of the patient in one or more other directions in addition to sagittal movement.

Although the present embodiment illustrates two dental appliances in a series of dental appliances, embodiments in accordance with the present disclosure are not so limited. Treatment plans can include a variety of number of dental appliances, including more or less than two dental appliances.

As discussed above, each treatment stage can include a gradual movement of a lower jaw of a patient. The increments can occur based on changes in the mesial-distal length of the repositioning jaw elements and/or shifts in placement of the repositioning jaw elements on the shell (e.g. shift at least one repositioning jaw element in a mesial or distal direction).

For example, as illustrated in each embodiment of FIGS. 7A-7D, the treatment plan can include a number of treatment stages. The embodiments of FIGS. 7A-7D each illustrate two treatment stages. Each of the treatment stages can include a removable dental appliance with a first shell (e.g., first shell 714-1 of the first stage and first shell 714-2 of the second stage of FIGS. 7A-7D, herein generally referred to as "first shell 714") and a second shell (e.g., second shell 716-1 of the first stage and second shell 716-2 of the second stage of FIGS. 7A-7D, herein generally referred to as "second shell 716").

Each first shell 714 can have a number of tooth apertures configured to receive and reposition a number of teeth of a patient's upper dentition and each second shell 716 can have a number of tooth apertures configured to receive and reposition a number of teeth of the patient's lower dentition. A first repositioning jaw element (e.g., 706-1 of the first stage and 706-2 of the second stage of FIGS. 7A-7D, herein generally referred to as "first repositioning jaw element 706") can extend from a surface the first shell 714 and can include a first surface. A second repositioning jaw element (e.g., 708-1 of the first stage and 708-2 of the second stage of FIGS. 7A-7D, herein generally referred to as "second repositioning jaw element 708) can extend from a surface the second shell 716 and include a second surface to interface, interact, and/or engage with the first surface of the first repositioning jaw element 706.

For instance, the first repositioning jaw element 706 and the second repositioning jaw element 708 of each dental appliance can be positioned to interface in the presence of a fully engaged sagittal jaw position of the patient's upper dentition and the patient's lower dentition in a manner to reposition the patient's jaw. For instance, the repositioning can include a forward and downward movement of the patient's lower jaw (e.g., to sagittally move).

Each dental appliance in the treatment plan (e.g., at each treatment stage) can be configured to reposition the number of teeth of the patient's upper dentition and the number of teeth of the patient's lower dentition and/or reposition of the patient's jaw. For instance, the repositioning of the patient's jaw can be incremental across the number of treatment stages. An incremental reposition of the patient's jaw can include, for instance, gradual advancement of the lower jaw. As described further herein, the gradual advancement can be achieved by shifting the placement of at least one of the repositioning jaw elements from a first stage (e.g., first dental appliance) to a second stage (e.g., second dental appliance) and/or changing the mesial-distal length of at least one of the repositioning jaw elements from a first stage to a second stage of the treatment plan.

The embodiments of FIGS. 7A-7D can illustrate repositioning jaw elements 706, 708 oriented in a horizontal line. For instance, each horizontal line can represent a side view of (e.g., shells) a jaw pair (e.g., an upper jaw and a lower jaw). Although not illustrated by FIG. 7A-7D, the repositioning jaw elements 706, 708 can be positioned to extend from a surface of a shell 714, 716 that is shaped to substantially follow a dental arch of a patient. As such, the left end points of each of FIGS. 7A-7D represent a posterior direction 745 and/or regions of the jaws (e.g., of the patient when the dental appliance is worn) and the right end points of each of the FIGS. 7A-7D represent anterior directions 747 and/or regions of the jaws (e.g., of the patient when the removable dental appliance is worn). The repositioning jaw elements 706, 708 extend from the surfaces of the shells.

Figure 7A:
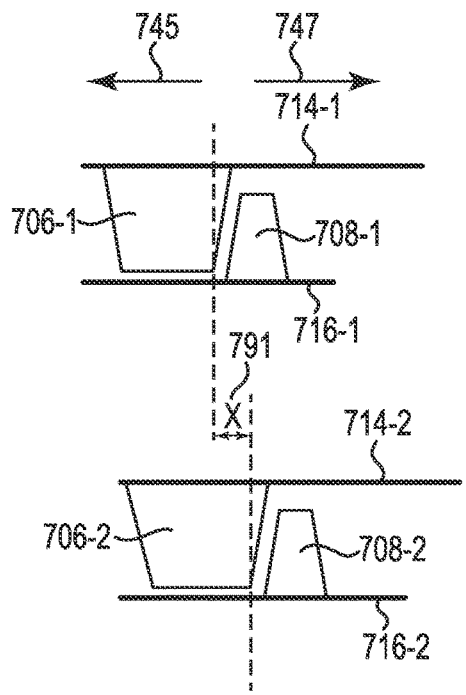
FIGS. 7A-7D illustrate examples of a plurality of devices for repositioning jaws according to a number of embodiments of the present disclosure.

FIG. 7A illustrates an example of a number of treatment stages to reposition a jaw of a patient in gradual advancements by changing a mesial-distal length of a first repositioning jaw element. Changing a mesial-distal length of a repositioning jaw element, as used herein, can include increasing or decreasing the length of the repositioning jaw element along a mesial-distal plane of teeth of the patient. For instance, the first treatment stage can include a first repositioning jaw element 706-1 that extends from a surface of a first shell 714-1 configured to receive and reposition a number of teeth of a patient's upper dentition. A second repositioning jaw element 708-1 can extend from a surface of a second shell 716-1 configured to receive and reposition a number of teeth of the patient's lower dentition.

The mesial-distal length of the first repositioning jaw element 706-1 and the second repositioning jaw element 708-1 can include particular lengths based on the first treatment stage. For instance, the length can be based on an incremental distance of the particular treatment stage. Based on the mesial-distal lengths of the first repositioning jaw element 706-1 and the second repositioning jaw element 708-1 of the first treatment stage, the patient's jaw can be repositioned to a first incremental position and/or distance.

In some embodiments, as illustrated by FIG. 7A-D, the first repositioning jaw elements 706 can include a longer mesial-distal length than the second repositioning jaw elements 708. In some instances, a patient may have posterior teeth on the lower jaw that have not yet fully erupted. The longer mesial-distal length of the first repositioning jaw elements 706 on the first shell 714 can minimize and/or prevent the posterior teeth on the lower jaw from erupting farther than is desirable (e.g., super eruption) while still allowing the posterior teeth to erupt.

A second treatment stage can include a first repositioning jaw element 706-2 that extends from a surface of a first shell 714-2 configured to receive and reposition a number of teeth of the patient's upper dentition. A second repositioning jaw element 708-2 can extend from a surface of a second shell 716-2 configured to receive and reposition a number of teeth of the patient's lower dentition.

The mesial-distal length of the first repositioning jaw element 706-2 of the second treatment stage can be increased from the mesial-distal length of the first repositioning jaw element 706-1 of the first treatment stage. The increase in mesial-distal length can be based on the incremental distance of the particular treatment stage. The change can include, for example, a particular distance value x 791 (e.g., increase by particular distance value x 791) in which the mesial surface of repositioning jaw element 706-2 is extended by a distance "x" in the mesial direction. The second repositioning jaw element 708-2 of the second treatment stage can be the same mesial-distal length as the second repositioning jaw element 708-1 of the first treatment stage and/or can be increased, in various embodiments.

Based on the mesial-distal lengths of the first repositioning jaw element 706-2 and the second repositioning jaw element 708-2 of the second treatment stage, the patient's jaw can be repositioned to a second incremental position and/or distance.

Figure 7B:
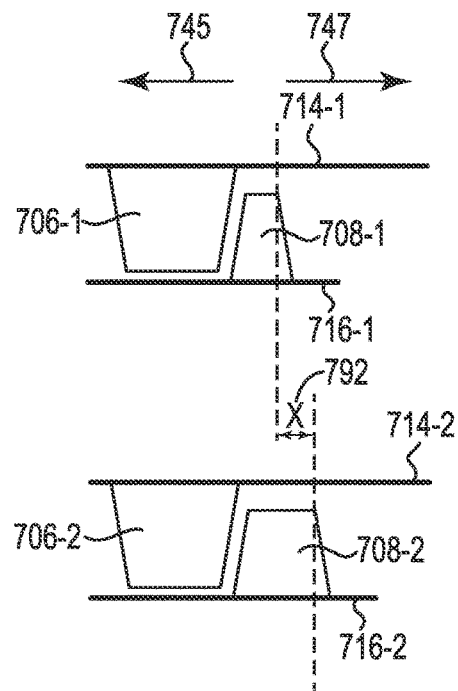

FIG. 7B illustrates an example of a number of treatment stages to reposition a jaw of a patient in gradual advancements by changing a mesial-distal length of a second repositioning jaw element. For instance, the first treatment stage can include a first repositioning jaw element 706-1 that extends from a surface of a first shell 714-1 configured to receive and reposition a number of teeth of a patient's upper dentition. A second repositioning jaw element 708-1 can extend from a surface of a second shell 716-1 configured to receive and reposition a number of teeth of the patient's lower dentition.

The mesial-distal length of the first repositioning jaw element 706-1 and the second repositioning jaw element 708-1 can include particular lengths based on the first treatment stage. The length can be based on an incremental distance of the particular treatment stage. Based on the mesial-distal lengths of the first repositioning jaw element 706-1 and the second repositioning jaw element 708-1 of the first treatment stage, the patient's jaw can be repositioned to a first incremental position and/or distance.

A second treatment stage can include a first repositioning jaw element 706-2 that extends from a surface of a first shell 714-2 configured to receive and reposition a number of teeth of the patient's upper dentition. A second repositioning jaw element 708-2 can extend from a surface of a second shell 716-2 configured to receive and reposition a number of teeth of the patient's lower dentition.

The mesial-distal length of the second repositioning jaw element 708-2 of the second treatment stage can be increased from the mesial-distal length of the second repositioning jaw element 708-1 of the first treatment stage. The increase in mesial-distal length can be based on the incremental distance of the particular treatment stage. The change can include, for example, a particular distance value x 792 (e.g., increase by distance value x 792) in which the mesial surface of repositioning jaw element 708-2 is extended by a distance "x" in the distal direction. The first repositioning jaw element 706-2 of the second treatment stage can be the same mesial-distal length as the first repositioning jaw element 706-1 of the first treatment stage and/or can be increased, in various embodiments. Based on the mesial-distal lengths of the first repositioning jaw element 706-2 and the second repositioning jaw element 708-2 of the second treatment stage, the patient's jaw can be repositioned to a second incremental position and/or distance.

Figure 7C:
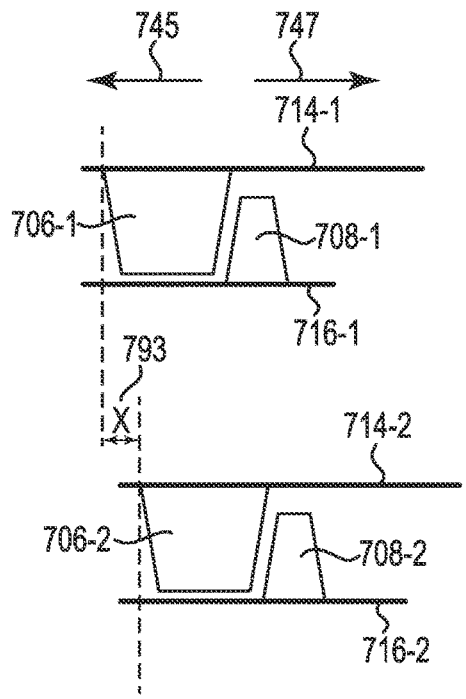

FIG. 7C illustrates an example of a number of treatment stages to reposition a jaw of a patient in gradual advancements by shifting a mesial-distal placement (e.g., shift the placement of the repositioning jaw element in a mesial or distal direction) of the first repositioning jaw element. For instance, the first treatment stage can include a first repositioning jaw element 706-1 that extends from a surface of a first shell 714-1 configured to receive and reposition a number of teeth of a patient's upper dentition. A second repositioning jaw element 708-1 can extend from a surface of a second shell 716-1 configured to receive and reposition a number of teeth of the patient's lower dentition.

The mesial-distal placement of the first repositioning jaw element 706-1 and the second repositioning jaw element 708-1 can include a particular placement adjacent to posterior teeth therein based on the first treatment stage. For instance, the placement can be based on an incremental distance of the particular treatment stage. Based on the mesial-distal placement of the first repositioning jaw element 706-1 and the second repositioning jaw element 708-1 of the first treatment stage, the patient's jaw can be repositioned to a first incremental position and/or distance.

A second treatment stage can include a first repositioning jaw element 706-2 that extends from a surface of a first shell 714-2 configured to receive and reposition a number of teeth of the patient's upper dentition. A second repositioning jaw element 708-2 can extend from a surface of a second shell 716-2 configured to receive and reposition a number of teeth of the patient's lower dentition.

The mesial-distal placement of the first repositioning jaw element 706-2 of the second treatment stage can be shifted in a mesial direction from the mesial-distal placement of the first repositioning jaw element 706-1 of the first treatment stage. The shift in mesial-distal placement can be based on the incremental distance of the particular treatment stage. The shift can include, for example, a particular distance value x 793 (e.g., shift in a mesial direction by a distance value of x 793). The second repositioning jaw element 708-2 of the second treatment stage can be the same mesial-distal placement as the second repositioning jaw element 708-1 of the first treatment stage and/or can be shifted, in various embodiments. Based on the mesial-distal placements of the first repositioning jaw element 706-2 and the second repositioning jaw element 708-2 of the second treatment stage, the patient's jaw can be repositioned to a second incremental position and/or distance.

Figure 7D:
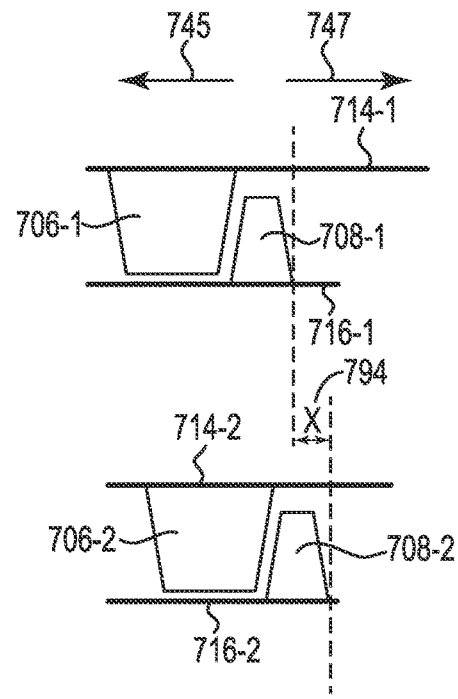

FIG. 7D an example of a number of treatment stages to reposition a jaw of a patient in gradual advancements by shifting a mesial-distal placement of the second repositioning jaw element. For instance, the first treatment stage can include a first repositioning jaw element 706-1 that extends from a surface of a first shell 714-1 configured to receive and reposition a number of teeth of a patient's upper dentition. A second repositioning jaw element 708-1 can extend from a surface of a second shell 716-1 configured to receive and reposition a number of teeth of the patient's lower dentition.

The mesial-distal placement of the first repositioning jaw element 706-1 and the second repositioning jaw element 708-1 can include a particular placement adjacent to posterior teeth therein based on the first treatment stage. For instance, the placement can be based on an incremental distance of the particular treatment stage. Based on the mesial-distal placement of the first repositioning jaw element 706-1 and the second repositioning jaw element 708-1 of the first treatment stage, the patient's jaw can be repositioned to a first incremental position and/or distance.

A second treatment stage can include a first repositioning jaw element 706-2 that extends from a surface of a first shell 714-2 configured to receive and reposition a number of teeth of the patient's upper dentition. A second repositioning jaw element 708-2 can extend from a surface of a second shell 716-2 configured to receive and reposition a number of teeth of the patient's lower dentition.

The mesial-distal placement of the second repositioning jaw element 708-2 of the second treatment stage can be shifted in a distal direction from the mesial-distal placement of the second repositioning jaw element 708-1 of the first treatment stage. The shift in mesial-distal placement can be based on the incremental distance of the particular treatment stage. The shift can include, for example, a particular distance value x 794 (e.g., shift in a distal direction by a distance value of x 794). The first repositioning jaw element 706-2 of the second treatment stage can be the same mesial-distal placement as the first repositioning jaw element 706-1 of the first treatment stage and/or can be shifted, in various embodiments. Based on the mesial-distal placements of the first repositioning jaw element 706-2 and the second repositioning jaw element 708-2 of the second treatment stage, the patient's jaw can be repositioned to a second incremental position and/or distance.

Although the present embodiments of FIGS. 7A-7D illustrate two treatment stages of a treatment plan, embodiments in accordance with the present disclosure are not so limited. Treatment plans can include a variety of number of treatment stages, including more or less than two treatment stages. At least a portion of the treatment stages can include treatment for gradual advancement of the patient's jaw. Further, one or more of the treatment stages may not include repositioning jaw elements, in various embodiments.

FIGS. 8A-8D illustrate examples of repositioning jaw elements according to a number of embodiments of the present disclosure. FIG. 8A illustrates, for instance, repositioning jaw elements 806, 808, 810, 812 that include geometric features 851-1, 851-2, 851-3, 851-4 to engage with a repositioning jaw element on an opposing jaw.

Geometric features 851-1 . . . 851-4, as used herein, can include a variety of protruding geometric shapes (e.g., cylinder, rectangular, etc.) and/or receding geometric shapes (e.g., negative space that matches the protruding geometric shape on a repositioning jaw element on an opposing jaw). For example, a geometric feature 851-1 on the first surface of the first repositioning jaw element 806 of a first shell 814 can include a concave shaped feature and a geometric feature 851-2 on the second surface of the second repositioning jaw element 808 of a second shell 816 can include a convex shaped feature shaped to mate with the geometric feature 851-1 on the first surface of the first repositioning jaw element 806.

Similarly, a geometric feature 851-3 on the third surface of the third repositioning jaw element 810 of the first shell 814 can include a concave shaped feature and a geometric feature 851-4 on the fourth surface of the fourth repositioning jaw element 812 of the second shell 816 can include a convex shaped feature shaped to mate with the geometric feature 851-3 on the third surface of the third repositioning jaw element 810.

Figure 8B:
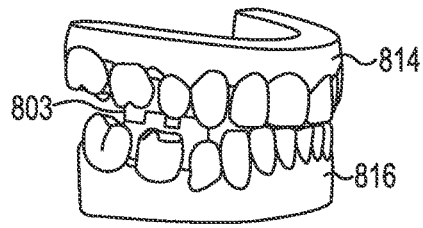

FIG. 8B illustrates a repositioning jaw element 803 on an occlusal surface of a removable dental appliance. As illustrated, the repositioning jaw element 803 can be located on an occlusal surface of a first shell 814 (e.g., an upper dentition).

The repositioning jaw element 803 can, for instance, include an occlusal surface that has a geometry shaped to mate with the contours of the occlusal surfaces of the second shell 816. The mating can, for instance, be designed to reposition the jaw of the patient by guiding the lower jaw of the patient into a forward position or backward position (e.g., to move sagittally).

Figure 8C:
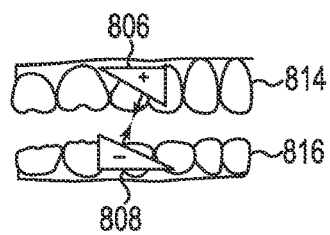
Figure 8D:
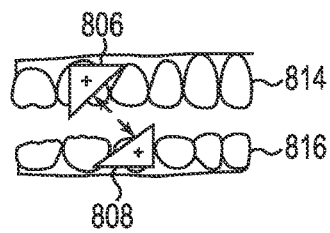

FIGS. 8C-8D illustrate example of repositioning jaw elements 806, 808 with magnets within. Repositioning jaw elements 806, 808 with magnets within can extend from occlusal, buccal, and/or lingual surfaces of shells 814, 816 of a removable dental appliance. The magnets within the repositioning jaw elements 806, 808 on opposing jaws can be opposite poles and/or same poles to guide the lower jaw to a position. For example, opposite poles on magnets can be used to attract the lower jaw into the forward position and/or same poles on magnets can be used to push the lower jaw into the forward position.

FIG. 8C illustrates an example of repositioning jaw elements 806, 808 with magnets within that have opposite poles on opposite jaws to attract the lower jaw (e.g., the second shell 816) into the forward position. In contrast, FIG. 8D illustrates an example of repositioning jaw elements 806, 808 with magnets within that have same poles on opposite jaws to push the lower jaw (e.g., the second shell 816) into the forward position.

Although the embodiments of FIGS. 8C and 8D illustrate attracting or pushing the lower jaw into a forward position (e.g., Class II correction), embodiments in accordance with the present disclosure are not so limited. For example, embodiments in accordance with the present disclosure can include magnets within repositioning jaw elements that attract or push the lower jaw into a backward position (e.g., Class III correction).

Figure 9A:
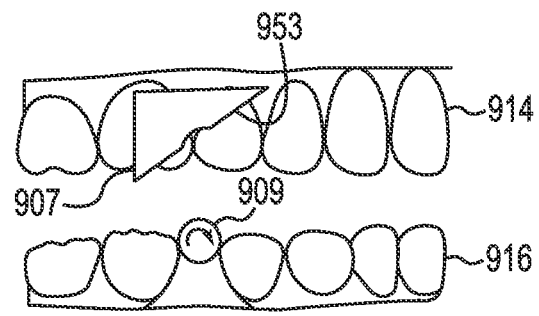
FIGS. 9A-9B illustrate examples of features of devices for repositioning jaws according to a number of embodiments of the present disclosure.
Figure 9B:
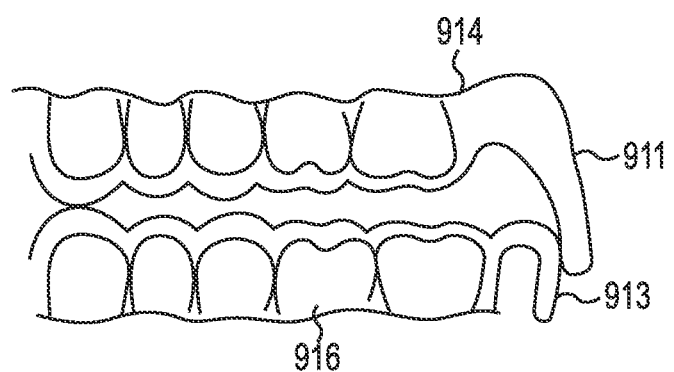

FIGS. 9A-9B illustrate examples of features of devices for repositioning jaws according to a number of embodiments of the present disclosure. The devices illustrated in FIGS. 9A-9C can include removable dental appliances. FIG. 9A, for instance, illustrates an example repositioning jaw element 907 with a groove 953 on a first shell 914 and a geometric feature 909 on a second shell 916.

The groove 953 of the repositioning jaw element 907 can include, for instance, a hollow channel located within and/or on a surface of the repositioning jaw element 907 that is angled (e.g., a surface of the repositioning jaw element 907 that is designed to interface, interact, and/or engage with another repositioning jaw element and/or shell). The groove 953 can be shaped to mate with a geometric feature 909 on a second shell 916 on an opposite jaw. The geometric feature 909 on the second shell 916 on the opposite jaw can include a cylinder shaped feature that can rotate and/or slide down the angled surface of the repositioning jaw element 907 of the first shell 914 until the groove 953 is reached. That is, the groove 953 can limit and/or stop movement of the geometric feature 909 on the second shell 916. The groove 953 and geometric feature 909 combination can, for instance, allow for greater freedom of motion of the lower jaw while repositioning the lower jaw to a forward position or backward position.

In some embodiments, a first repositioning jaw element of a first shell 914 and a second repositioning jaw element of a second shell 916 can include geometric features. For instance, geometric features of a first repositioning jaw element and/or a second repositioning jaw element can include a protrusion and a socket. For example, a first repositioning jaw element can include a protrusion extending from the first repositioning jaw element in a direction toward occlusal surfaces teeth of the opposing jaw. The second repositioning jaw element can include a socket within the second repositioning jaw element. The protrusion of the first repositioning jaw element can fit into the socket of the second repositioning jaw element to assist in guiding the lower jaw into a forward position or a backward position.

FIG. 9B illustrates an example of a device with a first geometric feature 911 on a first shell 914 and a second geometric feature 913 on a second shell 916. For instance, the second geometric feature 913 can include a spring feature positioned on the second shell 916 and the first geometric feature 911 can include a tab feature positioned on the first shell 914 to interface, interact, and/or engage with the spring feature (e.g., the second geometric feature 913). The spring feature can, for instance, guide the lower jaw of the patient to a forward position or backward position, for example. For instance, the first geometric feature 911 interfacing, interaction, and/or engaging with the second geometric feature 913 can provide a force on the lower jaw of the patient to move sagittally the position of the lower jaw.

FIGS. 10A-10C illustrate examples of occlusal features of devices for repositioning jaws according to a number of embodiments of the present disclosure. The devices illustrated in FIGS. 10A-10C can include removable dental appliances.

FIG. 10A illustrates an example device with a plurality of ridges on the occlusal surfaces of the first shell 1014 and a plurality of ridges on the second shell 1016. The ridges can be used to guide the lower jaw of the patient to a position, such as a forward position or a backward position. Ridges, as used herein, can include protrusions that extend in a coronal-apical direction and have a buccal-lingual width (e.g., 1 mm). The ridges on the first shell 1014 can protrude in an alternating order as the ridges on the second shell 1016, for instance.

FIG. 10B illustrates an example of a device with a plurality of pairs of magnets within the occlusal surface of the first shell 1014 and the second shell 1016. The magnets within the occlusal surfaces of the shells 1014, 1016 on opposing jaws can be opposite poles and/or same poles to guide the lower jaw to a forward position or backward position. The plurality of pairs of magnets can be used to distribute the force evenly across the arch and/or across posterior teeth.

FIG. 10C illustrates an example of a device with occlusal surfaces that have a geometry that differs from the contours of occlusal surfaces of teeth that are on an opposing jaw of the patient. For instance, the geometry of the occlusal surface of the first shell 1014 and the geometry of the occlusal surface of the second shell 1016 can include a pattern to match a forward lower or backward lower jaw position of the patient. As illustrated by FIG. 10C, in some embodiments, the geometry can be on occlusal surfaces of a device that does not include repositioning jaw elements and the geometry can retrain the muscles of the lower jaw to be positioned in a forward lower jaw position or a backward lower jaw position (e.g., to move sagittally).

Further, in various embodiments, a dental appliance of the present disclosure can include one or more repositioning jaw elements having a structure to indicate to a patient that the patient has positioned the first and second repositioning jaw elements of the first shell and second shell in a fully engaged sagittal jaw position. For example, in the embodiment of FIG. 10C, the points of the repositioning jaw structure 1016 will stop when they fully engage with the cooperating valleys of the opposing repositioning jaw structure 1014. Other examples of these indicting type structures can be seen in various embodiments illustrated in the figures such as, FIGS. 8A, 8B, and 12B.

FIGS. 11A-11B illustrate examples of devices for repositioning jaws according to a number of embodiments of the present disclosure. The devices illustrated in FIGS. 11A-11B can include removable dental appliances.

In a number of examples, a variety of features can be used in addition to and/or in place of repositioning jaw elements to guide the lower jaw to a position, such as a forward position or a backward position. Example features can include connecting the first shell and the second shell using material at the sides of the shells in the posterior region, a rigid or flexible connecting structure (e.g., as illustrated by FIGS. 11A and 11B), ridges (e.g., as illustrated by FIG. 10A), magnets (e.g., as illustrated by FIG. 10B), and/or occlusal surfaces (e.g., as illustrated by FIG. 10C), among other features.

FIG. 11A illustrates an example of a device with a first shell 1114 and a second shell 1116 connected by a rigid or flexible connecting structure 1121 to advance a lower jaw of the patient to a position, such as a forward position or backward position (e.g., move a lower jaw of the patient or opening up the bite to a desired range of jaw opening extending from the current position of occlusion). The rigid or flexible connecting structure 1121 can form a hinge.

The rigid or flexible connecting structure 1121 can include a strip of material (e.g., an arm), such as metal, polymer, and/or other material, which can connect the first shell 1114 to the second shell 1116. As illustrated by the embodiment of FIG. 11A, the rigid structure 1121 can be connected to the first shell 1114 and the second shell 1116 in a variety of ways. In some embodiments, the rigid or flexible connecting structure 1121 can be connected to the first shell 1114 and the second shell 1116 using magnetic materials 1123-1, 1123-2, pins 1125-1, 1125, and/or similar features.

These features can allow the connecting structure to be easily installed and removed by the patient. For instance, the rigid or flexible connecting structure 1121 can form a hinge that uses magnetic materials 1123-1, 1123-2, pins 1125-1, 1125, and/or similar features to hold the first shell 1114 and the second shell 116 together while allowing the first shell 1114 and the second shell 116 to rotate. When a patient places the first shell 1114 and the second shell 1116 over their teeth, the patient can place the rigid or flexible connecting structure 1121 near the appropriate location. The magnetic materials 1123-1, 1123-2, in some embodiments, can snap the rigid or flexible connecting structure 1121 into the appropriate location (e.g., from a close and/or near appropriate location to the appropriate location). A wire can be placed on a lingual surface of the second shell 1116 (e.g., lower jaw) to distribute the load evening across the dental arch, in various embodiments.

FIG. 11B illustrates an example of a device with a first shell 1114 and a second shell 1116 formed as a single piece. The first shell 1114 (e.g., upper jaw) and the second shell 1116 (e.g., lower jaw) can be connected into one piece to advance a lower jaw of the patient or opening up the bite to a desired range of jaw opening extending from the current position of occlusion. For example, the first shell 1114 and the second shell 1116 can be connected by material 1129 at a right posterior side and a left posterior side of the first shell 1114 and the second shell 1116. The material 1129 can include the same and/or different material than the material of the first shell 1114 and the second shell 1116, for instance. The material 1129 can be flexible to allow jaw articulation while continuing to provide positioning guidance to the jaws.

FIGS. 12A-12B illustrate examples of devices according to a number of embodiments of the present disclosure. The repositioning jaw elements 1206, 1208 of the devices illustrated in FIGS. 12A-12B can interface, interact, and/or engage with one another to move a position of a patient's jaw from a current position of occlusion to a target and/or final position of occlusion (e.g., to move sagittally).

FIG. 12A illustrates an example of a device with a first repositioning jaw element 1206 extending from a surface of a first shell 1214 and a second repositioning jaw element 1208 extending from a surface of a second shell 1216. The first repositioning jaw element 1206 and the second repositioning jaw element 1208 can interface, interact, and/or engage in the presence of fully engaged sagittal jaw position of a patient.

As illustrated by the embodiment of FIG. 12A, in a number of embodiments, one or more of the repositioning jaw elements 1206, 1208 can include a layer of compressible material 1231-1, 1231-2 on a surface designed to interface, interact, and/or engage with another repositioning jaw element. For example, the compressible material 1231-1, 1231-2 can assist in guiding the lower jaw of a patient to a forward or backward position by being in a compressed state when the surfaces are initially interfacing, interacting, and/or engaged, then uncompressing to push the lower jaw forward or backward as the jaws relax. That is, the compressible material 1231-1, 1231-2 can be compressed when the jaws of the patient initially move to a fully engaged sagittal jaw position and, as the patient's jaws relax over a period of time, the compressive material 1231-1, 1231-2 can expand (e.g., increase in thickness from the compressed state) to push the lower jaw forward or backward.

FIG. 12B illustrates an example of a device with a first repositioning jaw element 1206 extending from a surface of a first shell 1214 and a second repositioning jaw element 1208 extending from a surface of a second shell 1216. In some embodiments, at least one of the repositioning jaw elements (e.g., the first repositioning jaw element 1206 and the second repositioning jaw element 1208) can include occlusal surfaces that substantially follow the contours of the occlusal surfaces of teeth on an opposing jaw of the patient.

For instance, as illustrated by the embodiment of FIG. 12B, the occlusal surface (e.g., the top surface) of the first repositioning jaw element 1206 can substantially follow the contours of the occlusal surfaces of the posterior teeth of the lower jaw (e.g., the occlusal surfaces of the posterior teeth of the lower jaw that the first repositioning jaw element 1206 may contact). The occlusal surface of the second repositioning jaw element 1208 can substantially follow the contours of the occlusal surfaces of the posterior teeth of the upper jaw (e.g., the occlusal surfaces of posterior teeth of the upper jaw that the second repositioning jaw element 1208 may contact). Shaping the occlusal surfaces of repositioning jaw elements based on the patient's dentition may, for instance, avoid interference between cusps of teeth that may otherwise hit interferences in an opposing jaw which could increase the likelihood of unwanted tooth and/or jaw movements.

Figure 12C:
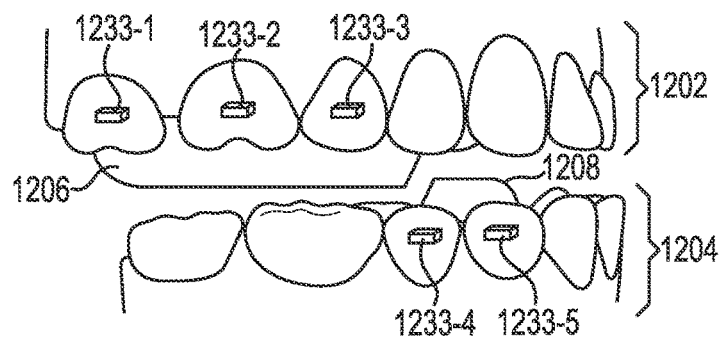
FIGS. 12C-12D illustrate examples of repositioning jaw elements according to a number of embodiments of the present disclosure.
Figure 12D:
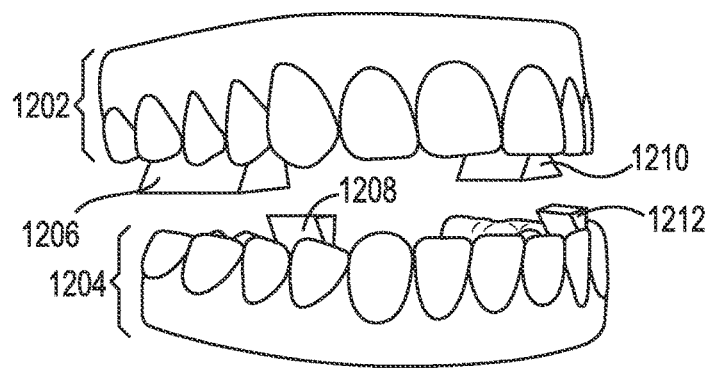

FIGS. 12C-12D illustrate examples of repositioning jaw elements 1206, 1208 according to a number of embodiments of the present disclosure. The upper jaw 1202, the first repositioning jaw element 1206, the lower jaw 1204, and the second repositioning jaw element 1208 illustrated in FIGS. 12C-12D can include virtual images of jaws and repositioning jaw elements, respectively (e.g., virtual jaws and/or virtual repositioning jaw elements), and/or a physical mold. The virtual images and/or physical mold of the jaws 1202, 1204 and repositioning jaw elements 1206, 1208 can be used to determine a treatment plan for the patient and/or to form a physical dental appliance and/or physical repositioning jaw element.

FIG. 12C illustrates a side view of an upper jaw 1202 with a first repositioning jaw element 1206 and a lower jaw 1204 with a second repositioning jaw element 1208 according to a number of embodiments of the present disclosure. In a number of embodiments, one or more attachment elements 1233-1, 1233-2, 1233-3, 1233-4, 1233-5 can be virtually and/or physically attached to a surface of at least some of the virtual teeth, set of molded teeth, and/or physical teeth of a patient. The attachment elements 1233-1 . . . 1233-5 can be used to minimize and/or prevent degrading the retention and/or functionality of the shell of the dental appliance.

For instance, the attachment elements 1233-1 . . . 1233-5 can be added directly to a buccal/facial and/or lingual surface of a patient's tooth. An attachment element, as used herein, can include an attachment sub-device with a small base extending across a mesial-distal and/or incisal-gingival-crown surface of the tooth. The attachment elements 1233-1 . . . 1233-5 can be bonded to any surface of the tooth (and be made either indirectly (e.g. a light or chemical-cured dental composite) or directly (e.g. prefabricated plastic, composite, or porcelain object)). An attachment element bonded to a lingual surface of a tooth of the patient can be more aesthetically pleasing to a patient (and less noticeable to others than an attachment element bonded to a buccal/facial surface). The attachment elements 1233-1 . . . 1233-5 can also be attached to at least some of the anchoring teeth. The attachment elements 1233-1 . . . 1233-5 can include a variety of geometric shapes, such as ovoid, tear-drop, ramp, hexagonal, and/or rectangular, among other shapes.

The one or more attachment elements 1233-1 . . . 1233-5 can be designed to work with a virtual model of a removable dental appliance and/or a physical removable dental appliance. The shell can be shaped, for instance, to be placed over the attachment element(s) 1233-1 . . . 1233-5 to minimize and/or prevent vertical displacement of the shell. For example, the shell can include a ridge on the shell used to retain the dental appliance on the teeth. The attachment elements 1233-1 . . . 1233-5 can, for instance, provide friction between the dental appliance and the teeth to increase retention of the dental appliance. That is, the attachment elements 1233-1 . . . 1233-5 can create greater retention of the dental appliance in a particular direction.

FIG. 12D illustrates a front view of an upper jaw 1202 with a first repositioning jaw element 1206 and a third repositioning jaw element 1210 and a lower jaw 1204 with a second repositioning jaw element 1208 and a fourth repositioning jaw element 1212 according to a number of embodiments of the present disclosure.

In various embodiments, at least one of the repositioning jaw elements 1206, 1208, 1210, 1212 can be shaped to minimize and/or prevent degrading the retention and/or functionality of the shell of the dental appliance. For example, as illustrated in the embodiment of FIG. 12D, the buccal-lingual width of a repositioning jaw element (e.g., the repositioning jaw elements 1206, 1208, 1210, 1212) can be different on an occlusal surface of the repositioning jaw element (e.g., top surface) than on a buccal-lingual width of a surface of the repositioning jaw element adjacent to the shell (e.g., bottom surface). That is, the side surfaces of the repositioning jaw elements can be tapered inward toward the bottom surface. For instance, the buccal-lingual width of a repositioning jaw element can be wider on an occlusal surface of the repositioning jaw element than on a buccal-lingual width of a surface of the repositioning jaw element adjacent to the shell. Such a shape can be similar to the construction of an I-beam with the wider buccal-lingual occlusal surface interfacing with an occlusal surface of a repositioning jaw element positioned on an opposing jaw.

FIGS. 13A-13B illustrate examples of side surface features according to a number of embodiments of the present disclosure. The side surface features and jaws illustrated in FIGS. 13A-13B can include virtual side surface features and virtual jaws of a patient or physical molds of a patient's jaws with side surface features, in some embodiments.

A side surface feature, as used herein, can extend beyond the occlusal plane of a removable dental appliance to engage with buccal and lingual coronal side surfaces of at least one tooth and/or a removable dental appliance on the opposite jaw of the patient. The side surface features can, for instance, add retention to molar teeth to balance movement created by the repositioning jaw elements and/or prevent and/or limit a posterior surface of the removable dental appliance from contacting molars. In various embodiments, the side surface features can include repositioning jaw elements. That is, although not illustrated by the embodiments of FIGS. 13A-13B, the side surface features can be used in addition to repositioning jaw elements, such as repositioning jaw elements 106, 108 illustrated in FIG. 1A.

FIG. 13A illustrates posterior view of an upper jaw 1302 and a lower jaw 1304 with a number of side surface features 1335-1, 1335-2, 1337-1, 1337-2, 1337-3 according to a number of embodiments of the present disclosure. As illustrated by FIG. 13A, the number of side surface features can include buccal side surface features 1335-1, 1335-2 and lingual side surface features 1337-1, 1337-2, 1337-3.

FIG. 13B illustrates a view of a posterior side of the upper jaw 1302 and the lower jaw 1304 with the number of side surface features 1335-1, 1335-2, 1337-1, 1337-2. The upper jaw 1302, the lower jaw 1304, and the number of side surface features 1335-1, 1335-2, 1337-1, 1337-2 illustrated in FIG. 13B can include the same or different jaws and side surface features as illustrated in FIG. 13A, in various embodiments.

The side surface features 1335-1, 1335-2, 1337-1, 1337-2, as illustrated by FIG. 13B, can include a pair of side surface features (e.g., a first buccal side surface feature 1335-1 and a first lingual side surface feature 1337-1) on the first posterior side of the upper jaw 1302 and a pair of side surface features (e.g., a second buccal side surface feature 1335-2 and a second lingual side surface feature 1337-2) on the second posterior side of lower jaw 1304. Each pair of side surface features (e.g., the first buccal side surface feature 1335-1 and the first lingual side surface feature 1337-1) can engage with side surfaces of at least one tooth and/or a removable dental appliance on the opposite jaw of the patient.

Figure 13C:
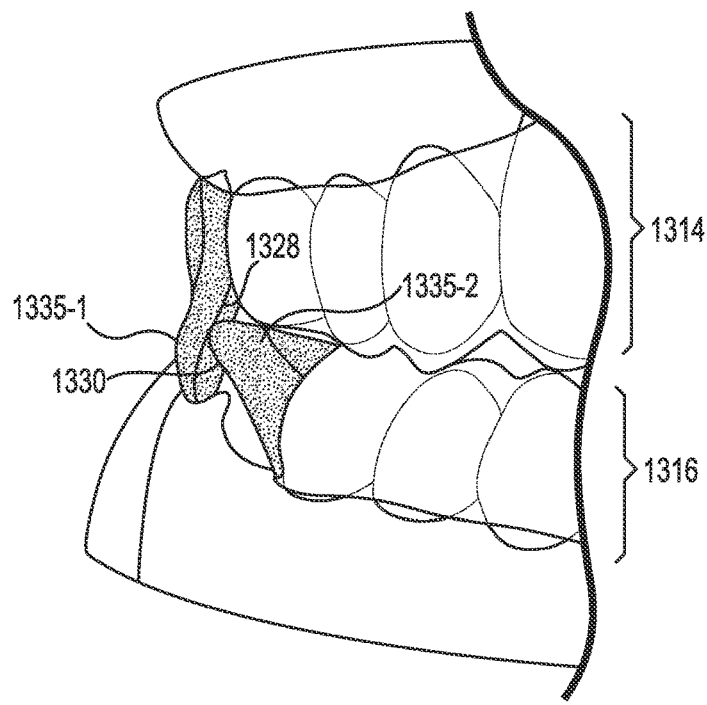
FIGS. 13C-D illustrate a side view of a first shell with a first side surface feature and a second shell with a second side surface according to a number of embodiments of the present disclosure.
Figure 13D:
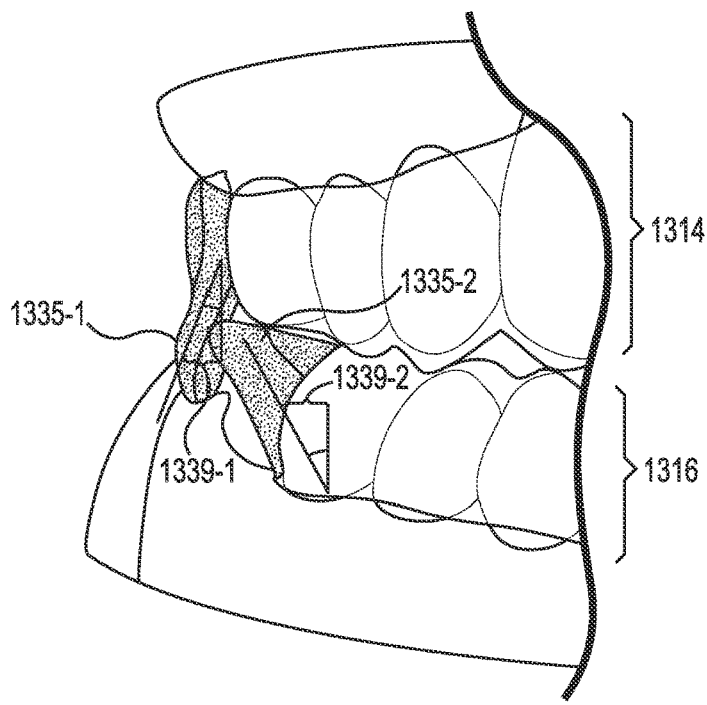

The side surface features 1335-1, 1335-2, 1337, 1, 1337-2, 1337-3 illustrated by FIGS. 13A-13B and the side surface features 1335-1, 1335-2 illustrated by FIGS. 13C-D are illustrated as dotted surfaces for clarity purposes. However, in accordance with the present disclosure, the side surface features can be the same color, texture, and/or formed of the same material as the shells 1314, 1316, the virtual jaws, and/or physical molds of the jaw (e.g., the upper jaw 1302 and the lower jaw 1304).

FIGS. 13C-D illustrate a side view of a first shell with a first side surface feature and a second shell with a second side surface feature according to a number of embodiments of the present disclosure. As previously discussed, in some embodiments the number of side surface features 1335-1, 1335-2 can include repositioning jaw elements extending from buccal and/or lingual surfaces of a dental appliance (e.g., shells).

That is, the first side surface feature 1335-1 of the first shell 1314 can include a first surface 1328 that can interface with a second surface 1330 of the second side surface feature 1335-2 of the second shell 1316. The second side surface feature 1335-2 can include the second surface 1330 that can interface with the first surface 1328 of the first side surface feature 1335-1.

A shell with a repositioning jaw element, such as the first shell 1314 with the first repositioning jaw element (e.g., the first side surface feature 1335-1) and the second shell 1316 with the second repositioning jaw element (e.g., the second side surface feature 1335-2), include continuous dental appliances that contain geometries (e.g., the repositioning jaw elements) that act as jaw repositioning elements. That is, the repositioning jaw elements are geometries of the shells 1314, 1316, and not separate elements attached there to.

For example, as illustrated by the embodiment of FIG. 13D, the first repositioning jaw element (e.g., the first side surface feature 1335-1) and the second repositioning jaw element (e.g., the second side surface feature 1335-2) can be positioned to interface, interact, and/or otherwise engage in the presence of a fully engaged sagittal jaw position of the patient's upper dentition (e.g., the upper jaw 1302 illustrated in FIGS. 13A-13B) and the patient's lower dentition (e.g., the lower jaw 1304 illustrated in FIGS. 13A-13B) in a manner to reposition the patient's lower jaw.

The repositioning jaw elements can be angled 1339-1, 1339-2 to create and/or aim for an ideal fit. An ideal fit of repositioning jaw elements, as previously discussed, is a fit of the repositioning jaw elements that results in repositioning of the patient's jaw (e.g., repositioning towards a corrected jaw position) and/or minimizes discomfort for a patient.

The repositioning jaw elements, in some embodiments, can be angled 1339-1, 1339-2 away from the shells 1314, 1316 of the dental appliance to avoid collision with the shell of the opposing jaw. However, in some embodiments, the angle 1339-1, 1339-2 can be the minimum possible angle to minimize protrusion of the repositioning jaw elements into the cheeks, tongue, and/or other tissue of the patient (e.g., prevent/minimize discomfort) while being great enough to avoid collision with the shell 1314, 1316 of the opposing jaw (and/or to crisscross when anteriorly or posteriorly viewed, as previously discussed in connection with FIG. 6).

As illustrated by FIGS. 13C-13D, the repositioning jaw elements (e.g., the first and second side surface features 1335-1, 1335-2) can crisscross (when viewed anteriorly or posteriorly) and both repositioning jaw elements can extend past an occlusal surface of the respective jaws and/or shells 1314, 1316. For example, the first repositioning jaw element extends past the occlusal surface of the upper jaw and/or the first shell 1314 and the second repositioning jaw element extends past the occlusal surface of the lower jaw and/or the second shell 1316. Extending both repositioning jaw elements past the occlusal surface of the respective jaws and/or shells 1314, 1316 can minimize the height of the first repositioning jaw element (or second repositioning jaw element) as compared to extending only one of the repositioning jaw elements past the occlusal surface of the respective jaw and/or shell.

FIGS. 14A-14B illustrate examples of repositioning jaw elements for adjusting a midline of a patient according to a number of embodiments of the present disclosure. The repositioning jaw elements and jaws illustrated in FIGS. 14A-14B can include virtual repositioning jaw elements and virtual jaws of a patient or physical molds of a patient's jaws with repositioning jaw elements, for instance.

In accordance with a number of embodiments of the present disclosure, the repositioning jaw elements can be used to adjust a midline of a patient. A midline of a patient, as used herein, can include a midsagittal line of the teeth of the upper jaw and the teeth of the lower jaw of the patient.

For instance, repositioning jaw elements can be placed on the right and left posterior side of a shell for the upper jaw and the right and left posterior side of a shell for the lower jaw. The surfaces of repositioning jaw elements on the shell of each jaw that are designed to interface, interact, and/or engage surfaces of repositioning jaw elements on an opposing jaw can be angled at the same angle and/or opposite angles, in various instances. For example, for minor adjustment to the midline of a patient, the surfaces of repositioning jaw elements on the shell of a jaw (e.g., upper or lower) can be angled at opposing angles. In contrast, for larger adjustments to the midline of the patient, the surfaces of repositioning jaw elements (e.g., the right and left posterior side) on the shell of a jaw (e.g., upper or lower) can be angled at the same angle.

FIG. 14A illustrates an example of a side view of an upper jaw 1402 with a first repositioning jaw element 1406 and a third repositioning jaw element 1410 and a lower jaw 1404 with a second repositioning jaw element 1408 and a fourth repositioning jaw element 1412. The first repositioning jaw element 1406 and second repositioning jaw element 1408, and the third repositioning jaw element 1410 and the fourth repositioning jaw element 1412, respectively, can be designed to interface, interface, and/or engage in the present of a fully engaged sagittal jaw position to guide the lower jaw 1404 of the patient in a mesial-distal direction.

In various embodiments, the guidance of the lower jaw 1404 in a mesial-distal direction can be concurrent with guiding the lower jaw 1404 in a forward or backward direction (e.g., anterior-posterior direction). That is, the midline of the patient can be adjusted concurrently with adjusting the sagittal jaw position of the patient using the repositioning jaw elements 1406, 1408, 1410, 1412.

FIG. 14B illustrates an example of a view of an upper jaw 1402 with a first repositioning jaw element 1406 and a third repositioning jaw element 1410 and a lower jaw 1404 with a second repositioning jaw element 1408 and a fourth repositioning jaw element 1404. The jaws 1402, 1404 and repositioning jaw elements 1406, 1408, 1410, 1412 illustrated in FIG. 14B can include the same or different jaws/repositioning jaw elements as illustrated in FIG. 14A, in various embodiments.

As illustrated by the embodiment of FIG. 14B, in a number of embodiments, the surfaces of the repositioning jaw elements (e.g., the right and left posterior side) on the shell of a jaw (e.g., upper or lower) can be angled at the same angle. For instance, the first repositioning element 1406 and the third repositioning jaw element 1410 of the first jaw 1402 are angled at the same angle (e.g., a first angle). Similarly, the second repositioning jaw element 1408 and the fourth repositioning jaw element 1412 are angled at the same angle (e.g., a second angle), which can be an opposite angle as the first repositioning jaw element 1406 and the third repositioning jaw element 1410. However, embodiments in accordance with the present disclosure are not so limited. For instance, the surfaces of repositioning jaw elements on the shell of a jaw (e.g., upper or lower) can be angled at opposing angles, in a number of embodiments.

Further, the embodiments illustrated by FIGS. 14A-14B can include repositioning jaw elements 1406, 1408, 1410, 1412 that adjust the midline of a patient toward the patient's right side. However, embodiments in accordance with the present disclosure are not so limited and can include repositioning jaw elements designed to adjust the midline of a patient toward the patient's left side.

Figure 15A:
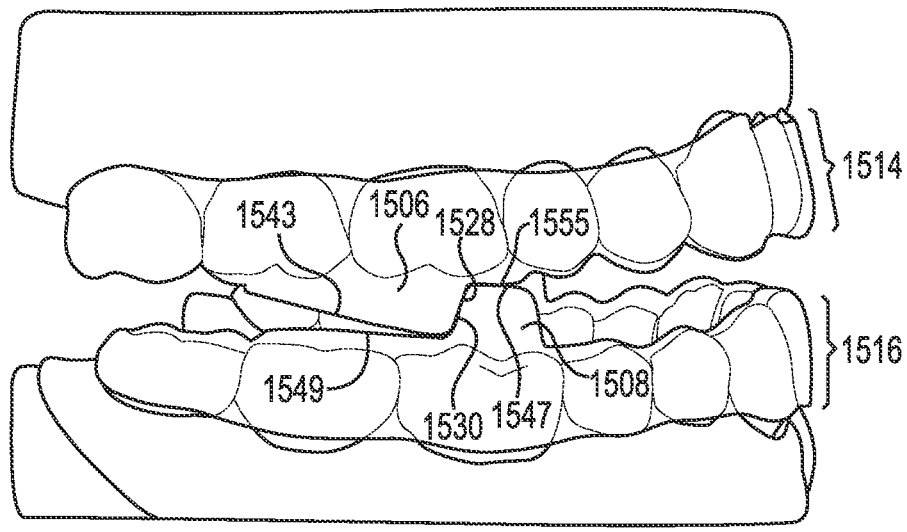
FIGS. 15A-15B illustrates a side view of a first shell with a first repositioning jaw element and a second shell with a second repositioning jaw element according to a number of embodiments of the present disclosure.
Figure 15B:
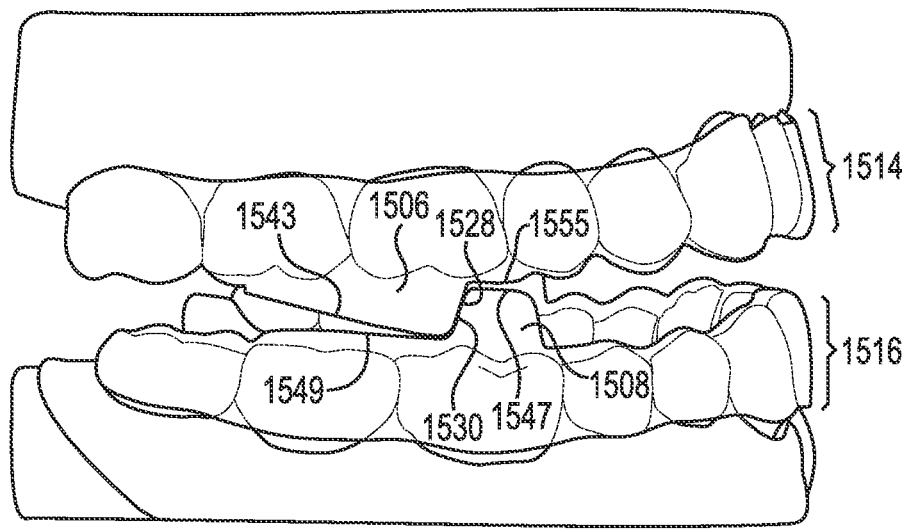

FIGS. 15A-B illustrates a side view of a first shell with a first repositioning jaw element and a second shell with a second repositioning jaw element according to a number of embodiments of the present disclosure. As previously discussed, the first shell 1514 can include a number of tooth apertures configured to receive and reposition a number of teeth of a patient's upper dentition. A first repositioning jaw element 1506 extends from an occlusal surface of the first shell 1514.

The second shell 1516 can include a number of tooth apertures configured to receive and reposition a number of teeth of the patient's lower dentition. A second repositioning jaw element 1508 extends from an occlusal surface of the second shell 1516.

The repositioning jaw elements 1506, 1508 can include a number of surfaces 1528, 1530, 1543, 1547, 1549, 1555. For instance, as previously discussed, the first repositioning jaw element 1506 can include a first surface 1528 and the second repositioning jaw element 1508 can include a second surface 1530 to interface with the first surface 1528 of the first repositioning jaw element 1506. The first repositioning jaw element 1506 and the second repositioning jaw element 1508 can be positioned to interface, interact, and/or otherwise engage in the presence of a fully engaged sagittal jaw position of the patient's upper dentition and the patient's lower dentition in a manner to reposition the patient's lower jaw.

Figure 16A:
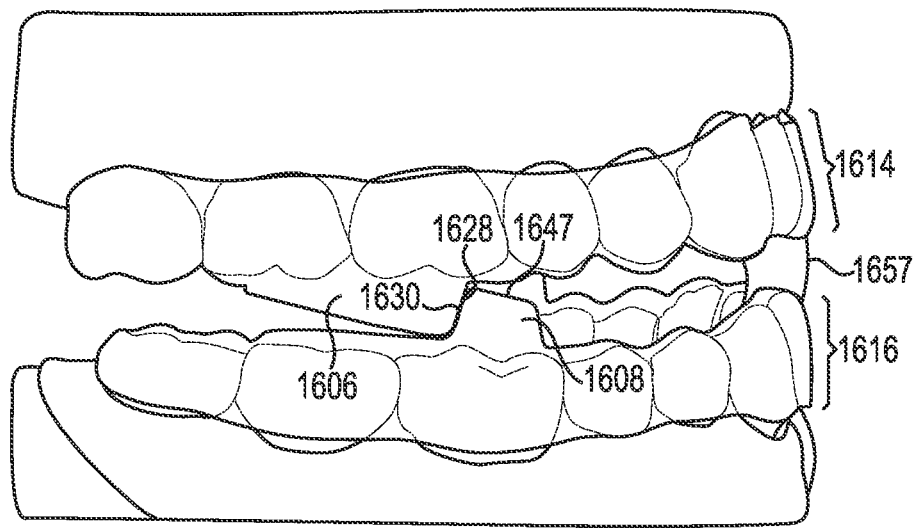
FIG. 16A illustrates a side view of a first shell with a first repositioning jaw element and a second shell with a second repositioning jaw element according to a number of embodiments of the present disclosure.

The number of surfaces 1528, 1530, 1543, 1547, 1549, 1555 can include top surfaces 1543, 1547 of the repositioning jaw elements 1506, 1508, as previously discussed. The top surface 1543 of the first repositioning jaw element 1506 can include a slanted top surface. As previously discussed, a slanted top surface can include a slant in height from the first surface 1528 designed to interface, interact, and/or otherwise engage with one another surface to a back surface (e.g., back surface 538 as illustrated by FIG. 5C) of the first repositioning jaw element 1506. For instance, the slanted top surface 1543 of the first repositioning jaw element 1506 can include a higher coronal-apical height of a repositioning jaw element in a mesial direction than a coronal-apical height of the repositioning jaw element in a distal direction. In some embodiments, the top surface 1547 of the second repositioning jaw element 1508 can include a slanted top surface, as illustrated by FIG. 16A.

As previously discussed in connection with FIG. 5C and FIG. 6, the slanted top surface 1543 of the first repositioning jaw element 1506 can create a more comfortable experience for the patient as the jaw of the patient may not close in a flat direction (e.g., not parallel to a horizontal plane). Further, the top surface 1543 that is slanted can prevent and/or minimize the top surface 1543 of the first repositioning jaw element 1506 from interfacing with surfaces of the shell of the opposing jaw (as discussed further herein).

FIG. 15A illustrates an ideal fit of a first repositioning element 1506 of a first shell 1514 and a second repositioning element 1508 of a second shell 1516 with a predicted corrected jaw position that is accurate. That is, the predicted (e.g., calculated) corrected jaw position can be the same and/or near same as the actual corrected jaw position of the patient. As illustrated, the top surface 1547 of the second repositioning jaw element 1508, in an ideal fit, can be flush with the first plane of material 1555 on the first shell 1514, as discussed further herein.

In various embodiments, the number of surfaces 1528, 1530, 1543, 1547, 1549, 1555 can include a plane of material 1549, 1555 extending from the repositioning jaw elements 1506, 1508. A plane of material 1549, 1555 can include additional material on an occlusal surface of the shell. The material can include the same material that forms the shells 1516, 1514.

As illustrated by FIGS. 15A-15B, a first plane of material 1555 on the first shell 1514 can extend from the first repositioning jaw element 1506 in a mesial direction. A second plane of material 1549 on the second shell 1516 can extend from the second repositioning element 1508 in a distal direction. The planes of material 1549, 1555 can be used to prevent and/or minimize forces on coronal surfaces of teeth beneath the repositioning jaw elements 1506, 1508.

For instance, the first plane of material 1555 can prevent and/or minimize forces created when a patient closes their jaw (e.g., jaw closing forces) from being applied to teeth beneath the first plane of material 1555 and/or beneath the second repositioning jaw element 1508. In an ideal fit of the repositioning jaw elements 1506, 1508, the first plane of material 1555 can contact the top surface 1547 of the second repositioning jaw element 1508. However, in some embodiments, the contact may be present but can, for example, not be a flush contact.

The slanted top surface 1543 of the first repositioning jaw element 1506 can allow for errors in a prediction of the corrected jaw position. If an accurate corrected jaw position is calculated, an ideal position of the repositioning jaw elements 1506, 1508 can include the first surface 1528 and the second surface 1530 being in flush contact and the top surface 1547 of the second repositioning jaw element 1508 being in flush contact with the first plane of material 1555.

However, some error in predicting the corrected jaw position can occur. For example, FIG. 15B illustrates an ideal fit of a first repositioning jaw element 1506 and a second repositioning jaw element 1508 with a predicted corrected jaw position that has some error (e.g., is not accurate) from an actual corrected jaw position of the patient. As illustrated by FIG. 15B, a gap between the top surface 1547 of the second repositioning jaw element 1508 and the first plane of material 1555 can occur while still having contact between the first surface 1528 and the second surface 1530. If the device were designed to have flush contact between the top surface 1543 and the second plane of material 1549, and there was error in predicting the corrected jaw position as compared to the actual corrected jaw position of the patient, then the jaws of the patient may be open more than intended and/or desired due to the top surface 1543 not having flush contact with the second plane of material 1549.

In some embodiments, the second plane of material 1549 can prevent and/or minimize forces created when the patient closes their jaw from being applied to teeth beneath the second plane of material 1549 and/or beneath the first repositioning jaw element 1508. In an ideal fit of the repositioning jaw elements 1506, 1508, the second plane of material 1549 does not contact the top surface 1543 of the first repositioning jaw element 1506. However, in some embodiments, contact may be present but may not be a flush contact.

The mesial-distal distance of each plane of material 1549, 1555 can be based on the mesial-distal distance of the repositioning jaw element on the opposing jaw. For instance, the first plane of material 1555 can extend in a mesial direction from the first repositioning jaw element 1506 for the same and/or near same mesial-distal distance as the second repositioning jaw element 1508 on the opposing jaw extends. The second plane of material 1549 can extend in a distal direction from the second repositioning jaw element 1508 for the same and/or near same mesial-distal distance as the first repositioning jaw element 1506 on the opposing jaw extends.

The slanted top surface 1543 of the first repositioning jaw element 1506 in addition with one or more planes of material 1549, 1555 can be used to create and/or aim for an ideal fit of the repositioning jaw elements 1506, 1508. In some embodiments, an ideal fit of the repositioning jaw elements 1506, 1508 extending from an occlusal surface of the shells 1514, 1516 can include the first surface 1528 of the first repositioning jaw element 1506 interfacing (e.g., contacting) with the second surface 1530 of the second repositioning jaw element 1508, the top surface 1547 of the second repositioning jaw element 1508 interfacing with the first plane of material 1555, and the top surface 1543 of the first repositioning jaw element 1506 not interfacing with (e.g., contacting) the second plane of material 1549 of the second repositioning jaw element 1508, as illustrated by FIG. 15A.

The angle of the slanted top surface 1543 and the plane of materials 1549, 1555 can prevent and/or minimize forces on the coronal surfaces of teeth located beneath the repositioning jaw elements 1506, 1508, and, can allow for the first and the second surfaces 1528, 1530 of the repositioning jaw elements 1506, 1508 to interface to move a position of a misaligned jaw of the patient. For instance, one or more of the top surfaces 1543, 1547 interfacing with one or more of the planes of material 1549, 1555 may prevent and/or minimize the first surface 1528 from interfacing with the second surface 1530 in a manner to reposition the patient's lower jaw.

However, embodiments in accordance with the present disclosure are not limited to the fit of the repositioning jaw elements illustrated by FIGS. 15A-15B. For instance, over time, as a patient wears the first shell 1514 and the second shell 1516, the ideal fit may not exist. That is, the top surfaces 1543, 1547 may or may not contact the planes of material 1549, 1555 as intended when worn by a patient.

The angle of the slanted top surface 1543 of the first repositioning jaw element 1506 can be a set angle for any patient and/or can include a customized angle for a particular patient. A customized angle, as used herein, can include an angle that is revised based on patient data. For instance, an angle of the slanted top surface 1543 can be customized for a particular patient using articulation information of the patient. Articulation information can be information on positioning and/or movement of the jaw of a patient. Articulation information can be obtained from a scan of the patient's mouth, among other techniques.

In some embodiments, the second plane of material 1549 extending from the second repositioning jaw element 1508 may not be present. For instance, in some mandibular advancement cases, the second plane of material 1549 may not be necessary to prevent the top surface 1543 of the first repositioning jaw element 1506 from interfacing with a surface of the second shell 1516 on the opposing jaw of the patient.

In various embodiments, even if the second plane of material 1549 is not used for an ideal fit, the second plane of material 1549 may be used as a region for labeling for manufacturing purposes. For instance, identification information (e.g., numbers and/or letters) can be added to the second plane of material 1549.

FIG. 16A illustrates a side view of a first shell with a first repositioning jaw element and a second shell with a second repositioning jaw element according to a number of embodiments of the present disclosure. As previously discussed, the first shell 1614 can include a number of tooth apertures configured to receive and reposition a number of teeth of a patient's upper dentition. A first repositioning jaw element 1606 extends from an occlusal surface of the first shell 1614.

The second shell 1616 can include a number of tooth apertures configured to receive and reposition a number of teeth of the patient's lower dentition. A second repositioning jaw element 1608 extends from an occlusal surface of the second shell 1616.

As illustrated by FIG. 16A, in some embodiments, the top surfaces 1647 (and 1543 illustrated by FIGS. 15A-15B) of the first repositioning jaw element 1606 and the second repositioning jaw element 1608 can be slanted. Having a slanted top surface 1647 of the second repositioning jaw element 1608 and a slanted top surface (e.g., illustrated by 1543 of FIGS. 15A-15B) of the first repositioning jaw element 1606 can streamline a profile of the dental appliance (e.g., the first shell 1614 and the second shell 1616).

As further illustrated by FIG. 16A, in a number of embodiments, the first shell 1614 can include an anterior stop 1657. An anterior stop 1657 can include a tripod support located at the anterior region of the patient (e.g., proximal to anterior teeth of the patient). The anterior stop 1657 can be formed integrally with and/or of the same material as the first shell 1614 (or the second shell 1616), in accordance with a number of embodiments.

For example, the anterior stop 1657 can extend from the occlusal surface of the first shell 1614 proximal to anterior teeth of the upper jaw. The anterior stop 1657 can rest on the occlusal surface of the second shell 1616 when pressure is placed on the first shell 1614 and the second shell 1616 by the patient.

Alternatively, the anterior stop 1657 can extend from the occlusal surface of the second shell 1616 proximal to anterior teeth of the lower jaw. The anterior stop 1657 can rest on the occlusal surface of the first shell 1614 when pressure is placed on the first shell 1614 and the second shell 1616 by the patient.

In some instances, an arch of a patient may not be parallel. For example, a patient with a high angled mandible, any opening (e.g., posterior opening) created by the repositioning jaw elements 1606, 1608 can lead to a large anterior opening. As an example, the opening can include a 1 to 3 ratio (e.g., for every 1 mm opening in the posterior region, a resulting 3 mm opening in the anterior region of the patient). If the patient pivots around to a back contact point, there can be jaw strain and discomfort.

The anterior stop 1657, as previously discussed, can rest on the occlusal surface of the second shell 1616 when pressure is placed on the first shell 1614 and the second shell 1616 by the patient to provide support when the patient has fully rested their jaws. Further, the anterior stop 1657 can reduce pressure on the repositioning jaw elements 1606, 1608, which can reduce associated flaring.

Figure 16B:
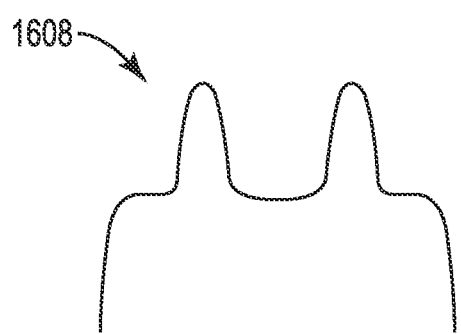
FIG. 16B illustrates a cross-sectional view of the second repositioning jaw element according to a number of embodiments of the present disclosure.

FIG. 16B illustrates a cross-sectional view of the second repositioning jaw element 1608 according to a number of embodiments of the present disclosure. As illustrated by FIG. 16B, in some embodiments, the second repositioning jaw element 1608 can be structured as rigid protrusions (e.g., fins) for adaptation to a molar.

A second repositioning jaw element 1508, as illustrated by FIG. 15B, can lose adaptation to the tooth surface beneath and may lead to flaring of the second shell 1516 when pressure is placed on the second repositioning jaw element 1508. By contrast, the rigid protrusions, as illustrated by FIG. 16B, can reduce flaring (e.g., buccal-lingual flaring) of the shell.

Listing of Exemplary Embodiments:

A. A removable dental appliance comprising:
 a. a first shell having a number of tooth apertures configured to receive and reposition a number of teeth of a patient's upper dentition;
 b. a second shell having a number of tooth apertures configured to receive and reposition a number of teeth of the patient's lower dentition;
 c. a first repositioning jaw element that extends from an occlusal surface of the first shell and includes a first surface;
 d. a second repositioning jaw element that extends from an occlusal surface of the second shell and includes a second surface to interface with the first surface of the first repositioning jaw element;
 e. wherein:
   the first repositioning jaw element and the second repositioning jaw element are positioned to interface in a presence of a fully engaged sagittal jaw position of the patient's upper dentition and the patient's lower dentition in a manner to reposition the patient's jaw;
   the first repositioning jaw element includes a slanted top surface; and
   the first repositioning jaw element and second repositioning jaw element interface at a slant; and
 f. wherein the removable dental appliance is configured to reposition the number of teeth of the patient's upper dentition and the number of teeth of the patient's lower dentition concurrently with the repositioning of the patient's jaw.

B. The removable dental appliance of claim A, wherein the slanted top surface includes a higher coronal-apical height of the first repositioning jaw element in a mesial direction of the first repositioning jaw element than a coronal-apical height of the first repositioning jaw element in a distal direction.

C. The removable dental appliance of claim A, wherein:
 the first surface of the first repositioning jaw element includes a slanted surface on a mesial-facing surface of the first repositioning jaw element; and
 the second surface of the second repositioning jaw element includes a slanted surface on a distal-facing surface of the second repositioning jaw element.

D. The removable dental appliance of claim A, wherein the first shell includes a plane of material extending from the first repositioning jaw element in a mesial direction.

E. The removable dental appliance of claim D, wherein the plane of material includes a first plane of material and the second shell includes a second plane of material extending from the second repositioning jaw element in a distal direction.

F. The removable dental appliance of claim A, wherein at least one of the first repositioning jaw element and the second repositioning jaw element are positioned to generate distalizing force on at least some of the teeth within.

G. The removable dental appliance of claim A, wherein:
 a. the first repositioning jaw element includes a first geometric feature; and
 b. the second repositioning jaw element includes a second geometric feature shaped to mate with the first geometric feature.

H. The removable dental appliance of claim C, wherein the first geometric feature includes a protrusion and the second geometric feature includes a socket.

I. The removable dental appliance of claim A, wherein at least one of the first repositioning jaw element and the second repositioning jaw element include a layer of compressible material on a surface.

J. The removable dental appliance of claim A, wherein at least one of the first surface and the second surface are angled to adjust a midline of patient.

K. The removable dental appliance of claim A, wherein the first repositioning jaw element and the second repositioning jaw elements include occlusal surfaces to follow contours of occlusal surfaces of teeth on an opposing jaw.

L. The removable dental appliance of claim A, wherein at least one of the first repositioning jaw element and the second repositioning jaw element include side surface features that extend beyond the occlusal plane of the removable dental appliance to engage with at least one of a buccal and a lingual side surfaces of a shell of an opposite jaw.

M. The removable dental appliance of claim A, wherein the first repositioning jaw element and the second repositioning jaw element are positioned near at least one of an unerupted and a removed molar tooth of the patient.

N. The removable dental appliance of claim A, wherein the first shell and the second shell include a plurality of repositioning jaw elements extending from at least one of a buccal and lingual surface of the first shell and the second shell.

O. The removable dental appliance of claim A, wherein the first repositioning jaw element and the second repositioning jaw element include at least a magnet within to interact and guide the lower jaw into a position.

P. The removable dental appliance of claim A, wherein at least one of the first repositioning jaw element and the second repositioning jaw element includes a top surface with a wider buccal-lingual width than a buccal-lingual width of a bottom surface.

Q. A removable dental appliance comprising:
  a. a first shell having a number of tooth apertures configured to receive and reposition a number of teeth of a patient's upper dentition;
  b. a second shell having a number of tooth apertures configured to receive and reposition a number of teeth of the patient's lower dentition;
  c. a first repositioning jaw element that extends from a buccal or lingual surface of the first shell and includes a first surface;
  d. a second repositioning jaw element that extends from a buccal or lingual surface of the second shell and includes a second surface to interface with the first surface of the first repositioning jaw element;
  e. wherein the first repositioning jaw element and the second repositioning jaw element are positioned to interface as the patient moves to a fully engaged sagittal jaw position of the patient's upper dentition and the patient's lower dentition in a manner to reposition the patient's jaw and wherein the first repositioning jaw element and the second repositioning jaw element crisscross when interfacing; and
  f. wherein the removable dental appliance is configured to reposition the number of teeth of the patient's upper dentition and the number of teeth of the patient's lower dentition concurrently with the repositioning of the patient's jaw.

R. The removable dental appliance of claim Q, wherein the first repositioning jaw element extends past an occlusal surface of the first shell and the second repositioning jaw element extends past an occlusal surface of the second shell.

S. The removable dental appliance of claim Q, wherein the crisscross of the first repositioning jaw element and the second repositioning jaw element includes a crisscross of the first surface and the second surface interfacing when viewed from an anterior or posterior position.

T. The removable dental appliance of claim Q, wherein the first repositioning jaw element and the second repositioning jaw element comply with an occlusal plane normal of the patient.

U. The removable dental appliance of claim Q, wherein the first repositioning jaw element and the second repositioning jaw element include a top groove on a top surface of the repositioning jaw elements and a number of side grooves on side surfaces of the repositioning jaw elements.

V. The removable dental appliance of claim Q, wherein the side grooves include coronal-apical grooves positioned at interproximal regions of at least one tooth of the number of teeth that the repositioning jaw elements extend from.

W. The removable dental appliance of claim Q, wherein:
  the repositioning jaw element includes a structure to indicate to a patient that the patient has positioned the first and second repositioning jaw elements of the first shell and second shell in a fully engaged sagittal jaw position.

X. The removable dental appliance of claim Q, wherein:
  the first repositioning jaw element and the second repositioning jaw element are positioned to interface as the patient moves to a fully engaged sagittal jaw position of the patient's upper dentition and the patient's lower dentition in a manner to reposition the patient's jaw in an anterior-posterior plane with respect to the jaws of the patient.

Y. A removable dental appliance comprising:
  a. a first shell having a number of tooth apertures configured to receive and reposition a number of teeth of a patient's upper dentition;
  b. a second shell having a number of tooth apertures configured to receive and reposition a number of teeth of the patient's lower dentition;
  c. wherein the first shell and the second shell interface in a presence of a fully engaged sagittal jaw position of the patient's upper dentition and the patient's lower dentition in a manner to reposition the patient's jaw; and
  d. wherein the removable dental appliance is configured to reposition the number of teeth of the patient's upper dentition and the number of teeth of the patient's lower dentition concurrently with the repositioning of the patient's jaw.

Z. The removable dental appliance of claim Y, wherein:
  a. the first shell includes a protrusion; and
  b. the second shell includes a socket shaped to mate with the protrusion to move a lower jaw of the patient from an articulation path of opening to a desired range of jaw opening extending from a current occluding position.

AA. The removable dental appliance of claim Y, wherein the first shell and the second shell include occlusal surfaces with a geometry that differs from the contours of the occlusal surfaces of the teeth of an opposing jaw.

BB. The removable dental appliance of claim Y, wherein:
  a. the first shell includes a spring; and
  b. the second shell includes a tab to interact with the spring.

CC. The removable dental appliance of claim Y, wherein the first shell and the second shell each include a plurality of ridges on occlusal surfaces to guide the jaw into a position.

DD. The removable dental appliance of claim Y, wherein the first shell and the second shell include pairs of magnets within occlusal surfaces of the first shell and the second shell to interact and guide the jaw of the patient into a position.

EE. The removable dental appliance of claim Y, wherein occlusal surfaces of the first shell and the second shell include a geometry to match a jaw position.

FF. The removable dental appliance of claim Y, wherein the first shell and the second shell are connected by a rigid or flexible connecting structure to move a lower jaw into a position.

GG. The removable dental appliance of claim Y, wherein the first shell and the second shell are connected by material at a right posterior side and a left posterior side of the first shell and the second shell.

HH. The removable dental appliance of claim Y, wherein:
  a. the first shell includes a repositioning jaw element with a groove; and b. the second shell includes a geometric feature to interact with the groove.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A non-transitory computing device readable medium storing instructions executable by a processor to cause a computing device to perform a method, the method comprising:
    scanning the patient's dentition with a scanner to form a virtual image of the patient's jaw;
    identifying a jaw position of a misaligned jaw of a patient from the virtual image of the patient's jaw;
    providing a treatment plan for the patient, the treatment plan including first instructions to apply one or more tooth repositioning forces to reposition at least one tooth of the patient and second instructions to apply one or more jaw repositioning forces to modify the jaw position of the misaligned jaw;
    gathering virtual representations of a first repositioning jaw element and a second repositioning jaw element, the first repositioning jaw element and the second repositioning jaw element being configured to apply the one or more jaw repositioning forces to modify the jaw position of the misaligned jaw;
    virtually modeling application of the one or more jaw repositioning forces by the first repositioning jaw element or the second repositioning jaw element to obtain a virtual model of the application of the jaw repositioning forces on a virtual model of the patient's jaw;
    using the virtual model of the application of the jaw repositioning forces to identify one or more constraints limiting the application of the one or more jaw repositioning forces to the misaligned jaw; and
    providing adjustment instructions to adjust the first repositioning jaw element and the second repositioning jaw element to accommodate the one or more constraints.

2. The non-transitory computing device readable medium of claim 1, wherein the one or more constraints include physical limitations or restrictions of a placement and an orientation of the repositioning jaw elements in relation to a current tooth arrangement, a current jaw position, and a predicted corrected jaw position of the patient.

3. The non-transitory computing device readable medium of claim 1, wherein the one or more constraints include a slant of an interface between a first surface of the first repositioning jaw element and a second surface of the second repositioning jaw element are within a threshold degree of parallel to an occlusal plane normal of the patient.

4. The non-transitory computing device readable medium of claim 1, wherein the number of constraints include the repositioning jaw elements crisscross when viewed posteriorly or anteriorly.

5. The non-transitory computing device readable medium of claim 1, wherein the adjustment instructions satisfy the greatest subset of the one or more constraints to optimize placement of the repositioning jaw elements.

6. The non-transitory computing device readable medium of claim 1, wherein identifying the jaw position includes identifying one of a plurality of virtual jaw positions of a virtual model of the jaw of the patient between incremental treatment stages of the treatment plan.

7. The non-transitory computing device readable medium of claim 1, further comprising modifying the treatment plan to accommodate the adjustment instructions.

8. The non-transitory computing device readable medium of claim 1, further comprising: providing instructions to model the one or more constraints on the virtual model of the patient's jaw.

9. A non-transitory computing device readable medium storing instructions executable by a processor to cause a computing device to perform a method, the method comprising:
    scanning the patient's dentition with a scanner to form a virtual image of the patient's jaw;
    providing a treatment plan for a patient based on the virtual image, the treatment plan including first instructions to apply one or more tooth repositioning forces to reposition at least one tooth of the patient and second instructions to apply one or more jaw repositioning forces to modify a jaw position of a jaw of the patient;
    identifying an estimated jaw position of the patient, the estimated jaw position being from a plurality of virtual jaw positions associated with a virtual model of the jaw of the patient, each of the plurality of virtual jaw positions associated with one of a plurality of stages of the treatment plan;
    gathering a virtual representation of a first repositioning jaw element and a second repositioning jaw element;
    virtually positioning the virtual representation of the first repositioning jaw element on a virtual model of the patient's jaw and the virtual representation of the second repositioning jaw element on the virtual model of the patient's jaw in order to model application of the one or more jaw repositioning forces to modify the jaw position of the patient's jaw; and
    virtually modeling application of the one or more of the jaw repositioning forces and the tooth repositioning forces by the first repositioning jaw element and the second repositioning jaw element to obtain a virtual model of the application of the one or more jaw repositioning forces;
    using the virtual model of the application of the one or more of the jaw repositioning forces to identify one or more constraints limiting the application of the jaw repositioning forces to the misaligned jaw; and providing adjustment instructions to adjust one or more of the first repositioning jaw element and the second repositioning jaw element to accommodate the one or more constraints.

10. The non-transitory computing device readable medium of claim 9, wherein the method further comprises providing a plurality of virtual models of dental appliances for each stage of the treatment plan.

11. The non-transitory computing device readable medium of claim 10, wherein the method further comprises adjusting the position of the virtual representations of the first and second repositioning jaw elements at one or more intermediate stages of the plurality of stages of the treatment plan.

12. The non-transitory computing device readable medium of claim 11, wherein the method further comprises interpolating the position of the virtual representations of the first and second repositioning jaw elements at first and the last stages of the plurality of stages with the adjusted position at the one or more intermediate stages.

13. The non-transitory computing device readable medium of claim 9, wherein the method further comprises adjusting the position of the virtual representations of the first and second repositioning jaw elements to comply with the one or more constraints.

14. The non-transitory computing device readable medium of claim 9, wherein adjusting the position of the virtual representations of the first and second repositioning jaw elements includes adjusting the virtual representations of the first and second repositioning jaw elements to an ideal fit based on the one or more constraints.

15. The non-transitory computing device readable medium of claim 9, wherein the instructions are executable to perform the method including beveling side surfaces of the virtual representations of the first and second repositioning jaw elements to include a different buccal-lingual width on a bottom surface than a buccal-lingual width on a top surface of the virtual representations of the first and second repositioning jaw elements.

16. The non-transitory computing device readable medium of claim 9, wherein the instructions are executable to perform the method including placing a groove on a top surface of the virtual representations of the first or second repositioning jaw element.

17. The non-transitory computing device readable medium of claim 9, wherein the instructions are executable to perform the method including placing a side groove on at least one of a buccal side surface and a lingual side surface of the virtual representations of the first or second repositioning jaw element.

18. The non-transitory computing device readable medium of claim 9, wherein the instructions are further executable to perform the method including curving side surfaces of the virtual representations of the first or second repositioning jaw element in at least one of a buccal direction and a lingual direction.

19. A method of designing a dental appliance, the method comprising:
scanning the patient's dentition with a scanner to form a virtual image of the patient's jaw;
providing a treatment plan for a patient based on the virtual image, the treatment plan including first instructions to apply one or more tooth repositioning forces to reposition at least one tooth of the patient and second instructions to apply one or more jaw repositioning forces to modify a jaw position of a jaw of the patient;
identifying an estimated jaw position of the patient, the estimated jaw position being from a plurality of virtual jaw positions associated with a virtual model of the jaw of the patient, each of the plurality of virtual jaw positions associated with one stage of a plurality of stages of the treatment plan;
gathering a virtual representation of a first repositioning jaw element and a second repositioning jaw element;
virtually positioning the first and second repositioning jaw elements on a virtual model of the patient's jaw at the one stage of the plurality of stages of the treatment plan;
virtually modeling application of one or more of the jaw repositioning forces and the tooth repositioning forces; and
providing adjustment instructions to adjust one or more of the first repositioning jaw element and the second repositioning jaw element to accommodate the one or more constraints.

20. The method of claim 19, wherein the virtual representations of the first and second repositioning jaw elements are positioned at a first stage and a last stage of the plurality of stages of the treatment plan and the method further including refining a position of the virtual representations of the first and second repositioning jaw elements at an intermediate stage of the range of stages.

21. The method of claim 20, the method further including interpolating a position of the virtual representations of the first and second repositioning jaw elements at the first and last stages with the refined position of the virtual representations of the first and second repositioning jaw elements at the intermediate stage.

22. The method of claim 21, wherein adjusting the position of the first and second repositioning jaw elements includes adjusting the position at the first stage, the last stage, and the intermediate stage of the plurality of stages to comply with the one or more constraints.

23. The method of claim 19, wherein the first and second repositioning jaw elements extend from an occlusal surface of a first shell and a second shell of orthodontic appliances configured to provide tooth repositioning forces at the one of the plurality of stages and the one or more constraints include aligning an interface of the first and second repositioning jaw elements with an occlusal plane normal of the patient.

24. The method of claim 23, wherein the one or more constraints further include a distance between each repositioning jaw element and a coronal surface of a tooth on the opposing jaw is greater than a threshold distance.

25. The method of claim 24, wherein the number of constraints further include a tooth surface of a tooth beneath each repositioning jaw element does not extend through a surface of each respective repositioning jaw element, each repositioning jaw element does not violate buccal-lingual borders of occlusal surfaces of the teeth beneath, each repositioning jaw element aligns with an arch curve direction, angulation of each repositioning jaw element in a buccal-lingual direction is limited, each repositioning jaw element is positioned from the 1st molar to the 1st bicuspid, at least one molar on the lower jaw is uncovered by a repositioning jaw element, and a specific bite registration configuration.

26. The method of claim 19, wherein the repositioning jaw elements extend from a buccal or lingual surface of a first shell and a second shell of orthodontic appliances configured to provide tooth repositioning forces at the one of the plurality of stages and the number of constraints include aligning an interface of the repositioning jaw elements with an occlusal plane normal of the patient.

27. The method of claim 26, wherein the one or more constraints further include the first and second repositioning jaw elements crisscross when viewed posteriorly or anteriorly.

28. The method of claim 27, wherein the one or more constraints further include a distance between each repositioning jaw element and a coronal surface of a tooth on the opposing jaw is greater than a threshold distance, coronal surface of a tooth supports the repositioning jaw elements, avoid undercut, minimize angulation in buccal or lingual direction, the repositioning jaw elements align with an arch curve direction, the repositioning jaw elements are positioned from the $1^{st}$ molar to the $1^{st}$ bicuspid, and symmetry of the repositioning jaw elements on the left side and right side of the jaw.

29. The method of claim 19, further comprising inputting a scan of the actual bite or of a mounted articulation of the bite to position one or more of the first repositioning jaw element and the second repositioning jaw element.

* * * * *